United States Patent
Paulini et al.

(10) Patent No.: US 10,117,430 B2
(45) Date of Patent: Nov. 6, 2018

(54) MALONONITRILE COMPOUNDS FOR CONTROLLING ANIMAL PESTS

(71) Applicant: BASF SE, Ludwigshafen (DE)

(72) Inventors: Ralph Paulini, Cary, NC (US);
Matthias Pohlman, Freinsheim (DE);
Sebastian Soergel, Ludwigshafen (DE);
Henricus Maria Martinus Bastiaans, Chapel Hill, NC (US); Sarah Thompson, Raleigh, NC (US); Cecille Ebuenga Doyog, Los Banos (PH);
Anna Malveda Umali, Quezon (PH);
Rhoel Suiza Cosare, Calauan Laguna Brgy. Sto. Tomas (PH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/650,731

(22) PCT Filed: Dec. 6, 2013

(86) PCT No.: PCT/EP2013/075794
§ 371 (c)(1),
(2) Date: Jun. 9, 2015

(87) PCT Pub. No.: WO2014/090700
PCT Pub. Date: Jun. 19, 2014

(65) Prior Publication Data
US 2016/0066573 A1    Mar. 10, 2016

Related U.S. Application Data

(60) Provisional application No. 61/737,114, filed on Dec. 14, 2012.

(51) Int. Cl.
| | | |
|---|---|---|
| A01N 37/34 | (2006.01) |
| C07D 213/57 | (2006.01) |
| C07D 237/08 | (2006.01) |
| C07D 239/26 | (2006.01) |
| C07D 241/12 | (2006.01) |
| A01N 43/40 | (2006.01) |
| A01N 43/54 | (2006.01) |
| A01N 43/58 | (2006.01) |
| C07C 255/09 | (2006.01) |
| C07C 255/10 | (2006.01) |
| C07C 255/13 | (2006.01) |
| C07D 213/61 | (2006.01) |
| C07D 237/12 | (2006.01) |
| C07D 239/30 | (2006.01) |
| C07D 241/16 | (2006.01) |

(52) U.S. Cl.
CPC ............ *A01N 37/34* (2013.01); *A01N 43/40* (2013.01); *A01N 43/54* (2013.01); *A01N 43/58* (2013.01); *C07C 255/09* (2013.01); *C07C 255/10* (2013.01); *C07C 255/13* (2013.01); *C07D 213/57* (2013.01); *C07D 213/61* (2013.01); *C07D 237/08* (2013.01); *C07D 237/12* (2013.01); *C07D 239/26* (2013.01); *C07D 239/30* (2013.01); *C07D 241/12* (2013.01); *C07D 241/16* (2013.01)

(58) Field of Classification Search
None
See application file for complete search history.

(56) References Cited

U.S. PATENT DOCUMENTS

| | | |
|---|---|---|
| 5,013,659 A | 5/1991 | Bedbrook et al. |
| 5,559,024 A | 9/1996 | Leroux et al. |
| 6,222,100 B1 | 4/2001 | Anderson et al. |
| 6,689,356 B1 | 2/2004 | Zlotkin et al. |
| 7,491,738 B2 | 2/2009 | Goto et al. |
| 7,612,100 B2 | 11/2009 | Koyanagi et al. |
| 7,662,972 B2 | 2/2010 | Mita et al. |
| 7,872,036 B2 | 1/2011 | Toriyabe et al. |
| 7,880,006 B2 | 2/2011 | Yamamoto et al. |
| 8,222,280 B2 | 7/2012 | Liu et al. |
| 8,404,861 B2 | 3/2013 | Furuya et al. |
| 8,563,546 B2 | 10/2013 | Li et al. |
| 8,957,214 B2 | 2/2015 | Kagabu et al. |
| 9,000,189 B2 | 4/2015 | Bretschneider et al. |

(Continued)

FOREIGN PATENT DOCUMENTS

| | | |
|---|---|---|
| CN | 102613183 | 8/2012 |
| EP | 0142924 | 5/1985 |

(Continued)

OTHER PUBLICATIONS

Mastracchio, MacMillan Lab. Group Meeting (2008), Lewis-Base Catalysis.*

(Continued)

*Primary Examiner* — Hasan S Ahmed
(74) *Attorney, Agent, or Firm* — Brinks Gilson & Lione

(57) ABSTRACT

The invention relates to the use of a compound of formula (I)

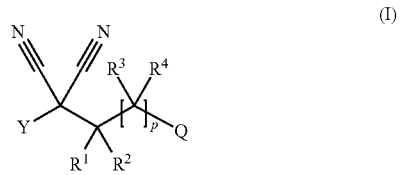

or a salt thereof for combating animal pests,
where the symbols and indices are defined in the specification.

23 Claims, No Drawings

(56) References Cited

U.S. PATENT DOCUMENTS

| | | |
|---|---|---|
| 2005/0214336 A1 | 9/2005 | Turberg et al. |
| 2011/0046186 A1 | 2/2011 | Li et al. |
| 2012/0046301 A1 | 2/2012 | Frank et al. |

FOREIGN PATENT DOCUMENTS

| | | |
|---|---|---|
| EP | 0193259 | 9/1986 |
| EP | 0242236 | 10/1987 |
| EP | 0242246 | 10/1987 |
| EP | 0257993 | 3/1988 |
| EP | 0374753 | 6/1990 |
| EP | 0392225 | 10/1990 |
| EP | 0427529 | 5/1991 |
| EP | 0451878 | 10/1997 |
| EP | 1555259 | 7/2005 |
| JP | 2002284608 | 10/2002 |
| JP | 2004099593 | 4/2004 |
| JP | 2004099597 | 4/2004 |
| WO | WO 1991013972 | 9/1991 |
| WO | WO 1991019806 | 12/1991 |
| WO | WO 1992000377 | 1/1992 |
| WO | WO 1992002526 | 2/1992 |
| WO | WO 1992011376 | 7/1992 |
| WO | WO 1992014827 | 9/1992 |
| WO | WO 1993007278 | 4/1993 |
| WO | WO 1995034656 | 12/1995 |
| WO | WO 1997041218 | 11/1997 |
| WO | WO 1998002526 | 1/1998 |
| WO | WO 1998002527 | 1/1998 |
| WO | WO 2000026390 | 5/2000 |
| WO | WO 2000037422 | 6/2000 |
| WO | WO 2001082685 | 11/2001 |
| WO | WO 2002015701 | 2/2002 |
| WO | WO 2002089579 | 11/2002 |
| WO | WO 2002090320 | 11/2002 |
| WO | WO 2002090321 | 11/2002 |
| WO | WO 2003013225 | 2/2003 |
| WO | WO 2003014356 | 2/2003 |
| WO | WO 2003014357 | 2/2003 |
| WO | WO 2003052073 | 6/2003 |
| WO | WO 2003086075 | 10/2003 |
| WO | WO 2004006677 | 1/2004 |
| WO | WO 2004016073 | 2/2004 |
| WO | WO 2004020399 | 3/2004 |
| WO | WO 2004106529 | 12/2004 |
| WO | WO 2005020673 | 3/2005 |
| WO | WO 2005063694 | 7/2005 |
| WO | WO 2005064823 | 7/2005 |
| WO | WO 2005068432 | 7/2005 |
| WO | WO 2005077934 | 8/2005 |
| WO | WO 2005085216 | 9/2005 |
| WO | WO 2006013896 | 2/2006 |
| WO | WO 2006043635 | 4/2006 |
| WO | WO 2006089633 | 8/2006 |
| WO | WO 2006129714 | 12/2006 |
| WO | WO 2007006670 | 1/2007 |
| WO | WO 2007020986 | 2/2007 |
| WO | WO 2007043677 | 4/2007 |
| WO | WO 2007071609 | 6/2007 |
| WO | WO 2007101540 | 9/2007 |
| WO | WO 2007147888 | 12/2007 |
| WO | WO 2008067911 | 6/2008 |
| WO | WO 2008134969 | 11/2008 |
| WO | WO 2009002809 | 12/2008 |
| WO | WO 2009124707 | 10/2009 |
| WO | WO 2010060379 | 6/2010 |
| WO | WO 2010069266 | 6/2010 |
| WO | WO 2011006946 | 1/2011 |
| WO | WO 2011085575 | 7/2011 |
| WO | WO 2011149749 | 12/2011 |
| WO | WO 2012022487 | 2/2012 |
| WO | WO 2012022681 | 2/2012 |
| WO | WO 2012029672 | 3/2012 |
| WO | WO 2012034403 | 3/2012 |
| WO | WO 2012058116 | 5/2012 |
| WO | WO 2012058134 | 5/2012 |
| WO | WO 2012069266 | 5/2012 |
| WO | WO 2012085645 | 6/2012 |
| WO | WO 2012092115 | 7/2012 |
| WO | WO 2013003977 | 1/2013 |
| WO | WO 2013024009 | 2/2013 |
| WO | WO 2013024010 | 2/2013 |
| WO | WO 2013050317 | 4/2013 |
| WO | WO 2013055584 | 4/2013 |

OTHER PUBLICATIONS

International Search Report, issued in PCT/EP2013/075794, dated Jan. 27, 2014.

International Preliminary Report on Patentability, issued in PCT/EP2013/075794, dated Jun. 16, 2015.

Meyers et al., "Estrogen Receptor-β Potency-Selective Ligands: Structure-Activity Relationship Studies of Diarylpropionitriles and Their Acetylene and Polar Analogues," J. Med. Chem., vol. 44, (2001), pp. 4230-4251.

Atkins et al., "Single Enantiomer, Chiral Donor-Acceptor Metal Compexes from Bisoxazoline Pseudoracemates," Org. Lett., vol. 8, No. 13, (2006), pp. 2759-2762.

Makosza and Chesnokov, "How Iodide Anions Inhibit the Phase-Transfer Catalyzed Reactions of Carbanions," Tetrahedron, vol. 64, (2008), pp. 5925-5932.

Zhang et al., "Conformationally Construction Analogues of N-(Piperidinyl)-5-(4-Chlorophenyl)-1-(2,4-Dichlorophenyl)-4-Methyl-1H-Pyrazole-3-Carboxamide (SR141716): Design, Synthesis, Computational Analysis, and Biological Evaluations," J. Med. Chem., vol. 51, (2008), pp. 3526-3539.

Malona et al., "Total Synthesis of (±)-Rocaglamide via Oxidation-Initiated Nazarov Cyclization," J. Org. Chem., vol. 77, (2012), pp. 1891-1908.

Ghosh et al., "Ticl4-Promoted Tandem Carbonyl or Imine Addition and Friedel-Crafts Cyclization: Synthesis of Benzo-Fused Oxabicyclooctanes and Nonanes," Org. Lett., vol. 14, No. 8, (2012), pp. 2002-2005.

"Catalogue of Pesticide Formulation Types and International Coding System," Technical Monograph No. 2, $6^{th}$ ed., (2008), CropLife International, pp. 1-7.

Mollet and Grubemann, "Emulsions, Suspension, Solid Forms," Formulation Technology, Wiley VCH, (2001), Weinheim, pp. 1-9.

McCutchen's vol. 1: Emulsifiers & Detergents, McCutcheon's Directories, (2008), Glen Rock, USA, pp. 1-2.

The Pesticide Manual, $14^{th}$ ed., C.D.S. Tomlin, British Crop Protection Council, (2011), pp. 1343-1349.

Meyer et al., "Protein Purification by Fusion with an Environmentally Responsive Elastin-Like Polypeptide: Effect of Polypeptide Length on the Purification of Thioredoxin." Biotechnol Prog., vol. 17, No. 4, (2001), pp. 720-728.

Trabbic-Carlson et al., "Effect of Protein Fusion on the Transition Temperature of an Environmentally Responsive Elastin-Like Polypeptide: A Role for Surface Hydrophobicity?" Protein Eng Des Sel, vol. 17, No. 1, (2004), pp. 57-66.

Seyedsayamdost et al., "Site-Specific Incorporation of Fluorotyrosine into the R2 Subunit of E. coli Ribonucleotide Reductase by Expressed Protein Ligation," Nature Protocols, vol. 2, No. 5, (2007), pp. 1225-1235.

Pellois and Muir, "Semisynthetic Proteins in Mechanistic Studies: Using Chemistry to go Where Nature Can't," Curr Opin Chem Biol., vol. 10, No. 4, (2006), pp. 487-491.

Veronese, "Peptide and Protein PEGylation: A Review of Problems and Solutions," Biomaterials, vol. 22, No. 5, (2001), p. 405-417.

Natarajan et al., "Characterization of Site-Specific ScFv PEGylation for Tumor-Targeting Pharmaceuticals," Bioconjugate Chem., vol. 16, No. 1, (2005), pp. 113-121.

* cited by examiner

MALONONITRILE COMPOUNDS FOR CONTROLLING ANIMAL PESTS

This application is a National Stage application of International Application No. PCT/EP2013/075794, filed Dec. 6, 2013, which claims the benefit of U.S. Provisional Application No. 61/737,114, filed Dec. 14, 2012, the entire contents of which are hereby incorporated herein by reference.

The invention relates to aryl alkyl malononitriles, a method for their preparation and their use for combating animal pests, an agricultural composition or seeds comprising said malononitriles, a method for combating animal pests, a method for protecting crops from attack or infestation by animal pests, a method for protecting seeds from soil insects and the seedlings' roots and shoots from soil and foliar insects.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled. However, it is a continuing objective to provide further pesticidal compounds which, at least in some aspects, offer advantages over the known compounds.

Pesticidal compounds having a dicyanoalkane moiety have been disclosed in a number of patent applications, e.g. JP 2002 284608, WO 02/089579, WO 02/090320, WO 02/090321, WO 04/006677, WO 04/020399, JP 2004 99593, JP 2004 99597, WO 05/068432, WO 05/064823, EP 1555259, WO 05/063694, WO 2007/071609, and WO 2007/147888.

It has now been found that particular aryl alkyl malononitriles bearing an additional 6-membered aromatic heterocyclic ring on the aforementioned alkyl group are particularly useful for controlling pests, in particular invertebrate pests.

Accordingly, in one aspect of the invention there is provided a compound of formula (I)

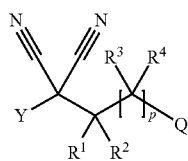

(I)

or a salt or N-oxide thereof,
wherein
Y is phenyl unsubstituted or substituted with 1, 2, 3, 4 or 5 substituents $R^5$; or naphthyl unsubstituted or substituted with 1, 2, 3, 4, 5, 6 or 7 substituents $R^5$;
Q is a 6-membered aromatic heterocyclic ring containing 1, 2, 3 or 4 nitrogen atoms in the ring, wherein the aforementioned ring is unsubstituted or substituted with 1, 2, 3 or 4 substituents $R^6$;
$R^1$ is hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;
$R^2$ is hydrogen or halogen;
or
$R^1$ and $R^2$ form together with the carbon atom to which they are attached a methylene group or a cyclopropyl group;
$R^3$ is hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;
$R^4$ is hydrogen or halogen;
or
$R^3$ and $R^4$ form together with the carbon atom to which they are attached a methylene group or a cyclopropyl group;
each $R^5$, $R^6$ is independently halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;
$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;
phenyl unsubstituted or substituted with up to 5 $R^c$;
a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^d$;
$Si(R^e)_3$, $OR^f$, $SR^f$, $OS(O)_xR^h$, $S(O)_xR^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;
or
two $R^5$ on two adjacent carbon atoms present on one phenyl ring are together a bridge selected from $CH_2CH_2CH_2CH_2$, N=CH—CH=CH, CH=N—CH=CH, N=CH—N=CH, N=CH—CH=N, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from =O, OH, $CH_3$, $OCH_3$, halogen, halomethyl and halomethoxy; preferably are together a bridge selected from $CH_2CH_2CH_2CH_2$, N=CH—CH=CH, CH=N—CH=CH, N=CH—N=CH, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from =O, OH, $CH_3$, $OCH_3$, halogen, halomethyl and halomethoxy;

each $R^7$ is independently halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;

each $R^a$ is independently halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^e)_3$, $OR^A$, $SR^A$, $OSO_2R^B$, $S(O)_xR^B$, —$S(O)_xN(R^D)_2$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$, or two $R^a$ present on one carbon atom are together =O, =C($R^F$)$_2$, =$NR^D$, =$NOR^A$, =$NNR^D$, or two $R^a$ form a 3-, 4-, 5-, 6-, 7- or 8-membered saturated or partially unsaturated carbocyclic or heterocyclic ring together with the carbon atoms the two $R^a$ are bonded to;

each $R^b$ is independently halogen, cyano, azido, nitro, —SCN, $SF_5$, $C_1$-$C_6$-alkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^G)_3$, $OR^H$, $SR^H$, $OSO_2R^J$, $S(O)_xR^J$, —$S(O)_xN(R^K)_2$, $N(R^K)_2$, $C(=O)N(R^K)_2$, $C(=S)N(R^K)_2$, $C(=O)OR^H$, or two $R^b$ present on one carbon atom are together =O, =C($R^L$)$_2$, =$NR^K$, =$NOR^H$, =$NNR^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$;

each $R^d$ is independently halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$, or two $R^d$ present on one atom of a saturated or partially unsaturated heterocyclic ring are together =O, =C($R^L$)$_2$; =$NR^K$, =$NOR^H$ or =$NNR^K$;

each $R^e$ is independently halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^f$ is independently hydrogen, cyano, $C_1$-$C_6$-alkyl, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $S(O)_xR^B$, —$S(O)_xN(R^D)_2$, $N(R^D)_2$, —N=C($R^F$)$_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^h$ is independently hydrogen, cyano, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$N(R^D)_2$, —N=C($R^F$)$_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^i$ is independently hydrogen, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$S(O)_xR^B$, —$S(O)_xN(R^D)_2$, $C(=O)R^S$, $C(=O)OR^A$, $C(=O)N(R^D)_2$, $C(=S)R^S$, $C(=S)SR^A$, $C(=S)N(R^D)_2$, $C(=NR^D)R^S$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$, or two $R^i$ on one nitrogen atom are together a $C_2$-$C_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl, $C_2$-$C_6$-haloalkynyl;

each $R^m$ is independently hydrogen, —SCN, $SF_5$, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $OR^A$, $SR^A$, $OSO_2R^B$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$;

each $R^A$ is independently hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^B$ is independently hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-alkoxy, $C_1$-$C_6$ haloalkoxy and ($C_1$-$C_6$-alkoxy)carbonyl;

each $R^D$ is independently hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$-alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-alkoxy, $C_1$-$C_6$ haloalkoxy and ($C_1$-$C_6$-alkoxy)carbonyl, or two $R^D$ on one nitrogen atom are together a $C_2$-$C_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

each $R^F$ is independently $C_1$-$C_4$ alkyl, $C_1$-$C_6$ cycloalkyl, $C_1$-$C_4$ alkoxyalkyl, phenyl or benzyl;

each $R^G$ is independently halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^J$ is independently hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$ alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently $C_1$-$C_4$ alkyl or $C_1$-$C_4$ alkoxyalkyl;

each $R^M$ is independently halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together =O, =CH($C_1$-$C_4$-alkyl), =O($C_1$-$C_4$-alkyl)$C_1$-$C_4$-alkyl, =N($C_1$-$C_6$-alkyl) or =NO($C_1$-$C_6$-alkyl);

each $R^N$ is independently hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1;
x is 1 or 2,
with the proviso that the following compound is excluded:

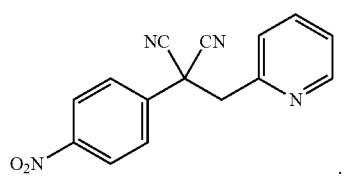 [SMILES: N#CC(C#N)(Cc1ccccn1)c1ccc([N+](=O)[O-])cc1]

In a further aspect of the invention there is provided an agricultural and/or veterinary composition comprising at least one compound of formula (I) according to the invention or a salt or N-oxide thereof. In a preferred embodiment said composition further comprises at least one inert liquid and/or at least one solid carrier.

In yet a further aspect of the invention there is provided the use of a compound of formula (I) according to the invention or a salt or N-oxide thereof for combating animal pests.

In a further aspect of the invention there is provided a method for combating animal pests, which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of formula (I) according to the invention or a salt or N-oxide thereof.

In yet a further aspect of the invention there is provided a method for protecting crops from attack or infestation by animal pests, which comprises contacting the crop with a pesticidally effective amount of at least one compound of formula (I) according to the invention or a salt or N-oxide thereof.

In a further aspect of the invention there is provided a method for protecting seeds from soil insects and the seedlings' roots and shoots from soil and foliar insects, which comprises contacting the seeds before sowing and/or after pregermination with at least one compound of formula (I) according to the invention or a salt or N-oxide thereof.

In yet a further aspect of the invention there are provided seeds comprising at least one compound of formula (I) according to the invention or a salt or N-oxide thereof.

In a further aspect of the invention there is provided the use of a compound of formula (I) according to the invention or a salt or N-oxide thereof for combating parasites in and on animals.

In yet a further aspect of the invention there is provided a method for treating or protecting animals against infestation or infection by parasites, which comprises orally, topically or parenterally administering or applying to the animals a parasiticidally effective amount of at least one compound of formula (I) according to the invention or a salt or N-oxide thereof.

In a further aspect of the invention there is provided a method for the preparation of a composition for treating or protecting animals against infestation or infection by parasites, which comprises mixing a parasiticidally effective amount of at least one compound of formula (I) according to the invention or a salt or N-oxide thereof and at least one solid carrier.

In yet a further aspect of the invention there is provided the use of a compound of formula (I) according to the invention or a salt or N-oxide thereof for the preparation of a medicament for treating or protecting animals against infestation or infection by parasites.

In a further aspect of the invention there is provided a compound of formula (I) according to the invention or a salt or N-oxide thereof as a medicament.

In yet a further aspect of the invention there is provided a method for preparing a compound of formula (I) according to the invention or a salt or N-oxide thereof, comprising the step of reacting a compound of formula (XI),

wherein Y is defined as in formula (I);
with a compound of formula (XII),

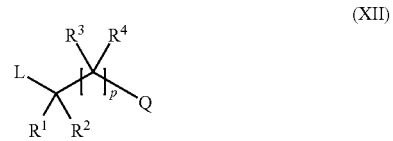

wherein $R^1$, $R^2$, $R^3$, $R^4$, Q and p are defined as in formula (I); and
L is a leaving group;
optionally in the presence of a base.

The present invention also relates to plant propagation materials, in particular seeds, comprising at least one compound of formula I or a salt or N-oxide thereof.

The compounds of the present invention include compounds of formula (I), compounds that are a salt of a compound of formula (I), compounds that are an N-oxide of a compound of formula (I), and compounds that are both a salt and an N-oxide of a compound of formula (I).

The present invention relates to every possible stereoisomer of the compounds of formula I, i.e. to single enantiomers or diastereomers, as well as to mixtures thereof.

The compounds of the present invention may be amorphous or may exist in one or more different crystalline states (polymorphs) or modifications which may have different macroscopic properties such as stability or show different biological properties such as activities. The present invention includes both amorphous and crystalline compounds of formula I, mixtures of different crystalline states or modifications of the respective compound I, as well as amorphous or crystalline salts thereof.

Salts of the compounds of formula I are preferably agriculturally and/or veterinarily acceptable salts. They can be formed in a customary manner, e.g. by reacting the compound with an acid of the anion in question if the compound of formula I has a basic functionality or by reacting an acidic compound of formula I with a suitable base.

Suitable agriculturally or veterinarilly useful salts are especially the salts of those cations or the acid addition salts of those acids whose cations and anions, respectively, do not have any adverse effect on the action of the compounds according to the present invention. Suitable cations are in particular ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of formula I with an acid of the corresponding anion, preferably of hydrochloric acid, hydrobromic acid, sulfuric acid, phosphoric acid or nitric acid.

N-oxides of the compounds of formula I can be formed in a customary manner, e.g. by treating a compound of formula I with a suitable oxidant. Examples of suitable oxidants include hydrogen peroxide, urea hydrogen peroxide (UHP), meta-chloroperbenzoic acid (mCPBA), sodium perborate, sodium percarbonate.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" as used herein refers to fluoro, chloro, bromo and iodo.

The term "partially or fully halogenated" as used herein means that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10, in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, the terms "$C_n$-$C_m$-alkoxy" and "$C_n$-$C_m$-alkylthio" (or the term "$C_n$-$C_m$-alkylsulfenyl", respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or the term "$C_n$-$C_m$-haloalkylsulfenyl", respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms "$C_1$-$C_2$-fluoroalkoxy" and "$C_1$-$C_2$-fluoroalkylthio" refer to $C_1$-$C_2$-fluoroalkyl which is bound to the remainder of the molecule via an oxygen atom or a sulfur atom, respectively.

The term "$C_2$-$C_m$-alkenyl" as used herein refers to a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl and the like.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group.

The term "$C_3$-$C_m$-cycloalkyl" as used herein refers to a monocyclic 3- to m-membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or in particular phenyl.

The term "naphthyl" as used herein refers to 1-naphthyl and 2-naphthyl. Preferably, naphthyl is 2-naphthyl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$" as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl include:
oxiranyl, aziridinyl, azetidinyl, 2 tetrahydrofuranyl, 3-tetrahydrofuranyl, 2 tetrahydrothienyl, 3 tetrahydrothienyl, 2-pyrrolidinyl, 3-pyrrolidinyl, 3 pyrazolidinyl, 4 pyrazolidinyl, 5-pyrazolidinyl, 2 imidazolidinyl, 4 imidazolidinyl, 2-oxazolidinyl, 4-oxazolidinyl, 5 oxazolidinyl, 3-isoxazolidinyl, 4 isoxazolidinyl, 5 isoxazolidinyl, 2 thiazolidinyl, 4-thiazolidinyl, 5-thiazolidinyl, 3 isothiazolidinyl, 4-isothiazolidinyl, 5 isothiazolidinyl, 1,2,4-oxadiazolidin-3-yl, 1,2,4 oxadiazolidin 5 yl, 1,2,4-thiadiazolidin-3-yl, 1,2,4 thiadiazolidin-5-yl, 1,2,4 triazolidin-3-yl, 1,3,4-oxadiazolidin-2-yl, 1,3,4 thiadiazolidin-2-yl, 1,3,4 triazolidin-2-yl, 2-tetrahydropyranyl, 4 tetrahydropyranyl, 1,3-dioxan-5-yl, 1,4-dioxan-2-yl, 2-piperidinyl, 3-piperidinyl, 4-piperidinyl, 3-hexahydropyridazinyl, 4 hexahydropyridazinyl, 2-hexahydropyrimidinyl, 4-hexahydropyrimidinyl, 5 hexahydropyrimidinyl, 2-piperazinyl, 1,3,5-hexahydrotriazin-2-yl and 1,2,4 hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3 dihydrothien-3-yl, 2,4 dihydrothien-2-yl, 2,4-dihydrothien-3-yl, 2-pyrrolin-2-yl, 2-pyrrolin-3-yl, 3 pyrrolin-2-yl, 3-pyrrolin-3-yl, 2-isoxazolin-3-yl, 3-isoxazolin-3-yl, 4 isoxazolin 3 yl, 2-isoxazolin-4-yl, 3-isoxazolin-4-yl, 4-isoxazolin-4-yl, 2 isoxazolin-5-yl, 3-isoxazolin-5-yl, 4-isoxazolin-5-yl, 2-isothiazolin-3-yl, 3 isothiazolin-3-yl, 4-isothiazolin-3-yl, 2-isothiazolin-4-yl, 3-isothiazolin-4-yl, 4 isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3 dihydropyrazol-4-yl, 2,3-dihydropyrazol-5-yl, 3,4-dihydropyrazol-1-yl, 3,4 dihydropyrazol-3-yl, 3,4-dihydropyrazol-4-yl, 3,4-dihydropyrazol-5-yl, 4,5 dihydropyrazol-1-yl, 4,5-dihydropyrazol-3-yl, 4,5-dihydropyrazol-4-yl, 4,5 dihydropyrazol-5-yl, 2,3-dihydrooxazol-2-yl, 2,3-dihydrooxazol-3-yl, 2,3 dihydrooxazol-4-yl, 2,3-dihydrooxazol-5-yl, 3,4-dihydrooxazol-2-yl, 3,4 dihydrooxazol-3-yl, 3,4-dihydrooxazol-4-yl, 3,4-dihydrooxazol-5-yl, 3,4 dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4 di- or tetrahydropyridazinyl, 2-di- or tetrahydropyrimidinyl, 4-di- or tetrahydropyrimidinyl, 5 di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclyl is 5- or 6-membered aromatic heterocyclyl (hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4 thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "6-membered aromatic heterocyclic ring containing 1, 2, 3 or 4 nitrogen atoms in the ring" as used herein refers to pyridyl, pyrimidinyl, pyrazinyl, pyridazinyl, triazinyl and tetrazinyl, preferably pyridyl, pyrimidinyl, pyrazinyl, pyridazinyl and triazinyl, more preferably pyridyl, pyrimidinyl, pyrazinyl and pyridazinyl, even more preferably pyridyl and pyrimidinyl.

The term "6-membered aromatic heterocyclic ring containing 1, 2 or 3 nitrogen atoms in the ring" as used herein refers to pyridyl, pyrimidinyl, pyrazinyl, pyridazinyl and triazinyl, preferably pyridyl, pyrimidinyl, pyrazinyl and pyridazinyl, more preferably pyridyl and pyrimidinyl.

The term "pyridyl" as used herein refers to 2-pyridinyl, 3-pyridinyl and 4-pyridinyl, preferably 2-pyridinyl and 3-pyridinyl.

The term "pyrimidinyl" as used herein refers to 2-pyrimidinyl, 4-pyrimidinyl and 5-pyrimidinyl, preferably 2-pyrimidinyl and 5-pyrimidinyl.

The term "pyrazinyl" as used herein refers to 2-pyrazinyl.

The term "pyridazinyl" as used herein refers to 3-pyridazinyl and 4-pyridazinyl, preferably 3-pyridazinyl.

The term "triazinyl" as used herein refers to 1,2,3-triazin-4-yl, 1,2,3-triazin-5-yl, 1,2,4-triazin-3-yl, 1,2,4-triazin-5-yl, 1,2,4-triazin-6-yl and 1,3,5-triazin-2-yl, preferably 1,2,3-triazin-4-yl, 1,2,4-triazin-3-yl and 1,2,4-triazin-6-yl.

The term "tetrazinyl" as used herein refers to 1,2,4,5-tetrazin-3-yl.

Ring Q is bound to the rest of the compound of formula (I) via one of its carbon atoms (not via a nitrogen atom). If present, a substituent $R^6$ is bound to a carbon atom (not to a nitrogen atom) contained in ring Q. It goes without saying that the number of possible substituents $R^6$ on the ring Q is limited by the number of N atoms contained in ring Q. In case the number of N atoms contained in ring 0 is 1, the maximum possible number of substituents $R^6$ is 4; in case the number of N atoms contained in ring Q is 2, the maximum possible number of substituents $R^6$ is 3; in case the number of N atoms contained in ring Q is 3, the maximum possible number of substituents $R^6$ is 2; in case the number of N atoms contained in ring Q is 4, the maximum possible number of substituents $R^6$ is 1.

The term "$C_2$-$C_7$-alkylene" as used herein refers to a divalent branched or preferably unbranched saturated aliphatic chain having 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2$ and $CH_2CH_2CH_2CH_2CH_2CH_2$.

The term "tri-($C_1$-$C_4$)silyl-$C_2$-$C_4$-alkynyl" as used herein refers to $C_2$-$C_4$-alkynyl substituted with tri-($C_1$-$C_4$)silyl. The term "(trimethylsilyl)ethynyl" as used herein refers to ethynyl substituted with trimethylsilyl.

The term "$C_1$-$C_6$-alkyl-$C_3$-$C_8$-cycloalkyl" as used herein refers to $C_3$-$C_8$-cycloalkyl substituted with $C_1$-$C_6$-alkyl. The term "$C_1$-$C_4$-alkyl-$C_3$-$C_6$-cycloalkyl" as used herein refers to $C_3$-$C_6$-cycloalkyl substituted with $C_1$-$C_4$-alkyl.

Preferably, the term "phenyl unsubstituted or substituted with 1, 2, 3, 4 or 5 substituents $R^5$" means "phenyl unsubstituted or substituted with up to 3 or in the case of halogen up to the maximum possible number of substituents $R^5$", and also preferably "phenyl unsubstituted or substituted with 1, 2, 3 or 4 substituents $R^5$", more preferably "phenyl unsubstituted or substituted with 1, 2 or 3 substituents $R^5$", even more preferably "phenyl unsubstituted or substituted with 1 or 2 substituents $R^5$", and particularly preferably "phenyl unsubstituted or substituted with 1 substituent $R^5$".

Preferably, the term "naphthyl unsubstituted or substituted with 1, 2, 3, 4, 5, 6 or 7 substituents $R^5$" means "naphthyl unsubstituted or substituted with up to 3 or in the case of halogen up to the maximum possible number of substituents $R^5$", more preferably "naphthyl unsubstituted or substituted with up to 3 substituents $R^5$", even more preferably "naphthyl unsubstituted or substituted with up to 2 substituents $R^5$", and particularly preferably "naphthyl unsubstituted or substituted with up to 1 substituent $R^5$".

Preferably, the term "unsubstituted or substituted with 1, 2, 3 or 4 substituents $R^6$" means "unsubstituted or substituted with 1, 2 or 3 substituents $R^6$", more preferably "unsubstituted or substituted with 1 or 2 substituents $R^6$", and even more preferably "unsubstituted or substituted with 1 substituent $R^6$".

Preferably, the term "unsubstituted or substituted with up to 5 $R^c$/$R^d$/$R^E$, e.g. in connection with phenyl or a heterocyclic ring, means "unsubstituted or substituted with up to 3 or in the case of halogen up to the maximum possible number of $R^c$/$R^d$/$R^E$", more preferably "unsubstituted or substituted with up to 2 or in the case of halogen up to the maximum possible number of $R^c$/$R^d$/$R^E$", also more preferably "unsubstituted or substituted with up to 3 $R^c$/$R^d$/$R^E$", and even more preferably "unsubstituted or substituted with up to 2 $R^c$/$R^d$/$R^E$".

Preferably, the term "unsubstituted or substituted with one or more", e.g. in connection with substituents $R^a$, $R^b$ or $R^M$, means "unsubstituted or substituted with up to 5 or in the case of halogen up to the maximum possible number of", more preferably "unsubstituted or substituted with up to 3 or in the case of halogen up to the maximum possible number of", even more preferably "unsubstituted or substituted with up to 2 or in the case of halogen up to the maximum possible number of", also more preferably "unsubstituted or substituted with up to 5", also even more preferably "unsubstituted or substituted with up to 3", and particularly preferably "unsubstituted or substituted with up to 2".

The preferred, more preferred, even more preferred and particularly preferred substituents and embodiments described herein are to be understood as preferred either independently of each other or in every possible combination with each other.

These preferences and embodiments apply to the compounds of the invention, to the use of the compounds of the invention as well as to methods using the compounds of the invention.

Preferred are compounds of formula (I) wherein Y is phenyl unsubstituted or substituted with 1, 2, 3 or 4 substituents $R^5$; or naphthyl unsubstituted or substituted with 1 or 2 substituents $R^5$.

Preferred are compounds of formula (I) wherein Q is a 6-membered aromatic heterocyclic ring containing 1, 2 or 3 nitrogen atoms in the ring, wherein the aforementioned ring is unsubstituted or substituted with 1, 2, 3 or 4 substituents $R^6$.

Preferred are compounds of formula (I) wherein $R^1$ is H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated, and in particular the ones wherein $R^1$ is H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ or $CH_2OSi(Et)_3$.

Preferred are compounds of formula (I) wherein $R^2$ is H or halogen.

Also preferred are compounds of formula (I) wherein $R^1$ and $R^2$ form together with the carbon atom to which they are attached a methylene group.

Preferred are compounds of formula (I) wherein $R^3$ is H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated, and in particular the ones wherein $R^3$ is H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ or $CH_2OSi(Et)_3$.

Preferred are compounds of formula (I) wherein $R^4$ is H or halogen.

Also preferred are compounds of formula (I) wherein $R^3$ and $R^4$ form together with the carbon atom to which they are attached a methylene group.

Preferred are compounds of formula (I) wherein $R^5$ is halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, alkyl)amino, ($C_1$-$C_6$-alkyl)carbonyl or ($C_1$-$C_6$-alkyl)carbonyloxy, wherein the 14 radicals last-mentioned are unsubstituted or substituted with one or more (particularly up to 3 or in the case of halogen up to the maximum possible number) substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated, and in particular the ones wherein $R^5$ is halogen (particularly F), Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, C(O)Me, OAc, C(O)NHMe, $C(O)NMe_2$, $CH_2OMe$ or $CH_2OEt$.

Preferred are compounds of formula (I) wherein $R^6$ is halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, alkyl)amino, ($C_1$-$C_6$-alkyl)carbonyl or ($C_1$-$C_6$-alkyl)carbonyloxy, wherein the 14 radicals last mentioned are unsubstituted or substituted with one or more (particularly up to 3 or in the case of halogen up to the maximum possible number) substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated, and in particular the ones wherein $R^6$ is halogen (particularly F), Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, C(O)Me, OAc, C(O)NHMe, $C(O)NMe_2$, $CH_2OMe$ or $CH_2OEt$.

Also preferred are compounds of formula (I) wherein $R^5$ is halogen, Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, C(O)Me, OAc, C(O)NHMe, $C(O)NMe_2$, $CH_2OMe$ or $CH_2OEt$;
or
two $R^5$ on two adjacent carbon atoms present on one phenyl ring are together a bridge selected from N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted.

Preferred are compounds of formula (I) wherein p is 0 or 1, and in particular the ones wherein p is 0.

More preferred are compounds of formula (I) wherein Y is phenyl unsubstituted or substituted with 1, 2 or 3 substituents $R^5$; or naphthyl unsubstituted or substituted with 1 substituent $R^5$.

More preferred are compounds of formula (I) wherein Q is a 6-membered aromatic heterocyclic ring containing 1, 2 or 3 nitrogen atoms in the ring, wherein the aforementioned ring is unsubstituted or substituted with 1, 2 or 3 substituents $R^6$.

More preferred are compounds of formula (I) wherein $R^1$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ or $CH_2OSi(Et)_3$.

More preferred are compounds of formula (I) wherein $R^2$ is H or halogen.

More preferred are compounds of formula (I) wherein $R^3$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ or $CH_2OSi(Et)_3$.

More preferred are compounds of formula (I) wherein $R^4$ is H or halogen.

More preferred are compounds of formula (I) wherein $R^5$ is halogen, cyano, tri-($C_1$-$C_4$)silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy)carbonyl, wherein the eight radicals last mentioned are unsubstituted or partially or fully halogenated, and in particular the ones wherein $R^5$ is halogen (particularly Cl, F), Me, OMe, CN, $CF_3$, $OCF_3$ or ethynyl.

More preferred are compounds of formula (I) wherein $R^6$ is halogen, cyano, tri-$(C_1$-$C_4)$silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or $(C_1$-$C_6$-alkoxy)carbonyl,
wherein the eight radicals last mentioned are unsubstituted or partially or fully halogenated, and in particular the ones wherein $R^6$ is halogen (particularly Cl, F), Me, OMe, CN, $CF_3$, $OCF_3$ or ethynyl.

More preferred are compounds of formula (I) wherein p is 0 or 1, and in particular the ones wherein p is 0.

Even more preferred are compounds of formula (I) wherein Y is phenyl unsubstituted or substituted with 1 or 2 substituents $R^5$.

Even more preferred are compounds of formula (I) wherein Q is pyridyl, pyrimidinyl, pyrazinyl or pyridazinyl, wherein the aforementioned rings are unsubstituted or substituted with 1 or 2 substituents $R^6$, and in particular the ones wherein Q is pyridyl, pyrimidinyl, pyrazinyl or pyridazinyl, wherein the aforementioned rings are unsubstituted or substituted with 1 substituent $R^6$.

Even more preferred are compounds of formula (I) wherein $R^1$ is H, F, Me, Et, CN, $CH_2CN$ or $CH_2OMe$, and in particular the ones wherein $R^1$ is H.

Even more preferred are compounds of formula (I) wherein $R^2$ is H.

Even more preferred are compounds of formula (I) wherein $R^3$ is H, F, Me, Et, CN, $CH_2CN$ or $CH_2OMe$, and in particular the ones wherein $R^3$ is H.

Even more preferred are compounds of formula (I) wherein $R^4$ is H.

Even more preferred are compounds of formula (I) wherein $R^5$ is F, Cl, CN, ethynyl, Me, OMe or $CF_3$, and in particular the ones wherein $R^5$ is F.

Even more preferred are compounds of formula (I) wherein $R^6$ is F, ethynyl, Br or $CF_3$.

Even more preferred are compounds of formula (I) wherein p is 0 or 1, and in particular the ones wherein p is 0.

Also preferred are compounds of formula (I) wherein all symbols and indices have the preferred meanings.

Also more preferred are compounds of formula (I) wherein all symbols and indices have the more preferred meanings.

Also even more preferred are compounds of formula (I) wherein all symbols and indices have the even more preferred meanings.

Preferred are compounds of formula (I) wherein
Y is phenyl unsubstituted or substituted with 1, 2, 3, 4 or 5 substituents $R^5$; or naphthyl unsubstituted or substituted with 1 or 2 substituents $R^5$;
Q is a 6-membered aromatic heterocyclic ring containing 1, 2 or 3 nitrogen atoms in the ring, wherein the aforementioned ring is unsubstituted or substituted with 1, 2, 3 or 4 substituents $R^6$;
$R^1$ is H, halogen, cyano, $C_1$-$C_6$-alkyl, $C_2$-$C_6$-alkenyl, $C_2$-$C_6$-alkynyl, $C_3$-$C_6$-cycloalkyl or $(C_1$-$C_6$-alkoxy)carbonyl,
wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and $(C_1$-$C_6$-alkoxy)carbonyl,
wherein the six radicals last mentioned are unsubstituted or partially or fully halogenated;
$R^2$ is H or halogen;
or
$R^1$ and $R^2$ form together with the carbon atom to which they are attached a methylene group;
$R^3$ is H, halogen, cyano, $C_1$-$C_6$-alkyl, $C_2$-$C_6$-alkenyl, $C_2$-$C_6$-alkynyl, $C_3$-$C_6$-cycloalkyl or $(C_1$-$C_6$-alkoxy)carbonyl,
wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and $(C_1$-$C_6$-alkoxy)carbonyl,
wherein the six radicals last mentioned are unsubstituted or partially or fully halogenated;
$R^4$ is H or halogen;
or
$R^3$ and $R^4$ form together with the carbon atom to which they are attached a methylene group;
$R^5$ is halogen, cyano, $SF_5$, tri-$(C_1$-$C_4)$silyl-$C_2$-$C_4$-alkynyl, $(C_1$-$C_6$-alkyl)aminocarbonyl, di$(C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, $(C_1$-$C_6$-alkoxy)carbonyl, $(C_1$-$C_6$-alkyl)amino, di-$(C_1$-$C_6$-alkyl)amino, $(C_1$-$C_6$-alkyl)carbonyl or $(C_1$-$C_6$-alkyl)carbonyloxy,
wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy,
wherein the five radicals last mentioned are unsubstituted or partially or fully halogenated;
or
two $R^5$ on two adjacent carbon atoms present on one phenyl ring are together a bridge selected from N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted;
$R^6$ is halogen, cyano, $SF_5$, $(C_1$-$C_5$-alkyl)aminocarbonyl, di$(C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, $(C_1$-$C_6$-alkoxy)carbonyl, $(C_1$-$C_6$-alkyl)amino, di-$(C_1$-$C_6$-alkylamino, $(C_1$-$C_6$-alkyl)carbonyl or $(C_1$-$C_6$-alkyl)carbonyloxy,
wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy,
wherein the five radicals last mentioned are unsubstituted or partially or fully halogenated;
p is 0 or 1.

Also preferred are compounds of formula (I) wherein
Y is phenyl unsubstituted or substituted with 1, 2, 3 or 4 substituents $R^5$; or naphthyl unsubstituted or substituted with 1 or 2 substituents $R^5$;
Q is a 6-membered aromatic heterocyclic ring containing 1, 2 or 3 nitrogen atoms in the ring, wherein the aforementioned ring is unsubstituted or substituted with 1, 2, 3 or 4 substituents $R^6$;
$R^1$ is H, halogen, cyano, $C_1$-$C_6$-alkyl, $C_2$-$C_6$-alkenyl, $C_2$-$C_6$-alkynyl, $C_3$-$C_6$-cycloalkyl or $(C_1$-$C_6$-alkoxy)carbonyl,
wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and $(C_1$-$C_6$-alkoxy)carbonyl, wherein the six radicals last mentioned are unsubstituted or partially or fully halogenated;
$R^2$ is H or halogen;
or
$R^1$ and $R^2$ form together with the carbon atom to which they are attached a methylene group; $R^3$ is H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl,
wherein the five radicals last mentioned are unsubstituted or substituted with 1, 2 or 3 substituents selected from halogen, cyano, hydroxy, OSi($C_1$-$C_6$-alkyl)$_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl,
wherein the six radicals last mentioned are unsubstituted or partially or fully halogenated;
$R^4$ is H or halogen;
or
$R^3$ and $R^4$ form together with the carbon atom to which they are attached a methylene group;
$R^5$ is halogen, cyano, $SF_5$, tri-($C_1$-$C_4$)silyl-$C_2$-$C_4$-alkynyl, ($C_1$-$C_6$-alkyl)aminocarbonyl, di($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, ($C_1$-$C_6$-alkyl)carbonyl or ($C_1$-$C_6$-alkyl)carbonyloxy,
wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy,
wherein the five radicals last mentioned are unsubstituted or partially or fully halogenated;
$R^6$ is halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy,
wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy,
wherein the five radicals last mentioned are unsubstituted or partially or fully halogenated;
p is 0 or 1.

More preferred are compounds of formula (I) wherein
Y is phenyl unsubstituted or substituted with 1, 2, 3, 4 or 5 substituents $R^5$; or naphthyl unsubstituted or substituted with 1 substituent $R^5$;
Q is a 6-membered aromatic heterocyclic ring containing 1, 2 or 3 nitrogen atoms in the ring, wherein the aforementioned ring is unsubstituted or substituted with 1, 2 or 3 substituents $R^6$;
$R^1$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi$(Me)$_3$ or $CH_2OSi$(Et)$_3$;
$R^2$ is H or halogen;
$R^3$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi$(Me)$_3$ or $CH_2OSi$(Et)$_3$;
$R^4$ is H or halogen;
$R^5$ is halogen, cyano, tri-($C_1$-$C_4$)silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy) carbonyl, wherein the eight radicals last mentioned are unsubstituted or partially or fully halogenated;
or
two $R^5$ on two adjacent carbon atoms present on one phenyl ring are together a bridge selected from N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted;
$R^6$ is halogen, cyano, tri-($C_1$-$C_4$)silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy) carbonyl, wherein the eight radicals last mentioned are unsubstituted or partially or fully halogenated;
p is 0 or 1.

Also more preferred are compounds of formula (I) wherein
Y is phenyl unsubstituted or substituted with 1, 2 or 3 substituents $R^5$; or naphthyl unsubstituted or substituted with 1 substituent $R^5$;
Q is a 6-membered aromatic heterocyclic ring containing 1, 2 or 3 nitrogen atoms in the ring, wherein the aforementioned ring is unsubstituted or substituted with 1, 2 or 3 substituents $R^6$;
$R^1$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi$(Me)$_3$ or $CH_2OSi$(Et)$_3$;
$R^2$ is H or halogen;
$R^3$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi$(Me)$_3$ or $CH_2OSi$(Et)$_3$;
$R^4$ is H or halogen;
$R^5$ is halogen, cyano, tri-($C_1$-$C_4$)silyl-$C_2$-$C_4$-alkynyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy)carbonyl, wherein the eight radicals last mentioned are unsubstituted or partially or fully halogenated;
$R^6$ is halogen, cyano, tri-($C_1$-$C_4$)silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy) carbonyl, wherein the eight radicals last mentioned are unsubstituted or partially or fully halogenated;
p is 0 or 1.

Even more preferred are compounds of formula (I) wherein
Y is phenyl unsubstituted or substituted with 1, 2 or 3 substituents $R^5$;
Q is pyridyl, pyrimidinyl, pyrazinyl or pyridazinyl, wherein the aforementioned rings are unsubstituted or substituted with 1 or 2 substituents $R^6$;
$R^1$ is H, F, Me, Et, CN, $CH_2CN$ or $CH_2OMe$;
$R^2$ is H;
$R^3$ is H, F, Me, Et, ON, $CH_2CN$ or $CH_2OMe$;
$R^4$ is H;
$R^5$ is F, Cl, CN, ethynyl, Me, OMe or $CF_3$;
$R^6$ is F, ethynyl, Br or $CF_3$;
p is 0 or 1.

Also even more preferred are compounds of formula (I) wherein
Y is phenyl unsubstituted or substituted with 1 or 2 substituents $R^5$;
Q is pyridyl, pyrimidinyl, pyrazinyl or pyridazinyl, wherein the aforementioned rings are unsubstituted or substituted with 1 or 2 substituents $R^6$;
$R^1$ is H, F, Me, Et, CN, $CH_2CN$ or $CH_2OMe$;
$R^2$ is H;
$R^3$ is H, F, Me, Et, CN, $CH_2CN$ or $CH_2OMe$;

$R^4$ is H;

$R^5$ is F, Cl, CN, ethynyl, Me, OMe or $CF_3$;

$R^6$ is F, ethynyl, Br or $CF_3$;

p is 0 or 1.

Particularly preferred are compounds of formula (I) wherein Y is 4-fluorophenyl, 3-fluorophenyl, 2-fluorophenyl, 4-chlorophenyl, 3-cyanophenyl, 4-ethynylphenyl, 3-methylphenyl, 3-methoxyphenyl, 4-trifluoromethylphenyl, 3,5-difluorophenyl or 3,4,5-trifluorophenyl.

Also particularly preferred are compounds of formula (I) wherein Y is 4-fluorophenyl, 3-fluorophenyl, 2-fluorophenyl, 4-chlorophenyl, 3-cyanophenyl, 4-ethynylphenyl, 3-methylphenyl, 3-methoxyphenyl, 4-trifluoromethylphenyl or 3,5-difluorophenyl.

Also particularly preferred are compounds of formula (I) wherein Y is 3,4,5-trifluorophenyl.

Also particularly preferred are compounds of formula (I) wherein Q is 2-pyridyl, 3-pyridyl or 5-pyrimidinyl, wherein the aforementioned rings are unsubstituted or substituted with one or more $R^6$, particularly 2-pyridyl, 3-pyridyl or 5-pyrimidinyl, wherein the aforementioned rings are unsubstituted or substituted with 1 or 2 $R^6$ (particularly F, ethynyl, Br, $CF_3$).

Particular preference is given to compounds of formula (I) wherein $R^1$, $R^2$, $R^3$ and $R^4$ are H.

Very particular preference is given to compounds of formula (I) wherein $R^1$ and $R^2$ are H; and p is 0.

In a preferred embodiment Q is pyridyl or pyrimidinyl, wherein the aforementioned rings are unsubstituted or substituted with one or more $R^6$, particularly pyridyl or pyrimidinyl, wherein the aforementioned rings are unsubstituted or substituted with 1 or 2 $R^6$.

In one embodiment $R^1$ and $R^2$ do not form together with the carbon atom to which they are attached a methylene group.

In a further embodiment $R^3$ and $R^4$ do not form together with the carbon atom to which they are attached a methylene group.

In yet a further embodiment neither $R^1$ and $R^2$ nor $R^3$ and $R^4$ form together with the carbon atom to which they are attached a methylene group.

Further preferred compounds of formula (I) are compounds of formulae (Ia-1), (Ia-2) or (Ia-3),

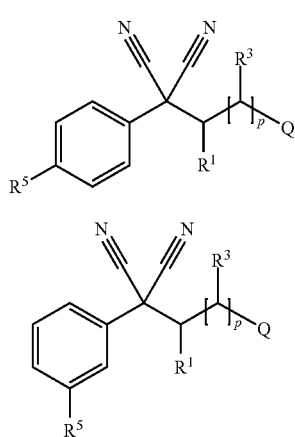

(Ia-1)

(Ia-2)

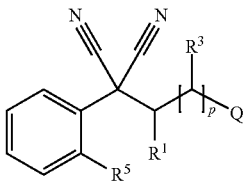

(Ia-3)

wherein Y is phenyl substituted with 1 substituent $R^5$; $R^2$ is H; $R^4$ is H; Q is as defined in formula (I); and p, $R^1$, $R^3$ and $R^5$ are as defined in Table A.

The compounds of formulae (Ia-1), (Ia-2) or (Ia-3) include the respective compounds wherein Y=unsubstituted phenyl. In line with this, the symbol "-" in column "$R^5$" in table A means that the corresponding compounds do not carry a substituent $R^5$, i.e. Y=unsubstituted phenyl.

TABLE A

| No. | p | $R^1$ | $R^3$ | $R^5$ |
|---|---|---|---|---|
| A-001 | 0 | H | — | — |
| A-002 | 0 | H | — | F |
| A-003 | 0 | H | — | Cl |
| A-004 | 0 | H | — | Br |
| A-005 | 0 | H | — | Me |
| A-006 | 0 | H | — | Et |
| A-007 | 0 | H | — | iPr |
| A-008 | 0 | H | — | cPr |
| A-009 | 0 | H | — | tBu |
| A-010 | 0 | H | — | OMe |
| A-011 | 0 | H | — | OEt |
| A-012 | 0 | H | — | OiPr |
| A-013 | 0 | H | — | vinyl |
| A-014 | 0 | H | — | ethynyl |
| A-015 | 0 | H | — | CN |
| A-016 | 0 | H | — | $CF_3$ |
| A-017 | 0 | H | — | $OCF_3$ |
| A-018 | 0 | H | — | $CHF_2$ |
| A-019 | 0 | H | — | $CH_2F$ |
| A-020 | 0 | H | — | $OCHF_2$ |
| A-021 | 0 | H | — | $OCH_2F$ |
| A-022 | 1 | H | H | — |
| A-023 | 1 | H | H | F |
| A-024 | 1 | H | H | Cl |
| A-025 | 1 | H | H | Br |
| A-026 | 1 | H | H | Me |
| A-027 | 1 | H | H | Et |
| A-028 | 1 | H | H | iPr |
| A-029 | 1 | H | H | cPr |
| A-030 | 1 | H | H | tBu |
| A-031 | 1 | H | H | OMe |
| A-032 | 1 | H | H | OEt |
| A-033 | 1 | H | H | OiPr |
| A-034 | 1 | H | H | vinyl |
| A-035 | 1 | H | H | ethynyl |
| A-036 | 1 | H | H | CN |
| A-037 | 1 | H | H | $CF_3$ |
| A-038 | 1 | H | H | $OCF_3$ |
| A-039 | 1 | H | H | $CHF_2$ |
| A-040 | 1 | H | H | $CH_2F$ |
| A-041 | 1 | H | H | $OCHF_2$ |
| A-042 | 1 | H | H | $OCH_2F$ |
| A-043 | 0 | Me | — | — |
| A-044 | 0 | Me | — | F |
| A-045 | 0 | Me | — | Cl |
| A-046 | 0 | Me | — | Br |
| A-047 | 0 | Me | — | Me |
| A-048 | 0 | Me | — | Et |
| A-049 | 0 | Me | — | iPr |
| A-050 | 0 | Me | — | cPr |
| A-051 | 0 | Me | — | tBu |
| A-052 | 0 | Me | — | OMe |
| A-053 | 0 | Me | — | OEt |
| A-054 | 0 | Me | — | OiPr |

TABLE A-continued

| No. | p | R¹ | R³ | R⁵ |
|---|---|---|---|---|
| A-055 | 0 | Me | — | vinyl |
| A-056 | 0 | Me | — | ethynyl |
| A-057 | 0 | Me | — | CN |
| A-058 | 0 | Me | — | CF₃ |
| A-059 | 0 | Me | — | OCF₃ |
| A-060 | 0 | Me | — | CHF₂ |
| A-061 | 0 | Me | — | CH₂F |
| A-062 | 0 | Me | — | OCHF₂ |
| A-063 | 0 | Me | — | OCH₂F |
| A-064 | 0 | Et | — | — |
| A-065 | 0 | Et | — | F |
| A-066 | 0 | Et | — | Cl |
| A-067 | 0 | Et | — | Br |
| A-068 | 0 | Et | — | Me |
| A-069 | 0 | Et | — | Et |
| A-070 | 0 | Et | — | iPr |
| A-071 | 0 | Et | — | cPr |
| A-072 | 0 | Et | — | tBu |
| A-073 | 0 | Et | — | OMe |
| A-074 | 0 | Et | — | OEt |
| A-075 | 0 | Et | — | OiPr |
| A-076 | 0 | Et | — | vinyl |
| A-077 | 0 | Et | — | ethynyl |
| A-078 | 0 | Et | — | CN |
| A-079 | 0 | Et | — | CF₃ |
| A-080 | 0 | Et | — | OCF₃ |
| A-081 | 0 | Et | — | CHF₂ |
| A-082 | 0 | Et | — | CH₂F |
| A-083 | 0 | Et | — | OCHF₂ |
| A-084 | 0 | Et | — | OCH₂F |
| A-085 | 0 | CN | — | — |
| A-086 | 0 | CN | — | F |
| A-087 | 0 | CN | — | Cl |
| A-088 | 0 | CN | — | Br |
| A-089 | 0 | CN | — | Me |
| A-090 | 0 | CN | — | Et |
| A-091 | 0 | CN | — | iPr |
| A-092 | 0 | CN | — | cPr |
| A-093 | 0 | CN | — | tBu |
| A-094 | 0 | CN | — | OMe |
| A-095 | 0 | CN | — | OEt |
| A-096 | 0 | CN | — | OiPr |
| A-097 | 0 | CN | — | vinyl |
| A-098 | 0 | CN | — | ethynyl |
| A-099 | 0 | CN | — | CN |
| A-100 | 0 | CN | — | CF₃ |
| A-101 | 0 | CN | — | OCF₃ |
| A-102 | 0 | CN | — | CHF₂ |
| A-103 | 0 | CN | — | CH₂F |
| A-104 | 0 | CN | — | OCHF₂ |
| A-105 | 0 | CN | — | OCH₂F |
| A-106 | 0 | CF₃ | — | — |
| A-107 | 0 | CF₃ | — | F |
| A-108 | 0 | CF₃ | — | Cl |
| A-109 | 0 | CF₃ | — | Br |
| A-110 | 0 | CF₃ | — | Me |
| A-111 | 0 | CF₃ | — | Et |
| A-112 | 0 | CF₃ | — | iPr |
| A-113 | 0 | CF₃ | — | cPr |
| A-114 | 0 | CF₃ | — | tBu |
| A-115 | 0 | CF₃ | — | OMe |
| A-116 | 0 | CF₃ | — | OEt |
| A-117 | 0 | CF₃ | — | OiPr |
| A-118 | 0 | CF₃ | — | vinyl |
| A-119 | 0 | CF₃ | — | ethynyl |
| A-120 | 0 | CF₃ | — | CN |
| A-121 | 0 | CF₃ | — | CF₃ |
| A-122 | 0 | CF₃ | — | OCF₃ |
| A-123 | 0 | CF₃ | — | CHF₂ |
| A-124 | 0 | CF₃ | — | CH₂F |
| A-125 | 0 | CF₃ | — | OCHF₂ |
| A-126 | 0 | CF₃ | — | OCH₂F |
| A-127 | 0 | CH₂CN | — | — |
| A-128 | 0 | CH₂CN | — | F |
| A-129 | 0 | CH₂CN | — | Cl |
| A-130 | 0 | CH₂CN | — | Br |
| A-131 | 0 | CH₂CN | — | Me |
| A-132 | 0 | CH₂CN | — | Et |
| A-133 | 0 | CH₂CN | — | iPr |
| A-134 | 0 | CH₂CN | — | cPr |
| A-135 | 0 | CH₂CN | — | tBu |
| A-136 | 0 | CH₂CN | — | OMe |
| A-137 | 0 | CH₂CN | — | OEt |
| A-138 | 0 | CH₂CN | — | OiPr |
| A-139 | 0 | CH₂CN | — | vinyl |
| A-140 | 0 | CH₂CN | — | ethynyl |
| A-141 | 0 | CH₂CN | — | CN |
| A-142 | 0 | CH₂CN | — | CF₃ |
| A-143 | 0 | CH₂CN | — | OCF₃ |
| A-144 | 0 | CH₂CN | — | CHF₂ |
| A-145 | 0 | CH₂CN | — | CH₂F |
| A-146 | 0 | CH₂CN | — | OCHF₂ |
| A-147 | 0 | CH₂CN | — | OCH₂F |
| A-148 | 0 | CH₂OMe | — | — |
| A-149 | 0 | CH₂OMe | — | F |
| A-150 | 0 | CH₂OMe | — | Cl |
| A-151 | 0 | CH₂OMe | — | Br |
| A-152 | 0 | CH₂OMe | — | Me |
| A-153 | 0 | CH₂OMe | — | Et |
| A-154 | 0 | CH₂OMe | — | iPr |
| A-155 | 0 | CH₂OMe | — | cPr |
| A-156 | 0 | CH₂OMe | — | tBu |
| A-157 | 0 | CH₂OMe | — | OMe |
| A-158 | 0 | CH₂OMe | — | OEt |
| A-159 | 0 | CH₂OMe | — | OiPr |
| A-160 | 0 | CH₂OMe | — | vinyl |
| A-161 | 0 | CH₂OMe | — | ethynyl |
| A-162 | 0 | CH₂OMe | — | CN |
| A-163 | 0 | CH₂OMe | — | CF₃ |
| A-164 | 0 | CH₂OMe | — | OCF₃ |
| A-165 | 0 | CH₂OMe | — | CHF₂ |
| A-166 | 0 | CH₂OMe | — | CH₂F |
| A-167 | 0 | CH₂OMe | — | OCHF₂ |
| A-168 | 0 | CH₂OMe | — | OCH₂F |
| A-169 | 1 | Me | H | — |
| A-170 | 1 | Me | H | F |
| A-171 | 1 | Me | H | Cl |
| A-172 | 1 | Me | H | Br |
| A-173 | 1 | Me | H | Me |
| A-174 | 1 | Me | H | Et |
| A-175 | 1 | Me | H | iPr |
| A-176 | 1 | Me | H | cPr |
| A-177 | 1 | Me | H | tBu |
| A-178 | 1 | Me | H | OMe |
| A-179 | 1 | Me | H | OEt |
| A-180 | 1 | Me | H | OiPr |
| A-181 | 1 | Me | H | vinyl |
| A-182 | 1 | Me | H | ethynyl |
| A-183 | 1 | Me | H | CN |
| A-184 | 1 | Me | H | CF₃ |
| A-185 | 1 | Me | H | OCF₃ |
| A-186 | 1 | Me | H | CHF₂ |
| A-187 | 1 | Me | H | CH₂F |
| A-188 | 1 | Me | H | OCHF₂ |
| A-189 | 1 | Me | H | OCH₂F |
| A-190 | 1 | Et | H | — |
| A-191 | 1 | Et | H | F |
| A-192 | 1 | Et | H | Cl |
| A-193 | 1 | Et | H | Br |
| A-194 | 1 | Et | H | Me |
| A-195 | 1 | Et | H | Et |
| A-196 | 1 | Et | H | iPr |
| A-197 | 1 | Et | H | cPr |
| A-198 | 1 | Et | H | tBu |
| A-199 | 1 | Et | H | OMe |
| A-200 | 1 | Et | H | OEt |
| A-201 | 1 | Et | H | OiPr |
| A-202 | 1 | Et | H | vinyl |
| A-203 | 1 | Et | H | ethynyl |
| A-204 | 1 | Et | H | CN |
| A-205 | 1 | Et | H | CF₃ |
| A-206 | 1 | Et | H | OCF₃ |
| A-207 | 1 | Et | H | CHF₂ |
| A-208 | 1 | Et | H | CH₂F |
| A-209 | 1 | Et | H | OCHF₂ |
| A-210 | 1 | Et | H | OCH₂F |

TABLE A-continued

| No. | p | $R^1$ | $R^3$ | $R^5$ |
|---|---|---|---|---|
| A-211 | 1 | CN | H | — |
| A-212 | 1 | CN | H | F |
| A-213 | 1 | CN | H | Cl |
| A-214 | 1 | CN | H | Br |
| A-215 | 1 | CN | H | Me |
| A-216 | 1 | CN | H | Et |
| A-217 | 1 | CN | H | iPr |
| A-218 | 1 | CN | H | cPr |
| A-219 | 1 | CN | H | tBu |
| A-220 | 1 | CN | H | OMe |
| A-221 | 1 | CN | H | OEt |
| A-222 | 1 | CN | H | OiPr |
| A-223 | 1 | CN | H | vinyl |
| A-224 | 1 | CN | H | ethynyl |
| A-225 | 1 | CN | H | CN |
| A-226 | 1 | CN | H | $CF_3$ |
| A-227 | 1 | CN | H | $OCF_3$ |
| A-228 | 1 | CN | H | $CHF_2$ |
| A-229 | 1 | CN | H | $CH_2F$ |
| A-230 | 1 | CN | H | $OCHF_2$ |
| A-231 | 1 | CN | H | $OCH_2F$ |
| A-232 | 1 | $CF_3$ | H | — |
| A-233 | 1 | $CF_3$ | H | F |
| A-234 | 1 | $CF_3$ | H | Cl |
| A-235 | 1 | $CF_3$ | H | Br |
| A-236 | 1 | $CF_3$ | H | Me |
| A-237 | 1 | $CF_3$ | H | Et |
| A-238 | 1 | $CF_3$ | H | iPr |
| A-239 | 1 | $CF_3$ | H | cPr |
| A-240 | 1 | $CF_3$ | H | tBu |
| A-241 | 1 | $CF_3$ | H | OMe |
| A-242 | 1 | $CF_3$ | H | OEt |
| A-243 | 1 | $CF_3$ | H | OiPr |
| A-244 | 1 | $CF_3$ | H | vinyl |
| A-245 | 1 | $CF_3$ | H | ethynyl |
| A-246 | 1 | $CF_3$ | H | CN |
| A-247 | 1 | $CF_3$ | H | $CF_3$ |
| A-248 | 1 | $CF_3$ | H | $OCF_3$ |
| A-249 | 1 | $CF_3$ | H | $CHF_2$ |
| A-250 | 1 | $CF_3$ | H | $CH_2F$ |
| A-251 | 1 | $CF_3$ | H | $OCHF_2$ |
| A-252 | 1 | $CF_3$ | H | $OCH_2F$ |
| A-253 | 1 | $CH_2CN$ | H | — |
| A-254 | 1 | $CH_2CN$ | H | F |
| A-255 | 1 | $CH_2CN$ | H | Cl |
| A-256 | 1 | $CH_2CN$ | H | Br |
| A-257 | 1 | $CH_2CN$ | H | Me |
| A-258 | 1 | $CH_2CN$ | H | Et |
| A-259 | 1 | $CH_2CN$ | H | iPr |
| A-260 | 1 | $CH_2CN$ | H | cPr |
| A-261 | 1 | $CH_2CN$ | H | tBu |
| A-262 | 1 | $CH_2CN$ | H | OMe |
| A-263 | 1 | $CH_2CN$ | H | OEt |
| A-264 | 1 | $CH_2CN$ | H | OiPr |
| A-265 | 1 | $CH_2CN$ | H | vinyl |
| A-266 | 1 | $CH_2CN$ | H | ethynyl |
| A-267 | 1 | $CH_2CN$ | H | CN |
| A-268 | 1 | $CH_2CN$ | H | $CF_3$ |
| A-269 | 1 | $CH_2CN$ | H | $OCF_3$ |
| A-270 | 1 | $CH_2CN$ | H | $CHF_2$ |
| A-271 | 1 | $CH_2CN$ | H | $CH_2F$ |
| A-272 | 1 | $CH_2CN$ | H | $OCHF_2$ |
| A-273 | 1 | $CH_2CN$ | H | $OCH_2F$ |
| A-274 | 1 | $CH_2OMe$ | H | — |
| A-275 | 1 | $CH_2OMe$ | H | F |
| A-276 | 1 | $CH_2OMe$ | H | Cl |
| A-277 | 1 | $CH_2OMe$ | H | Br |
| A-278 | 1 | $CH_2OMe$ | H | Me |
| A-279 | 1 | $CH_2OMe$ | H | Et |
| A-280 | 1 | $CH_2OMe$ | H | iPr |
| A-281 | 1 | $CH_2OMe$ | H | cPr |
| A-282 | 1 | $CH_2OMe$ | H | tBu |
| A-283 | 1 | $CH_2OMe$ | H | OMe |
| A-284 | 1 | $CH_2OMe$ | H | OEt |
| A-285 | 1 | $CH_2OMe$ | H | OiPr |
| A-286 | 1 | $CH_2OMe$ | H | vinyl |
| A-287 | 1 | $CH_2OMe$ | H | ethynyl |
| A-288 | 1 | $CH_2OMe$ | H | CN |
| A-289 | 1 | $CH_2OMe$ | H | $CF_3$ |
| A-290 | 1 | $CH_2OMe$ | H | $OCF_3$ |
| A-291 | 1 | $CH_2OMe$ | H | $CHF_2$ |
| A-292 | 1 | $CH_2OMe$ | H | $CH_2F$ |
| A-293 | 1 | $CH_2OMe$ | H | $OCHF_2$ |
| A-294 | 1 | $CH_2OMe$ | H | $OCH_2F$ |
| A-295 | 1 | H | Me | — |
| A-296 | 1 | H | Me | F |
| A-297 | 1 | H | Me | Cl |
| A-298 | 1 | H | Me | Br |
| A-299 | 1 | H | Me | Me |
| A-300 | 1 | H | Me | Et |
| A-301 | 1 | H | Me | iPr |
| A-302 | 1 | H | Me | cPr |
| A-303 | 1 | H | Me | tBu |
| A-304 | 1 | H | Me | OMe |
| A-305 | 1 | H | Me | OEt |
| A-306 | 1 | H | Me | OiPr |
| A-307 | 1 | H | Me | vinyl |
| A-308 | 1 | H | Me | ethynyl |
| A-309 | 1 | H | Me | CN |
| A-310 | 1 | H | Me | $CF_3$ |
| A-311 | 1 | H | Me | $OCF_3$ |
| A-312 | 1 | H | Me | $CHF_2$ |
| A-313 | 1 | H | Me | $CH_2F$ |
| A-314 | 1 | H | Me | $OCHF_2$ |
| A-315 | 1 | H | Me | $OCH_2F$ |
| A-316 | 1 | H | Et | — |
| A-317 | 1 | H | Et | F |
| A-318 | 1 | H | Et | Cl |
| A-319 | 1 | H | Et | Br |
| A-320 | 1 | H | Et | Me |
| A-321 | 1 | H | Et | Et |
| A-322 | 1 | H | Et | iPr |
| A-323 | 1 | H | Et | cPr |
| A-324 | 1 | H | Et | tBu |
| A-325 | 1 | H | Et | OMe |
| A-326 | 1 | H | Et | OEt |
| A-327 | 1 | H | Et | OiPr |
| A-328 | 1 | H | Et | vinyl |
| A-329 | 1 | H | Et | ethynyl |
| A-330 | 1 | H | Et | CN |
| A-331 | 1 | H | Et | $CF_3$ |
| A-332 | 1 | H | Et | $OCF_3$ |
| A-333 | 1 | H | Et | $CHF_2$ |
| A-334 | 1 | H | Et | $CH_2F$ |
| A-335 | 1 | H | Et | $OCHF_2$ |
| A-336 | 1 | H | Et | $OCH_2F$ |
| A-337 | 1 | H | CN | H |
| A-338 | 1 | H | CN | F |
| A-339 | 1 | H | CN | Cl |
| A-340 | 1 | H | CN | Br |
| A-341 | 1 | H | CN | Me |
| A-342 | 1 | H | CN | Et |
| A-343 | 1 | H | CN | iPr |
| A-344 | 1 | H | CN | cPr |
| A-345 | 1 | H | CN | tBu |
| A-346 | 1 | H | CN | OMe |
| A-347 | 1 | H | CN | OEt |
| A-348 | 1 | H | CN | OiPr |
| A-349 | 1 | H | CN | vinyl |
| A-350 | 1 | H | CN | ethynyl |
| A-351 | 1 | H | CN | CN |
| A-352 | 1 | H | CN | $CF_3$ |
| A-353 | 1 | H | CN | $OCF_3$ |
| A-354 | 1 | H | CN | $CHF_2$ |
| A-355 | 1 | H | CN | $CH_2F$ |
| A-356 | 1 | H | CN | $OCHF_2$ |
| A-357 | 1 | H | CN | $OCH_2F$ |
| A-358 | 1 | H | $CF_3$ | — |
| A-359 | 1 | H | $CF_3$ | F |
| A-360 | 1 | H | $CF_3$ | Cl |
| A-361 | 1 | H | $CF_3$ | Br |
| A-362 | 1 | H | $CF_3$ | Me |
| A-363 | 1 | H | $CF_3$ | Et |
| A-364 | 1 | H | $CF_3$ | iPr |
| A-365 | 1 | H | $CF_3$ | cPr |
| A-366 | 1 | H | $CF_3$ | tBu |

TABLE A-continued

| No. | p | R$^1$ | R$^3$ | R$^5$ |
|---|---|---|---|---|
| A-367 | 1 | H | CF$_3$ | OMe |
| A-368 | 1 | H | CF$_3$ | OEt |
| A-369 | 1 | H | CF$_3$ | OiPr |
| A-370 | 1 | H | CF$_3$ | vinyl |
| A-371 | 1 | H | CF$_3$ | ethynyl |
| A-372 | 1 | H | CF$_3$ | CN |
| A-373 | 1 | H | CF$_3$ | CF$_3$ |
| A-374 | 1 | H | CF$_3$ | OCF$_3$ |
| A-375 | 1 | H | CF$_3$ | CHF$_2$ |
| A-376 | 1 | H | CF$_3$ | CH$_2$F |
| A-377 | 1 | H | CF$_3$ | OCHF$_2$ |
| A-378 | 1 | H | CF$_3$ | OCH$_2$F |
| A-379 | 1 | H | CH$_2$CN | — |
| A-380 | 1 | H | CH$_2$CN | F |
| A-381 | 1 | H | CH$_2$CN | Cl |
| A-382 | 1 | H | CH$_2$CN | Br |
| A-383 | 1 | H | CH$_2$CN | Me |
| A-384 | 1 | H | CH$_2$CN | Et |
| A-385 | 1 | H | CH$_2$CN | iPr |
| A-386 | 1 | H | CH$_2$CN | cPr |
| A-387 | 1 | H | CH$_2$CN | tBu |
| A-388 | 1 | H | CH$_2$CN | OMe |
| A-389 | 1 | H | CH$_2$CN | OEt |
| A-390 | 1 | H | CH$_2$CN | OiPr |
| A-391 | 1 | H | CH$_2$CN | vinyl |
| A-392 | 1 | H | CH$_2$CN | ethynyl |
| A-393 | 1 | H | CH$_2$CN | CN |
| A-394 | 1 | H | CH$_2$CN | CF$_3$ |
| A-395 | 1 | H | CH$_2$CN | OCF$_3$ |
| A-396 | 1 | H | CH$_2$CN | CHF$_2$ |
| A-397 | 1 | H | CH$_2$CN | CH$_2$F |
| A-398 | 1 | H | CH$_2$CN | OCHF$_2$ |
| A-399 | 1 | H | CH$_2$CN | OCH$_2$F |
| A-400 | 1 | H | CH$_2$OMe | — |
| A-401 | 1 | H | CH$_2$OMe | F |
| A-402 | 1 | H | CH$_2$OMe | Cl |
| A-403 | 1 | H | CH$_2$OMe | Br |
| A-404 | 1 | H | CH$_2$OMe | Me |
| A-405 | 1 | H | CH$_2$OMe | Et |
| A-406 | 1 | H | CH$_2$OMe | iPr |
| A-407 | 1 | H | CH$_2$OMe | cPr |
| A-408 | 1 | H | CH$_2$OMe | tBu |
| A-409 | 1 | H | CH$_2$OMe | OMe |
| A-410 | 1 | H | CH$_2$OMe | OEt |
| A-411 | 1 | H | CH$_2$OMe | OiPr |
| A-412 | 1 | H | CH$_2$OMe | vinyl |
| A-413 | 1 | H | CH$_2$OMe | ethynyl |
| A-414 | 1 | H | CH$_2$OMe | CN |
| A-415 | 1 | H | CH$_2$OMe | CF$_3$ |
| A-416 | 1 | H | CH$_2$OMe | OCF$_3$ |
| A-417 | 1 | H | CH$_2$OMe | CHF$_2$ |
| A-418 | 1 | H | CH$_2$OMe | CH$_2$F |
| A-419 | 1 | H | CH$_2$OMe | OCHF$_2$ |
| A-420 | 1 | H | CH$_2$OMe | OCH$_2$F |

Further preferred compounds of formula (I) are compounds of formulae (Ib-1), (Ib-2), (Ib-3), (Ib-4), (Ib-5) or (Ib-6),

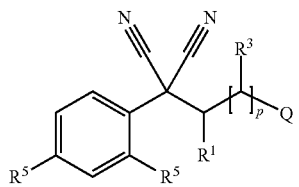
(Ib-1)

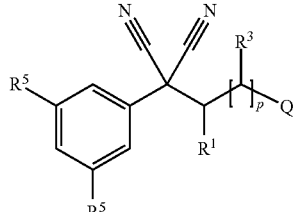
(Ib-2)

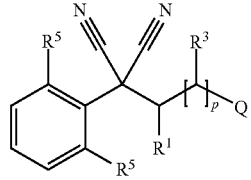
(Ib-3)

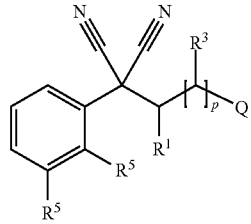
(Ib-4)

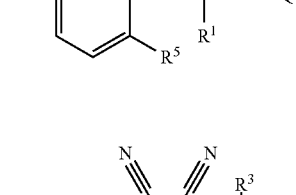
(Ib-5)

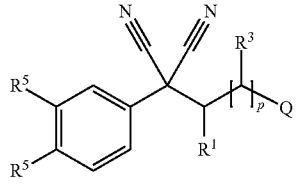
(Ib-6)

wherein Y is phenyl substituted with 2 substituents R$^5$; R$^2$ is H; R$^4$ is H; Q is as defined in formula (I); and p, R$^1$, R$^3$ and R$^5$ are as defined in Table B.

Further preferred compounds of formula (I) are compounds of formulae (Ib-7), (Ib-8), (Ib-9), (Ib-10), (Ib-11) or (Ib-12),

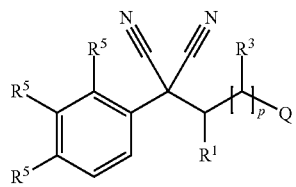
(Ib-7)

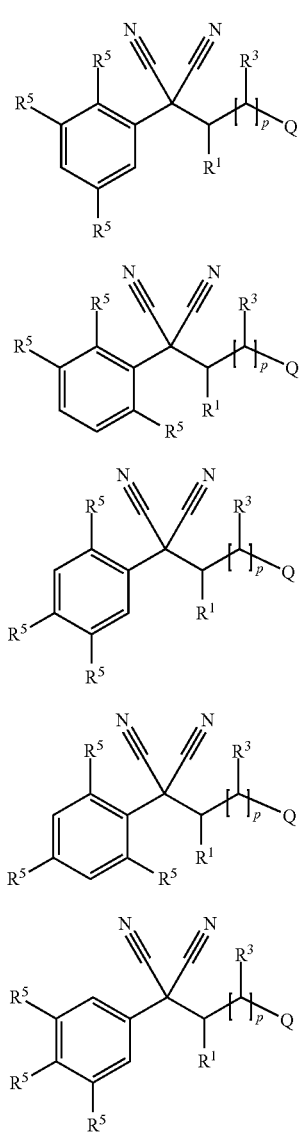

(Ib-8), (Ib-9), (Ib-10), (Ib-11), (Ib-12)

wherein Y is phenyl substituted with 3 substituents $R^5$; $R^2$ is H; $R^4$ is H; Q is as defined in formula (I); and p, $R^1$, $R^3$ and $R^5$ are as defined in Table B.

TABLE B

| No. | p | $R^1$ | $R^3$ | $R^5$ |
|---|---|---|---|---|
| B-001 | 0 | H | — | F |
| B-002 | 0 | H | — | Cl |
| B-003 | 0 | H | — | Br |
| B-004 | 0 | H | — | Me |
| B-005 | 0 | H | — | Et |
| B-006 | 0 | H | — | iPr |
| B-007 | 0 | H | — | cPr |
| B-008 | 0 | H | — | OMe |
| B-009 | 0 | H | — | OEt |
| B-010 | 0 | H | — | $CF_3$ |
| B-011 | 0 | H | — | $OCF_3$ |
| B-012 | 1 | H | H | F |
| B-013 | 1 | H | H | Cl |
| B-014 | 1 | H | H | Br |
| B-015 | 1 | H | H | Me |
| B-016 | 1 | H | H | Et |
| B-017 | 1 | H | H | iPr |
| B-018 | 1 | H | H | cPr |
| B-019 | 1 | H | H | OMe |
| B-020 | 1 | H | H | OEt |
| B-021 | 1 | H | H | $CF_3$ |
| B-022 | 1 | H | H | $OCF_3$ |
| B-023 | 0 | Me | — | F |
| B-024 | 0 | Me | — | Cl |
| B-025 | 0 | Me | — | Br |
| B-026 | 0 | Me | — | Me |
| B-027 | 0 | Me | — | Et |
| B-028 | 0 | Me | — | iPr |
| B-029 | 0 | Me | — | cPr |
| B-030 | 0 | Me | — | OMe |
| B-031 | 0 | Me | — | OEt |
| B-032 | 0 | Me | — | $CF_3$ |
| B-033 | 0 | Me | — | $OCF_3$ |
| B-034 | 0 | Et | — | F |
| B-035 | 0 | Et | — | Cl |
| B-036 | 0 | Et | — | Br |
| B-037 | 0 | Et | — | Me |
| B-038 | 0 | Et | — | Et |
| B-039 | 0 | Et | — | iPr |
| B-040 | 0 | Et | — | cPr |
| B-041 | 0 | Et | — | OMe |
| B-042 | 0 | Et | — | OEt |
| B-043 | 0 | Et | — | $CF_3$ |
| B-044 | 0 | Et | — | $OCF_3$ |
| B-045 | 0 | CN | — | F |
| B-046 | 0 | CN | — | Cl |
| B-047 | 0 | CN | — | Br |
| B-048 | 0 | CN | — | Me |
| B-049 | 0 | CN | — | Et |
| B-050 | 0 | CN | — | iPr |
| B-051 | 0 | CN | — | cPr |
| B-052 | 0 | CN | — | OMe |
| B-053 | 0 | CN | — | OEt |
| B-054 | 0 | CN | — | $CF_3$ |
| B-055 | 0 | CN | — | $OCF_3$ |
| B-056 | 0 | $CF_3$ | — | F |
| B-057 | 0 | $CF_3$ | — | Cl |
| B-058 | 0 | $CF_3$ | — | Br |
| B-059 | 0 | $CF_3$ | — | Me |
| B-060 | 0 | $CF_3$ | — | Et |
| B-061 | 0 | $CF_3$ | — | iPr |
| B-062 | 0 | $CF_3$ | — | cPr |
| B-063 | 0 | $CF_3$ | — | OMe |
| B-064 | 0 | $CF_3$ | — | OEt |
| B-065 | 0 | $CF_3$ | — | $CF_3$ |
| B-066 | 0 | $CF_3$ | — | $OCF_3$ |
| B-067 | 0 | $CH_2CN$ | — | F |
| B-068 | 0 | $CH_2CN$ | — | Cl |
| B-069 | 0 | $CH_2CN$ | — | Br |
| B-070 | 0 | $CH_2CN$ | — | Me |
| B-071 | 0 | $CH_2CN$ | — | Et |
| B-072 | 0 | $CH_2CN$ | — | iPr |
| B-073 | 0 | $CH_2CN$ | — | cPr |
| B-074 | 0 | $CH_2CN$ | — | OMe |
| B-075 | 0 | $CH_2CN$ | — | OEt |
| B-076 | 0 | $CH_2CN$ | — | $CF_3$ |
| B-077 | 0 | $CH_2CN$ | — | $OCF_3$ |
| B-078 | 0 | $CH_2OMe$ | — | F |
| B-079 | 0 | $CH_2OMe$ | — | Cl |
| B-080 | 0 | $CH_2OMe$ | — | Br |
| B-081 | 0 | $CH_2OMe$ | — | Me |
| B-082 | 0 | $CH_2OMe$ | — | Et |
| B-083 | 0 | $CH_2OMe$ | — | iPr |
| B-084 | 0 | $CH_2OMe$ | — | cPr |
| B-085 | 0 | $CH_2OMe$ | — | OMe |
| B-086 | 0 | $CH_2OMe$ | — | OEt |
| B-087 | 0 | $CH_2OMe$ | — | $CF_3$ |
| B-088 | 0 | $CH_2OMe$ | — | $OCF_3$ |
| B-089 | 1 | Me | H | F |
| B-090 | 1 | Me | H | Cl |
| B-091 | 1 | Me | H | Br |
| B-092 | 1 | Me | H | Me |
| B-093 | 1 | Me | H | Et |
| B-094 | 1 | Me | H | iPr |

TABLE B-continued

| No. | p | R¹ | R³ | R⁵ |
|---|---|---|---|---|
| B-095 | 1 | Me | H | cPr |
| B-096 | 1 | Me | H | OMe |
| B-097 | 1 | Me | H | OEt |
| B-098 | 1 | Me | H | $CF_3$ |
| B-099 | 1 | Me | H | $OCF_3$ |
| B-100 | 1 | Et | H | F |
| B-101 | 1 | Et | H | Cl |
| B-102 | 1 | Et | H | Br |
| B-103 | 1 | Et | H | Me |
| B-104 | 1 | Et | H | Et |
| B-105 | 1 | Et | H | iPr |
| B-106 | 1 | Et | H | cPr |
| B-107 | 1 | Et | H | OMe |
| B-108 | 1 | Et | H | OEt |
| B-109 | 1 | Et | H | $CF_3$ |
| B-110 | 1 | Et | H | $OCF_3$ |
| B-111 | 1 | CN | H | F |
| B-112 | 1 | CN | H | Cl |
| B-113 | 1 | CN | H | Br |
| B-114 | 1 | CN | H | Me |
| B-115 | 1 | CN | H | Et |
| B-116 | 1 | CN | H | iPr |
| B-117 | 1 | CN | H | cPr |
| B-118 | 1 | CN | H | OMe |
| B-119 | 1 | CN | H | OEt |
| B-120 | 1 | CN | H | $CF_3$ |
| B-121 | 1 | CN | H | $OCF_3$ |
| B-122 | 1 | $CF_3$ | H | F |
| B-123 | 1 | $CF_3$ | H | Cl |
| B-124 | 1 | $CF_3$ | H | Br |
| B-125 | 1 | $CF_3$ | H | Me |
| B-126 | 1 | $CF_3$ | H | Et |
| B-127 | 1 | $CF_3$ | H | iPr |
| B-128 | 1 | $CF_3$ | H | cPr |
| B-129 | 1 | $CF_3$ | H | OMe |
| B-130 | 1 | $CF_3$ | H | OEt |
| B-131 | 1 | $CF_3$ | H | $CF_3$ |
| B-132 | 1 | $CF_3$ | H | $OCF_3$ |
| B-133 | 1 | $CH_2CN$ | H | F |
| B-134 | 1 | $CH_2CN$ | H | Cl |
| B-135 | 1 | $CH_2CN$ | H | Br |
| B-136 | 1 | $CH_2CN$ | H | Me |
| B-137 | 1 | $CH_2CN$ | H | Et |
| B-138 | 1 | $CH_2CN$ | H | iPr |
| B-139 | 1 | $CH_2CN$ | H | cPr |
| B-140 | 1 | $CH_2CN$ | H | OMe |
| B-141 | 1 | $CH_2CN$ | H | OEt |
| B-142 | 1 | $CH_2CN$ | H | $CF_3$ |
| B-143 | 1 | $CH_2CN$ | H | $OCF_3$ |
| B-144 | 1 | $CH_2OMe$ | H | F |
| B-145 | 1 | $CH_2OMe$ | H | Cl |
| B-146 | 1 | $CH_2OMe$ | H | Br |
| B-147 | 1 | $CH_2OMe$ | H | Me |
| B-148 | 1 | $CH_2OMe$ | H | Et |
| B-149 | 1 | $CH_2OMe$ | H | iPr |
| B-150 | 1 | $CH_2OMe$ | H | cPr |
| B-151 | 1 | $CH_2OMe$ | H | OMe |
| B-152 | 1 | $CH_2OMe$ | H | OEt |
| B-153 | 1 | $CH_2OMe$ | H | $CF_3$ |
| B-154 | 1 | $CH_2OMe$ | H | $OCF_3$ |
| B-155 | 1 | H | Me | F |
| B-156 | 1 | H | Me | Cl |
| B-157 | 1 | H | Me | Br |
| B-158 | 1 | H | Me | Me |
| B-159 | 1 | H | Me | Et |
| B-160 | 1 | H | Me | iPr |
| B-161 | 1 | H | Me | cPr |
| B-162 | 1 | H | Me | OMe |
| B-163 | 1 | H | Me | OEt |
| B-164 | 1 | H | Me | $CF_3$ |
| B-165 | 1 | H | Me | $OCF_3$ |
| B-166 | 1 | H | Et | F |
| B-167 | 1 | H | Et | Cl |
| B-168 | 1 | H | Et | Br |
| B-169 | 1 | H | Et | Me |
| B-170 | 1 | H | Et | Et |
| B-171 | 1 | H | Et | iPr |
| B-172 | 1 | H | Et | cPr |
| B-173 | 1 | H | Et | OMe |
| B-174 | 1 | H | Et | OEt |
| B-175 | 1 | H | Et | $CF_3$ |
| B-176 | 1 | H | Et | $OCF_3$ |
| B-177 | 1 | H | CN | F |
| B-178 | 1 | H | CN | Cl |
| B-179 | 1 | H | CN | Br |
| B-180 | 1 | H | CN | Me |
| B-181 | 1 | H | CN | Et |
| B-182 | 1 | H | CN | iPr |
| B-183 | 1 | H | CN | cPr |
| B-184 | 1 | H | CN | OMe |
| B-185 | 1 | H | CN | OEt |
| B-186 | 1 | H | CN | $CF_3$ |
| B-187 | 1 | H | CN | $OCF_3$ |
| B-188 | 1 | H | $CF_3$ | F |
| B-189 | 1 | H | $CF_3$ | Cl |
| B-190 | 1 | H | $CF_3$ | Br |
| B-191 | 1 | H | $CF_3$ | Me |
| B-192 | 1 | H | $CF_3$ | Et |
| B-193 | 1 | H | $CF_3$ | iPr |
| B-194 | 1 | H | $CF_3$ | cPr |
| B-195 | 1 | H | $CF_3$ | OMe |
| B-196 | 1 | H | $CF_3$ | OEt |
| B-197 | 1 | H | $CF_3$ | $CF_3$ |
| B-198 | 1 | H | $CF_3$ | $OCF_3$ |
| B-199 | 1 | H | $CH_2CN$ | F |
| B-200 | 1 | H | $CH_2CN$ | Cl |
| B-201 | 1 | H | $CH_2CN$ | Br |
| B-202 | 1 | H | $CH_2CN$ | Me |
| B-203 | 1 | H | $CH_2CN$ | Et |
| B-204 | 1 | H | $CH_2CN$ | iPr |
| B-205 | 1 | H | $CH_2CN$ | cPr |
| B-206 | 1 | H | $CH_2CN$ | OMe |
| B-207 | 1 | H | $CH_2CN$ | OEt |
| B-208 | 1 | H | $CH_2CN$ | $CF_3$ |
| B-209 | 1 | H | $CH_2CN$ | $OCF_3$ |
| B-210 | 1 | H | $CH_2OMe$ | F |
| B-211 | 1 | H | $CH_2OMe$ | Cl |
| B-212 | 1 | H | $CH_2OMe$ | Br |
| B-213 | 1 | H | $CH_2OMe$ | Me |
| B-214 | 1 | H | $CH_2OMe$ | Et |
| B-215 | 1 | H | $CH_2OMe$ | iPr |
| B-216 | 1 | H | $CH_2OMe$ | cPr |
| B-217 | 1 | H | $CH_2OMe$ | OMe |
| B-218 | 1 | H | $CH_2OMe$ | OEt |
| B-219 | 1 | H | $CH_2OMe$ | $CF_3$ |
| B-220 | 1 | H | $CH_2OMe$ | $OCF_3$ |

Further preferred compounds of formula (I) are compounds of formulae (Ic-1), (Ic-2), (Ic-3), (Ic-4), (Ic-5) (Ic-6), (Ic-7), (Ic-8) or (Ic-9),

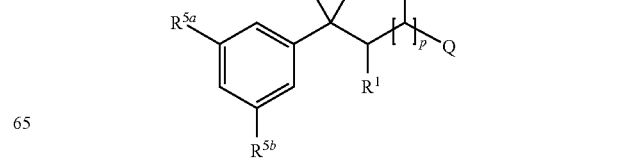

(Ic-1)

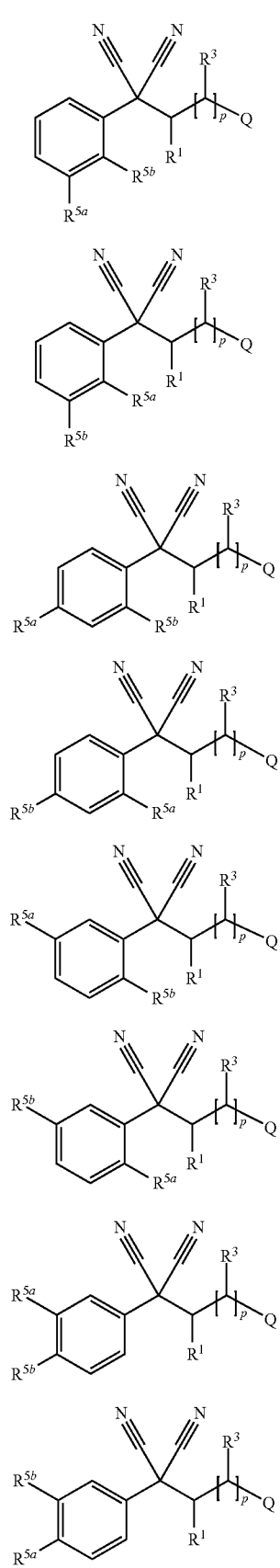

wherein Y is phenyl substituted with 2 substituents $R^5$; one $R^5$ is $R^{5a}$ and the other $R^5$ is $R^{5b}$; $R^2$ is H; $R^4$ is H; Q is as defined in formula (I); and p, $R^1$, $R^3$, $R^{5a}$ and $R^{5b}$ are as defined in Table C.

TABLE C

| No. | p | $R^1$ | $R^3$ | $R^{5a}$ | $R^{5b}$ |
|---|---|---|---|---|---|
| C-001 | 0 | H | — | F | Cl |
| C-002 | 0 | H | — | F | Me |
| C-003 | 0 | H | — | Cl | Me |
| C-004 | 0 | H | — | $CF_3$ | F |
| C-005 | 0 | H | — | $CF_3$ | Cl |
| C-006 | 0 | H | — | $CF_3$ | Me |
| C-007 | 0 | H | — | CN | F |
| C-008 | 0 | H | — | CN | Cl |
| C-009 | 0 | H | — | ethynyl | F |
| C-010 | 0 | H | — | ethynyl | Cl |
| C-011 | 0 | H | — | ethynyl | Me |
| C-012 | 0 | H | — | ethynyl | $CF_3$ |
| C-013 | 0 | H | — | $OCF_3$ | F |
| C-014 | 0 | H | — | $OCF_3$ | Cl |
| C-015 | 0 | H | — | $OCF_3$ | Me |
| C-016 | 0 | H | — | $OCF_3$ | ethynyl |
| C-017 | 1 | H | H | F | Cl |
| C-018 | 1 | H | H | F | Me |
| C-019 | 1 | H | H | Cl | Me |
| C-020 | 1 | H | H | $CF_3$ | F |
| C-021 | 1 | H | H | $CF_3$ | Cl |
| C-022 | 1 | H | H | $CF_3$ | Me |
| C-023 | 1 | H | H | CN | F |
| C-024 | 1 | H | H | CN | Cl |
| C-025 | 1 | H | H | ethynyl | F |
| C-026 | 1 | H | H | ethynyl | Cl |
| C-027 | 1 | H | H | ethynyl | Me |
| C-028 | 1 | H | H | ethynyl | $CF_3$ |
| C-029 | 1 | H | H | $OCF_3$ | F |
| C-030 | 1 | H | H | $OCF_3$ | Cl |
| C-031 | 1 | H | H | $OCF_3$ | Me |
| C-032 | 1 | H | H | $OCF_3$ | ethynyl |
| C-033 | 0 | Me | — | F | Cl |
| C-034 | 0 | Me | — | F | Me |
| C-035 | 0 | Me | — | Cl | Me |
| C-036 | 0 | Me | — | $CF_3$ | F |
| C-037 | 0 | Me | — | $CF_3$ | Cl |
| C-038 | 0 | Me | — | $CF_3$ | Me |
| C-039 | 0 | Me | — | CN | F |
| C-040 | 0 | Me | — | CN | Cl |
| C-041 | 0 | Me | — | ethynyl | F |
| C-042 | 0 | Me | — | ethynyl | Cl |
| C-043 | 0 | Me | — | ethynyl | Me |
| C-044 | 0 | Me | — | ethynyl | $CF_3$ |
| C-045 | 0 | Me | — | $OCF_3$ | F |
| C-046 | 0 | Me | — | $OCF_3$ | Cl |
| C-047 | 0 | Me | — | $OCF_3$ | Me |
| C-048 | 0 | Me | — | $OCF_3$ | ethynyl |
| C-049 | 0 | Et | — | F | Cl |
| C-050 | 0 | Et | — | F | Me |
| C-051 | 0 | Et | — | Cl | Me |
| C-052 | 0 | Et | — | $CF_3$ | F |
| C-053 | 0 | Et | — | $CF_3$ | Cl |
| C-054 | 0 | Et | — | $CF_3$ | Me |
| C-055 | 0 | Et | — | CN | F |
| C-056 | 0 | Et | — | CN | Cl |
| C-057 | 0 | Et | — | CN | Me |
| C-058 | 0 | Et | — | ethynyl | F |
| C-059 | 0 | Et | — | ethynyl | Cl |
| C-060 | 0 | Et | — | ethynyl | Me |
| C-061 | 0 | Et | — | ethynyl | $CF_3$ |
| C-062 | 0 | Et | — | $OCF_3$ | F |
| C-063 | 0 | Et | — | $OCF_3$ | Cl |
| C-064 | 0 | Et | — | $OCF_3$ | Me |
| C-065 | 0 | Et | — | $OCF_3$ | ethynyl |
| C-066 | 0 | CN | — | F | Cl |
| C-067 | 0 | CN | — | F | Me |
| C-068 | 0 | CN | — | Cl | Me |
| C-069 | 0 | CN | — | $CF_3$ | F |
| C-070 | 0 | CN | — | $CF_3$ | Cl |
| C-071 | 0 | CN | — | $CF_3$ | Me |
| C-072 | 0 | CN | — | CN | F |

TABLE C-continued

| No. | p | R$^1$ | R$^3$ | R$^{5a}$ | R$^{5b}$ |
|---|---|---|---|---|---|
| C-073 | 0 | CN | — | CN | Cl |
| C-074 | 0 | CN | — | ethynyl | F |
| C-075 | 0 | CN | — | ethynyl | Cl |
| C-076 | 0 | CN | — | ethynyl | Me |
| C-077 | 0 | CN | — | ethynyl | CF$_3$ |
| C-078 | 0 | CN | — | OCF$_3$ | F |
| C-079 | 0 | CN | — | OCF$_3$ | Cl |
| C-080 | 0 | CN | — | OCF$_3$ | Me |
| C-081 | 0 | CN | — | OCF$_3$ | ethynyl |
| C-082 | 0 | CF$_3$ | — | F | Cl |
| C-083 | 0 | CF$_3$ | — | F | Me |
| C-084 | 0 | CF$_3$ | — | Cl | Me |
| C-085 | 0 | CF$_3$ | — | CF$_3$ | F |
| C-086 | 0 | CF$_3$ | — | CF$_3$ | Cl |
| C-087 | 0 | CF$_3$ | — | CF$_3$ | Me |
| C-088 | 0 | CF$_3$ | — | CN | F |
| C-089 | 0 | CF$_3$ | — | CN | Cl |
| C-090 | 0 | CF$_3$ | — | ethynyl | F |
| C-091 | 0 | CF$_3$ | — | ethynyl | Cl |
| C-092 | 0 | CF$_3$ | — | ethynyl | Me |
| C-093 | 0 | CF$_3$ | — | ethynyl | CF$_3$ |
| C-094 | 0 | CF$_3$ | — | OCF$_3$ | F |
| C-095 | 0 | CF$_3$ | — | OCF$_3$ | Cl |
| C-096 | 0 | CF$_3$ | — | OCF$_3$ | Me |
| C-097 | 0 | CF$_3$ | — | OCF$_3$ | ethynyl |
| C-098 | 0 | CH$_2$CN | — | F | Cl |
| C-099 | 0 | CH$_2$CN | — | F | Me |
| C-100 | 0 | CH$_2$CN | — | Cl | Me |
| C-101 | 0 | CH$_2$CN | — | CF$_3$ | F |
| C-102 | 0 | CH$_2$CN | — | CF$_3$ | Cl |
| C-103 | 0 | CH$_2$CN | — | CF$_3$ | Me |
| C-104 | 0 | CH$_2$CN | — | CN | F |
| C-105 | 0 | CH$_2$CN | — | CN | Cl |
| C-106 | 0 | CH$_2$CN | — | ethynyl | F |
| C-107 | 0 | CH$_2$CN | — | ethynyl | Cl |
| C-108 | 0 | CH$_2$CN | — | ethynyl | Me |
| C-109 | 0 | CH$_2$CN | — | ethynyl | CF$_3$ |
| C-110 | 0 | CH$_2$CN | — | OCF$_3$ | F |
| C-111 | 0 | CH$_2$CN | — | OCF$_3$ | Cl |
| C-112 | 0 | CH$_2$CN | — | OCF$_3$ | Me |
| C-113 | 0 | CH$_2$CN | — | OCF$_3$ | ethynyl |
| C-114 | 0 | CH$_2$OMe | — | F | Cl |
| C-115 | 0 | CH$_2$OMe | — | F | Me |
| C-116 | 0 | CH$_2$OMe | — | Cl | Me |
| C-117 | 0 | CH$_2$OMe | — | CF$_3$ | F |
| C-118 | 0 | CH$_2$OMe | — | CF$_3$ | Cl |
| C-119 | 0 | CH$_2$OMe | — | CF$_3$ | Me |
| C-120 | 0 | CH$_2$OMe | — | CN | F |
| C-121 | 0 | CH$_2$OMe | — | CN | Cl |
| C-122 | 0 | CH$_2$OMe | — | ethynyl | F |
| C-123 | 0 | CH$_2$OMe | — | ethynyl | Cl |
| C-124 | 0 | CH$_2$OMe | — | ethynyl | Me |
| C-125 | 0 | CH$_2$OMe | — | ethynyl | CF$_3$ |
| C-126 | 0 | CH$_2$OMe | — | OCF$_3$ | F |
| C-127 | 0 | CH$_2$OMe | — | OCF$_3$ | Cl |
| C-128 | 0 | CH$_2$OMe | — | OCF$_3$ | Me |
| C-129 | 0 | CH$_2$OMe | — | OCF$_3$ | ethynyl |
| C-130 | 1 | Me | H | F | Cl |
| C-131 | 1 | Me | H | F | Me |
| C-132 | 1 | Me | H | Cl | Me |
| C-133 | 1 | Me | H | CF$_3$ | F |
| C-134 | 1 | Me | H | CF$_3$ | Cl |
| C-135 | 1 | Me | H | CF$_3$ | Me |
| C-136 | 1 | Me | H | CN | F |
| C-137 | 1 | Me | H | CN | Cl |
| C-138 | 1 | Me | H | ethynyl | F |
| C-139 | 1 | Me | H | ethynyl | Cl |
| C-140 | 1 | Me | H | ethynyl | Me |
| C-141 | 1 | Me | H | ethynyl | CF$_3$ |
| C-142 | 1 | Me | H | OCF$_3$ | F |
| C-143 | 1 | Me | H | OCF$_3$ | Cl |
| C-144 | 1 | Me | H | OCF$_3$ | Me |
| C-145 | 1 | Me | H | OCF$_3$ | ethynyl |
| C-146 | 1 | Et | H | F | Cl |
| C-147 | 1 | Et | H | F | Me |
| C-148 | 1 | Et | H | Cl | Me |
| C-149 | 1 | Et | H | CF$_3$ | F |
| C-150 | 1 | Et | H | CF$_3$ | Cl |
| C-151 | 1 | Et | H | CF$_3$ | Me |
| C-152 | 1 | Et | H | CN | F |
| C-153 | 1 | Et | H | CN | Cl |
| C-154 | 1 | Et | H | ethynyl | F |
| C-155 | 1 | Et | H | ethynyl | Cl |
| C-156 | 1 | Et | H | ethynyl | Me |
| C-157 | 1 | Et | H | ethynyl | CF$_3$ |
| C-158 | 1 | Et | H | OCF$_3$ | F |
| C-159 | 1 | Et | H | OCF$_3$ | Cl |
| C-160 | 1 | Et | H | OCF$_3$ | Me |
| C-161 | 1 | Et | H | OCF$_3$ | ethynyl |
| C-162 | 1 | CN | H | F | Cl |
| C-163 | 1 | CN | H | F | Me |
| C-164 | 1 | CN | H | Cl | Me |
| C-165 | 1 | CN | H | CF$_3$ | F |
| C-166 | 1 | CN | H | CF$_3$ | Cl |
| C-167 | 1 | CN | H | CF$_3$ | Me |
| C-168 | 1 | CN | H | CN | F |
| C-169 | 1 | CN | H | CN | Cl |
| C-170 | 1 | CN | H | ethynyl | F |
| C-171 | 1 | CN | H | ethynyl | Cl |
| C-172 | 1 | CN | H | ethynyl | Me |
| C-173 | 1 | CN | H | ethynyl | CF$_3$ |
| C-174 | 1 | CN | H | OCF$_3$ | F |
| C-175 | 1 | CN | H | OCF$_3$ | Cl |
| C-176 | 1 | CN | H | OCF$_3$ | Me |
| C-177 | 1 | CN | H | OCF$_3$ | ethynyl |
| C-178 | 1 | CF$_3$ | H | F | Cl |
| C-179 | 1 | CF$_3$ | H | F | Me |
| C-180 | 1 | CF$_3$ | H | Cl | Me |
| C-181 | 1 | CF$_3$ | H | CF$_3$ | F |
| C-182 | 1 | CF$_3$ | H | CF$_3$ | Cl |
| C-183 | 1 | CF$_3$ | H | CF$_3$ | Me |
| C-184 | 1 | CF$_3$ | H | CN | F |
| C-185 | 1 | CF$_3$ | H | CN | Cl |
| C-186 | 1 | CF$_3$ | H | ethynyl | F |
| C-187 | 1 | CF$_3$ | H | ethynyl | Cl |
| C-188 | 1 | CF$_3$ | H | ethynyl | Me |
| C-189 | 1 | CF$_3$ | H | ethynyl | CF$_3$ |
| C-190 | 1 | CF$_3$ | H | OCF$_3$ | F |
| C-191 | 1 | CF$_3$ | H | OCF$_3$ | Cl |
| C-192 | 1 | CF$_3$ | H | OCF$_3$ | Me |
| C-193 | 1 | CF$_3$ | H | OCF$_3$ | ethynyl |
| C-194 | 1 | CH$_2$CN | H | F | Cl |
| C-195 | 1 | CH$_2$CN | H | F | Me |
| C-196 | 1 | CH$_2$CN | H | Cl | Me |
| C-197 | 1 | CH$_2$CN | H | CF$_3$ | F |
| C-198 | 1 | CH$_2$CN | H | CF$_3$ | Cl |
| C-199 | 1 | CH$_2$CN | H | CF$_3$ | Me |
| C-200 | 1 | CH$_2$CN | H | CN | F |
| C-201 | 1 | CH$_2$CN | H | CN | Cl |
| C-202 | 1 | CH$_2$CN | H | ethynyl | F |
| C-203 | 1 | CH$_2$CN | H | ethynyl | Cl |
| C-204 | 1 | CH$_2$CN | H | ethynyl | Me |
| C-205 | 1 | CH$_2$CN | H | ethynyl | CF$_3$ |
| C-206 | 1 | CH$_2$CN | H | OCF$_3$ | F |
| C-207 | 1 | CH$_2$CN | H | OCF$_3$ | Cl |
| C-208 | 1 | CH$_2$CN | H | OCF$_3$ | Me |
| C-209 | 1 | CH$_2$CN | H | OCF$_3$ | ethynyl |
| C-210 | 1 | CH$_2$OMe | H | F | Cl |
| C-211 | 1 | CH$_2$OMe | H | F | Me |
| C-212 | 1 | CH$_2$OMe | H | Cl | Me |
| C-213 | 1 | CH$_2$OMe | H | CF$_3$ | F |
| C-214 | 1 | CH$_2$OMe | H | CF$_3$ | Cl |
| C-215 | 1 | CH$_2$OMe | H | CF$_3$ | Me |
| C-216 | 1 | CH$_2$OMe | H | CN | F |
| C-217 | 1 | CH$_2$OMe | H | CN | Cl |
| C-218 | 1 | CH$_2$OMe | H | ethynyl | F |
| C-219 | 1 | CH$_2$OMe | H | ethynyl | Cl |
| C-220 | 1 | CH$_2$OMe | H | ethynyl | Me |
| C-221 | 1 | CH$_2$OMe | H | ethynyl | CF$_3$ |
| C-222 | 1 | CH$_2$OMe | H | OCF$_3$ | F |
| C-223 | 1 | CH$_2$OMe | H | OCF$_3$ | Cl |
| C-224 | 1 | CH$_2$OMe | H | OCF$_3$ | Me |
| C-225 | 1 | CH$_2$OMe | H | OCF$_3$ | ethynyl |
| C-226 | 1 | H | Me | F | Cl |
| C-227 | 1 | H | Me | F | Me |
| C-228 | 1 | H | Me | Cl | Me |

TABLE C-continued

| No. | p | R¹ | R³ | R⁵ᵃ | R⁵ᵇ |
|---|---|---|---|---|---|
| C-229 | 1 | H | Me | CF₃ | F |
| C-230 | 1 | H | Me | CF₃ | Cl |
| C-231 | 1 | H | Me | CF₃ | Me |
| C-232 | 1 | H | Me | CN | F |
| C-233 | 1 | H | Me | CN | Cl |
| C-234 | 1 | H | Me | ethynyl | F |
| C-235 | 1 | H | Me | ethynyl | Cl |
| C-236 | 1 | H | Me | ethynyl | Me |
| C-237 | 1 | H | Me | ethynyl | CF₃ |
| C-238 | 1 | H | Me | OCF₃ | F |
| C-239 | 1 | H | Me | OCF₃ | Cl |
| C-240 | 1 | H | Me | OCF₃ | Me |
| C-241 | 1 | H | Me | OCF₃ | ethynyl |
| C-242 | 1 | H | Et | F | Cl |
| C-243 | 1 | H | Et | F | Me |
| C-244 | 1 | H | Et | Cl | Me |
| C-245 | 1 | H | Et | CF₃ | F |
| C-246 | 1 | H | Et | CF₃ | Cl |
| C-247 | 1 | H | Et | CF₃ | Me |
| C-248 | 1 | H | Et | CN | F |
| C-249 | 1 | H | Et | CN | Cl |
| C-250 | 1 | H | Et | ethynyl | F |
| C-251 | 1 | H | Et | ethynyl | Cl |
| C-252 | 1 | H | Et | ethynyl | Me |
| C-253 | 1 | H | Et | ethynyl | CF₃ |
| C-254 | 1 | H | Et | OCF₃ | F |
| C-255 | 1 | H | Et | OCF₃ | Cl |
| C-256 | 1 | H | Et | OCF₃ | Me |
| C-257 | 1 | H | Et | OCF₃ | ethynyl |
| C-258 | 1 | H | CN | F | Cl |
| C-259 | 1 | H | CN | F | Me |
| C-260 | 1 | H | CN | Cl | Me |
| C-261 | 1 | H | CN | CF₃ | F |
| C-262 | 1 | H | CN | CF₃ | Cl |
| C-263 | 1 | H | CN | CF₃ | Me |
| C-264 | 1 | H | CN | CN | F |
| C-265 | 1 | H | CN | CN | Cl |
| C-266 | 1 | H | CN | ethynyl | F |
| C-267 | 1 | H | CN | ethynyl | Cl |
| C-268 | 1 | H | CN | ethynyl | Me |
| C-269 | 1 | H | CN | ethynyl | CF₃ |
| C-270 | 1 | H | CN | OCF₃ | F |
| C-271 | 1 | H | CN | OCF₃ | Cl |
| C-272 | 1 | H | CN | OCF₃ | Me |
| C-273 | 1 | H | CN | OCF₃ | ethynyl |
| C-274 | 1 | H | CF₃ | F | Cl |
| C-275 | 1 | H | CF₃ | F | Me |
| C-276 | 1 | H | CF₃ | Cl | Me |
| C-277 | 1 | H | CF₃ | CF₃ | F |
| C-278 | 1 | H | CF₃ | CF₃ | Cl |
| C-279 | 1 | H | CF₃ | CF₃ | Me |
| C-280 | 1 | H | CF₃ | CN | F |
| C-281 | 1 | H | CF₃ | CN | Cl |
| C-282 | 1 | H | CF₃ | ethynyl | F |
| C-283 | 1 | H | CF₃ | ethynyl | Cl |
| C-284 | 1 | H | CF₃ | ethynyl | Me |
| C-285 | 1 | H | CF₃ | ethynyl | CF₃ |
| C-286 | 1 | H | CF₃ | OCF₃ | F |
| C-287 | 1 | H | CF₃ | OCF₃ | Cl |
| C-288 | 1 | H | CF₃ | OCF₃ | Me |
| C-289 | 1 | H | CF₃ | OCF₃ | ethynyl |
| C-290 | 1 | H | CH₂CN | F | Cl |
| C-291 | 1 | H | CH₂CN | F | Me |
| C-292 | 1 | H | CH₂CN | Cl | Me |
| C-293 | 1 | H | CH₂CN | CF₃ | F |
| C-294 | 1 | H | CH₂CN | CF₃ | Cl |
| C-295 | 1 | H | CH₂CN | CF₃ | Me |
| C-296 | 1 | H | CH₂CN | CN | F |
| C-297 | 1 | H | CH₂CN | CN | Cl |
| C-298 | 1 | H | CH₂CN | ethynyl | F |
| C-299 | 1 | H | CH₂CN | ethynyl | Cl |
| C-300 | 1 | H | CH₂CN | ethynyl | Me |
| C-301 | 1 | H | CH₂CN | ethynyl | CF₃ |
| C-302 | 1 | H | CH₂CN | OCF₃ | F |
| C-303 | 1 | H | CH₂CN | OCF₃ | Cl |
| C-304 | 1 | H | CH₂CN | OCF₃ | Me |
| C-305 | 1 | H | CH₂CN | OCF₃ | ethynyl |
| C-306 | 1 | H | CH₂OMe | F | Cl |
| C-307 | 1 | H | CH₂OMe | F | Me |
| C-308 | 1 | H | CH₂OMe | Cl | Me |
| C-309 | 1 | H | CH₂OMe | CF₃ | F |
| C-310 | 1 | H | CH₂OMe | CF₃ | Cl |
| C-311 | 1 | H | CH₂OMe | CF₃ | Me |
| C-312 | 1 | H | CH₂OMe | CN | F |
| C-313 | 1 | H | CH₂OMe | CN | Cl |
| C-314 | 1 | H | CH₂OMe | ethynyl | F |
| C-315 | 1 | H | CH₂OMe | ethynyl | Cl |
| C-316 | 1 | H | CH₂OMe | ethynyl | Me |
| C-317 | 1 | H | CH₂OMe | ethynyl | CF₃ |
| C-318 | 1 | H | CH₂OMe | OCF₃ | F |
| C-319 | 1 | H | CH₂OMe | OCF₃ | Cl |
| C-320 | 1 | H | CH₂OMe | OCF₃ | Me |
| C-321 | 1 | H | CH₂OMe | OCF₃ | ethynyl |

Further preferred meanings of Q are given in Table D.

TABLE D

| No. | Q |
|---|---|
| D-001 | 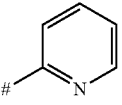 |
| D-002 | 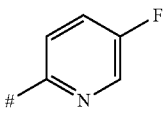 |
| D-003 | 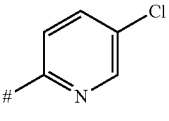 |
| D-004 | 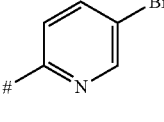 |
| D-005 | 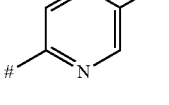 |
| D-006 | 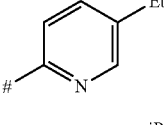 |
| D-007 | 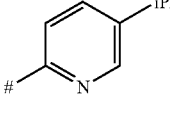 |
| D-008 | 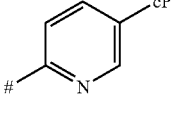 |
| D-009 | 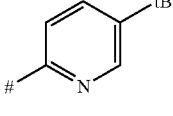 |

TABLE D-continued

| No. | Q |
|---|---|
| D-010 | 5-OMe-pyridin-2-yl (#) |
| D-011 | 5-OEt-pyridin-2-yl (#) |
| D-012 | 5-OiPr-pyridin-2-yl (#) |
| D-013 | 5-vinyl-pyridin-2-yl (#) |
| D-014 | 5-ethynyl-pyridin-2-yl (#) |
| D-015 | 5-CN-pyridin-2-yl (#) |
| D-016 | 5-CF$_3$-pyridin-2-yl (#) |
| D-017 | 5-OCF$_3$-pyridin-2-yl (#) |
| D-018 | 5-CHF$_2$-pyridin-2-yl (#) |
| D-019 | 5-CH$_2$F-pyridin-2-yl (#) |
| D-020 | 5-OCHF$_2$-pyridin-2-yl (#) |
| D-021 | 5-OCH$_2$F-pyridin-2-yl (#) |
| D-022 | pyridin-3-yl (#) |
| D-023 | 2-F-pyridin-5-yl (#) |
| D-024 | 2-Cl-pyridin-5-yl (#) |
| D-025 | 2-Br-pyridin-5-yl (#) |
| D-026 | 2-Me-pyridin-5-yl (#) |
| D-027 | 2-Et-pyridin-5-yl (#) |
| D-028 | 2-iPr-pyridin-5-yl (#) |
| D-029 | 2-cPr-pyridin-5-yl (#) |
| D-030 | 2-tBu-pyridin-5-yl (#) |
| D-031 | 2-OMe-pyridin-5-yl (#) |
| D-032 | 2-OEt-pyridin-5-yl (#) |
| D-033 | 2-OiPr-pyridin-5-yl (#) |
| D-034 | 2-vinyl-pyridin-5-yl (#) |

TABLE D-continued
| No. | Q |
|---|---|
| D-035 | 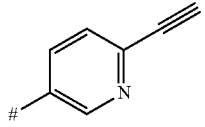 |
| D-036 | 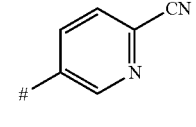 |
| D-037 | 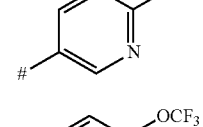 |
| D-038 | 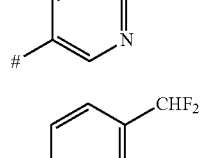 |
| D-039 | 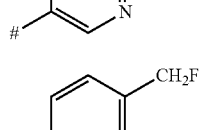 |
| D-040 | 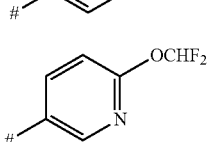 |
| D-041 | 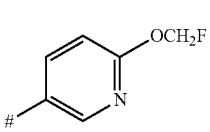 |
| D-042 | 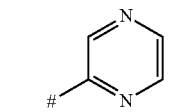 |
| D-043 | 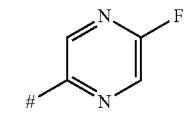 |
| D-044 | 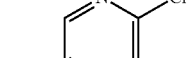 |
| D-045 | 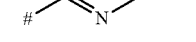 |
| D-046 | 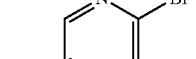 |
| D-047 | 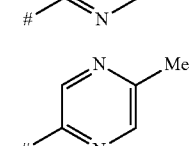 |
TABLE D-continued
| No. | Q |
|---|---|
| D-048 | 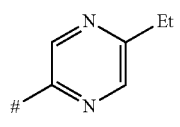 |
| D-049 | 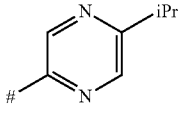 |
| D-050 | 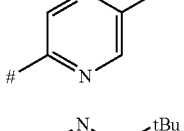 |
| D-051 | 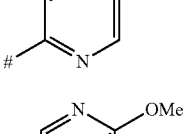 |
| D-052 | 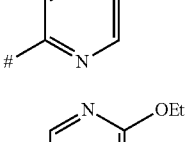 |
| D-053 | 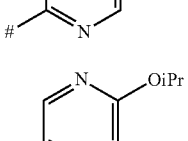 |
| D-054 | 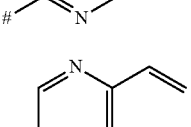 |
| D-055 | 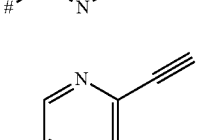 |
| D-056 | 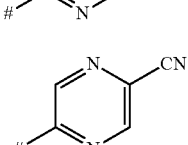 |
| D-057 | 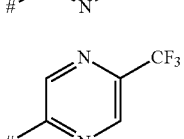 |
| D-058 | 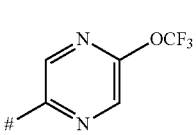 |
| D-059 |  |

TABLE D-continued
| No. | Q |
|---|---|
| D-060 | 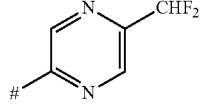 |
| D-061 | 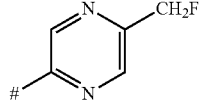 |
| D-062 | 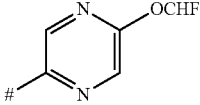 |
| D-063 | 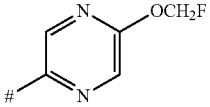 |
| D-064 | 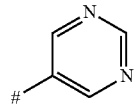 |
| D-065 | 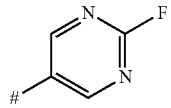 |
| D-066 | 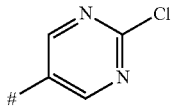 |
| D-067 | 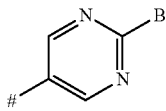 |
| D-068 | 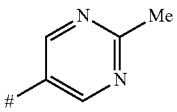 |
| D-069 | 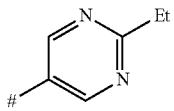 |
| D-070 | 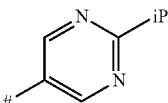 |
| D-071 | 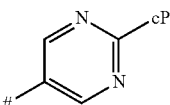 |
| D-072 | 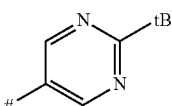 |
| D-073 | 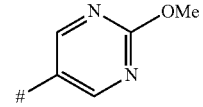 |
| D-074 | 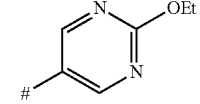 |
| D-075 | 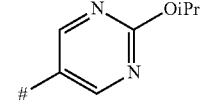 |
| D-076 | 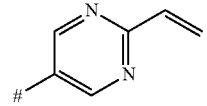 |
| D-077 | 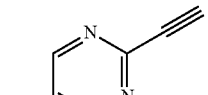 |
| D-078 | 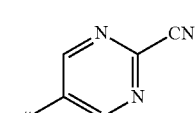 |
| D-079 | 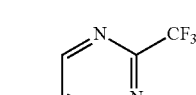 |
| D-080 | 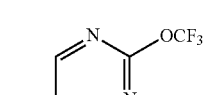 |
| D-081 | 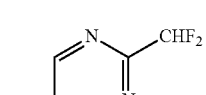 |
| D-082 | 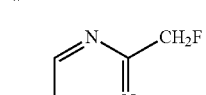 |
| D-083 | 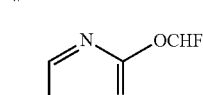 |
| D-084 | 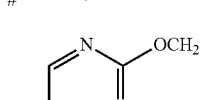 |
| D-085 | 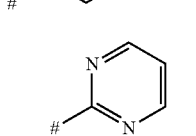 |

TABLE D-continued

| No. | Q |
|---|---|
| D-086 | 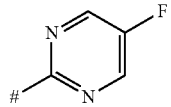 5-F pyrimidin-2-yl |
| D-087 | 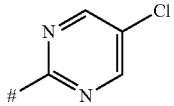 5-Cl pyrimidin-2-yl |
| D-088 | 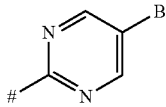 5-Br pyrimidin-2-yl |
| D-089 | 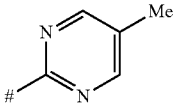 5-Me pyrimidin-2-yl |
| D-090 | 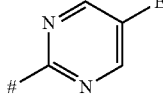 5-Et pyrimidin-2-yl |
| D-091 | 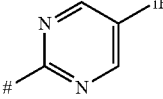 5-iPr pyrimidin-2-yl |
| D-092 | 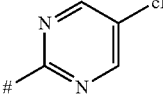 5-cPr pyrimidin-2-yl |
| D-093 | 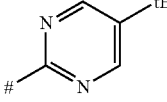 5-tBu pyrimidin-2-yl |
| D-094 | 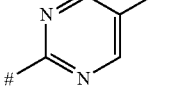 5-OMe pyrimidin-2-yl |
| D-095 | 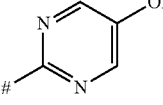 5-OEt pyrimidin-2-yl |
| D-096 | 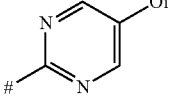 5-OiPr pyrimidin-2-yl |
| D-097 | 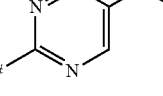 5-vinyl pyrimidin-2-yl |

TABLE D-continued

| No. | Q |
|---|---|
| D-098 | 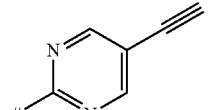 5-ethynyl pyrimidin-2-yl |
| D-099 | 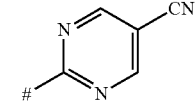 5-CN pyrimidin-2-yl |
| D-100 | 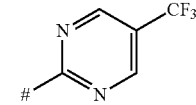 5-CF$_3$ pyrimidin-2-yl |
| D-101 | 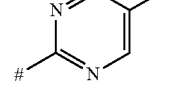 5-OCF$_3$ pyrimidin-2-yl |
| D-102 | 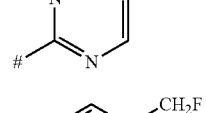 5-CHF$_2$ pyrimidin-2-yl |
| D-103 | 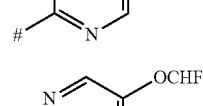 5-CH$_2$F pyrimidin-2-yl |
| D-104 | 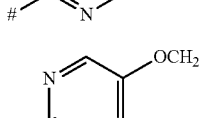 5-OCHF$_2$ pyrimidin-2-yl |
| D-105 | 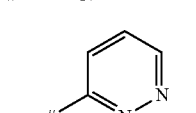 5-OCH$_2$F pyrimidin-2-yl |
| D-106 | 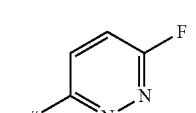 pyridazin-3-yl |
| D-107 | 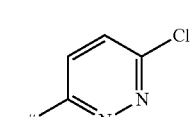 6-F pyridazin-3-yl |
| D-108 | 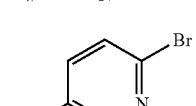 6-Cl pyridazin-3-yl |
| D-109 | 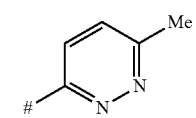 6-Br pyridazin-3-yl |
| D-110 |  6-Me pyridazin-3-yl |

TABLE D-continued

| No. | Q |
|---|---|
| D-111 | 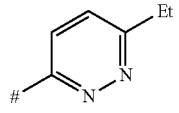 Et |
| D-112 | 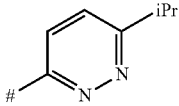 iPr |
| D-113 | 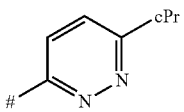 cPr |
| D-114 | 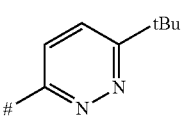 tBu |
| D-115 | 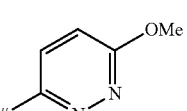 OMe |
| D-116 | 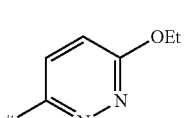 OEt |
| D-117 | 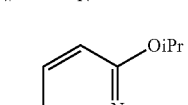 OiPr |
| D-118 | 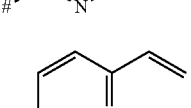 |
| D-119 | 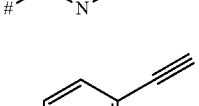 |
| D-120 | 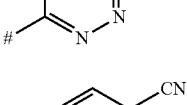 CN |
| D-121 | 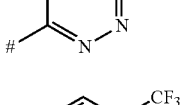 CF$_3$ |
| D-122 | 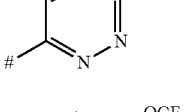 OCF$_3$ |
| D-123 | 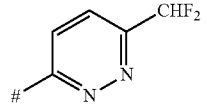 CHF$_2$ |
| D-124 | 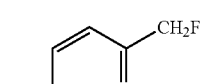 CH$_2$F |
| D-125 | 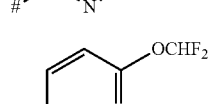 OCHF$_2$ |
| D-126 | 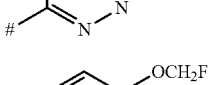 OCH$_2$F |

Table 1d: Compounds of formulae (Ia-1), (Ia-2) and (Ia-3), wherein Q is as defined in entry D-001 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-001 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-001 of table D and p, $R^1$, $R^3$, $R^{5a}$ and $R^{5b}$ correspond in each case to a row of table C.

Table 2d: Compounds of formulae (Ia-1), (Ia-2) and (Ia-3), wherein Q is as defined in entry D-002 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-002 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-002 of table D and p, $R^1$, $R^3$, $R^{5a}$ and $R^{5b}$ correspond in each case to a row of table C.

Table 3d: Compounds of formulae (Ia-1), (Ia-2) and (Ia-3), wherein Q is as defined in entry D-003 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-003 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-003 of table D and p, $R^1$, $R^3$, $R^{5a}$ and $R^{5b}$ correspond in each case to a row of table C.

Table 4d: Compounds of formulae (Ia-1), (Ia-2) and (Ia-3), wherein Q is as defined in entry D-004 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-004 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-004 of table D and p, $R^1$, $R^3$, $R^{5a}$ and $R^{5b}$ correspond in each case to a row of table C.

Table 5d: Compounds of formulae (Ia-1), (Ia-2) and (Ia-3), wherein Q is as defined in entry D-005 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-005 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-005 of table D and p, $R^1$, $R^3$, $R^{5a}$ and $R^{5b}$ correspond in each case to a row of table C.

Table 6d: Compounds of formulae (Ia-1), (Ia-2) and (Ia-3), wherein Q is as defined in entry D-6 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-6 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-6 of table D and p, $R^1$, $R^3$, $R^{5a}$ and $R^{5b}$ correspond in each case to a row of table C.

Table 7d: Compounds of formulae (Ia-1), (Ia-2) and (Ia-3), wherein Q is as defined in entry D-7 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-7 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-7 of table D and p, $R^1$, $R^3$, $R^{5a}$ and $R^{5b}$ correspond in each case to a row of table C.

Table 8d: Compounds of formulae (Ia-1), (Ia-2) and (Ia-3), wherein Q is as defined in entry D-8 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-8 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-8 of table D and p, R1, R3, R5a and R5b correspond in each case to a row of table C.

Table 9d: Compounds of formulae (Ia-1), (Ia-2) and (Ia-3), wherein Q is as defined in entry D-9 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-9 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-9 of table D and p, R1, R3, R5a and R5b correspond in each case to a row of table C.

Table 10d: Compounds of formulae (Ia-1), (Ia-2) and (Ia-3), wherein Q is as defined in entry D-10 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-10 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-10 of table D and p, R1, R3, R5a and R5b correspond in each case to a row of table C.

Table 11d: Compounds of formulae (Ia-1), (Ia-2) and (Ia-3), wherein Q is as defined in entry D-11 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-11 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-11 of table D and p, R1, R3, R5a and R5b correspond in each case to a row of table C.

Table 12d: Compounds of formulae (Ia-1), (Ia-2) and (Ia-3), wherein Q is as defined in entry D-12 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-12 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-12 of table D and p, R1, R3, R5a and R5b correspond in each case to a row of table C.

Table 13d: Compounds of formulae (Ia-1), (Ia-2) and (Ia-3), wherein Q is as defined in entry D-13 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-13 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-13 of table D and p, R1, R3, R5a and R5b correspond in each case to a row of table C.

Table 14d: Compounds of formulae (Ia-1), (Ia-2) and (Ia-3), wherein Q is as defined in entry D-14 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-14 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-14 of table D and p, R1, R3, R5a and R5b correspond in each case to a row of table C.

Table 15d: Compounds of formulae (Ia-1), (Ia-2) and (Ia-3), wherein Q is as defined in entry D-15 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-15 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-15 of table D and p, R1, R3, R5a and R5b correspond in each case to a row of table C.

Table 16d: Compounds of formulae (Ia-1), (Ia-2) and (Ia-3), wherein Q is as defined in entry D-16 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-16 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-16 of table D and p, R1, R3, R5a and R5b correspond in each case to a row of table C.

Table 17d: Compounds of formulae (Ia-1), (Ia-2) and (Ia-3), wherein Q is as defined in entry D-17 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-17 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-17 of table D and p, R1, R3, R5a and R5b correspond in each case to a row of table C.

Table 18d: Compounds of formulae (Ia-1), (Ia-2) and (Ia-3), wherein Q is as defined in entry D-18 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-18 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-18 of table D and p, R1, R3, R5a and R5b correspond in each case to a row of table C.

Table 19d: Compounds of formulae (Ia-1), (Ia-2) and (Ia-3), wherein Q is as defined in entry D-19 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-19 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-19 of table D and p, R1, R3, R5a and R5b correspond in each case to a row of table C.

Table 20d: Compounds of formulae (Ia-1), (Ia-2) and (Ia-3), wherein Q is as defined in entry D-20 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-20 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-20 of table D and p, R1, R3, R5a and R5b correspond in each case to a row of table C.

Table 21d: Compounds of formulae (Ia-1), (Ia-2) and (Ia-3), wherein Q is as defined in entry D-21 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-21 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-21 of table D and p, R1, R3, R5a and R5b correspond in each case to a row of table C.

Table 22d: Compounds of formulae (Ia-1), (Ia-2) and (Ia-3), wherein Q is as defined in entry D-22 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-22 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-22 of table D and p, R1, R3, R5a and R5b correspond in each case to a row of table C.

Table 23d: Compounds of formulae (Ia-1), (Ia-2) and (Ia-3), wherein Q is as defined in entry D-23 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-23 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-23 of table D and p, R1, R3, R5a and R5b correspond in each case to a row of table C.

Table 24d: Compounds of formulae (Ia-1), (Ia-2) and (Ia-3), wherein Q is as defined in entry D-24 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-24 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-24 of table D and p, R1, R3, R5a and R5b correspond in each case to a row of table C.

Table 25d: Compounds of formulae (Ia-1), (Ia-2) and (Ia-3), wherein Q is as defined in entry D-25 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-25 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-25 of table D and p, R1, R3, R5a and R5b correspond in each case to a row of table C.

Table 26d: Compounds of formulae (Ia-1), (Ia-2) and (Ia-3), wherein Q is as defined in entry D-26 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-26 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-26 of table D and p, R1, R3, R5a and R5b correspond in each case to a row of table C.

Table 27d: Compounds of formulae (Ia-1), (Ia-2) and (Ia-3), wherein Q is as defined in entry D-27 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-27 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-27 of table D and p, R1, R3, R5a and R5b correspond in each case to a row of table C.

Table 27d: Compounds of formulae (Ia-1), (Ia-2) and (Ia-3), wherein Q is as defined in entry D-27 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-27 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-27 of table D and p, R1, R3, R5a and R5b correspond in each case to a row of table C.

Table 28d: Compounds of formulae (Ia-1), (Ia-2) and (Ia-3), wherein Q is as defined in entry D-28 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-28 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-28 of table D and p, R1, R3, R5a and R5b correspond in each case to a row of table C.

Table 29d: Compounds of formulae (Ia-1), (Ia-2) and (Ia-3), wherein Q is as defined in entry D-29 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-29 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-29 of table D and p, R1, R3, R5a and R5b correspond in each case to a row of table C.

Table 30d: Compounds of formulae (Ia-1), (Ia-2) and (Ia-3), wherein Q is as defined in entry D-30 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-30 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-30 of table D and p, R1, R3, R5a and R5b correspond in each case to a row of table C.

Table 31d: Compounds of formulae (Ia-1), (Ia-2) and (Ia-3), wherein Q is as defined in entry D-31 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-31 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-31 of table D and p, R1, R3, R5a and R5b correspond in each case to a row of table C.

Table 32d: Compounds of formulae (Ia-1), (Ia-2) and (Ia-3), wherein Q is as defined in entry D-32 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-32 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-32 of table D and p, R1, R3, R5a and R5b correspond in each case to a row of table C.

Table 33d: Compounds of formulae (Ia-1), (Ia-2) and (Ia-3), wherein Q is as defined in entry D-33 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-33 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-33 of table D and p, R1, R3, R5a and R5b correspond in each case to a row of table C.

Table 34d: Compounds of formulae (Ia-1), (Ia-2) and (Ia-3), wherein Q is as defined in entry D-34 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-34 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-34 of table D and p, R1, R3, R5a and R5b correspond in each case to a row of table C.

Table 35d: Compounds of formulae (Ia-1), (Ia-2) and (Ia-3), wherein Q is as defined in entry D-35 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-35 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-35 of table D and p, R1, R3, R5a and R5b correspond in each case to a row of table C.

Table 36d: Compounds of formulae (Ia-1), (Ia-2) and (Ia-3), wherein Q is as defined in entry D-36 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-36 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-36 of table D and p, R1, R3, R5a and R5b correspond in each case to a row of table C.

Table 37d: Compounds of formulae (Ia-1), (Ia-2) and (Ia-3), wherein Q is as defined in entry D-37 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-37 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-37 of table D and p, R1, R3, R5a and R5b correspond in each case to a row of table C.

Table 38d: Compounds of formulae (Ia-1), (Ia-2) and (Ia-3), wherein Q is as defined in entry D-38 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-38 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-38 of table D and p, R1, R3, R5a and R5b correspond in each case to a row of table C.

Table 39d: Compounds of formulae (Ia-1), (Ia-2) and (Ia-3), wherein Q is as defined in entry D-39 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-39 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-39 of table D and p, R1, R3, R5a and R5b correspond in each case to a row of table C.

Table 40d: Compounds of formulae (Ia-1), (Ia-2) and (Ia-3), wherein Q is as defined in entry D-40 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-40 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-40 of table D and p, R1, R3, R5a and R5b correspond in each case to a row of table C.

Table 41d: Compounds of formulae (Ia-1), (Ia-2) and (Ia-3), wherein Q is as defined in entry D-41 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-41 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-41 of table D and p, R1, R3, R5a and R5b correspond in each case to a row of table C.

Table 42d: Compounds of formulae (Ia-1), (Ia-2) and (Ia-3), wherein Q is as defined in entry D-42 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-42 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-42 of table D and p, R1, R3, R5a and R5b correspond in each case to a row of table C.

Table 43d: Compounds of formulae (Ia-1), (Ia-2) and (Ia-3), wherein Q is as defined in entry D-43 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-43 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-43 of table D and p, R1, R3, R5a and R5b correspond in each case to a row of table C.

Table 44d: Compounds of formulae (Ia-1), (Ia-2) and (Ia-3), wherein Q is as defined in entry D-44 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-44 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-44 of table D and p, R1, R3, R5a and R5b correspond in each case to a row of table C.

Table 45d: Compounds of formulae (Ia-1), (Ia-2) and (Ia-3), wherein Q is as defined in entry D-45 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-45 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-45 of table D and p, R1, R3, R5a and R5b correspond in each case to a row of table C.

Table 46d: Compounds of formulae (Ia-1), (Ia-2) and (Ia-3), wherein Q is as defined in entry D-46 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-46 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-46 of table D and p, R1, R3, R5a and R5b correspond in each case to a row of table C.

Table 47d: Compounds of formulae (Ia-1), (Ia-2) and (Ia-3), wherein Q is as defined in entry D-47 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-47 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-47 of table D and p, R1, R3, R5a and R5b correspond in each case to a row of table C.

Table 48d: Compounds of formulae (Ia-1), (Ia-2) and (Ia-3), wherein Q is as defined in entry D-48 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-48 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-48 of table D and p, R1, R3, R5a and R5b correspond in each case to a row of table C.

Table 49d: Compounds of formulae (Ia-1), (Ia-2) and (Ia-3), wherein Q is as defined in entry D-49 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-49 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-49 of table D and p, R1, R3, R5a and R5b correspond in each case to a row of table C.

Table 50d: Compounds of formulae (Ia-1), (Ia-2) and (Ia-3), wherein Q is as defined in entry D-50 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-50 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-50 of table D and p, R1, R3, R5a and R5b correspond in each case to a row of table C.

Table 51d: Compounds of formulae (Ia-1), (Ia-2) and (Ia-3), wherein Q is as defined in entry D-51 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-51 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-51 of table D and p, R1, R3, R5a and R5b correspond in each case to a row of table C.

Table 52d: Compounds of formulae (Ia-1), (Ia-2) and (Ia-3), wherein Q is as defined in entry D-52 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-52 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-52 of table D and p, R1, R3, R5a and R5b correspond in each case to a row of table C.

Table 53d: Compounds of formulae (Ia-1), (Ia-2) and (Ia-3), wherein Q is as defined in entry D-53 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-53 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-53 of table D and p, R1, R3, R5a and R5b correspond in each case to a row of table C.

Table 54d: Compounds of formulae (Ia-1), (Ia-2) and (Ia-3), wherein Q is as defined in entry D-54 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-54 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-54 of table D and p, R1, R3, R5a and R5b correspond in each case to a row of table C.

Table 55d: Compounds of formulae (Ia-1), (Ia-2) and (Ia-3), wherein Q is as defined in entry D-55 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-55 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-55 of table D and p, R1, R3, R5a and R5b correspond in each case to a row of table C.

Table 56d: Compounds of formulae (Ia-1), (Ia-2) and (Ia-3), wherein Q is as defined in entry D-56 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-56 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-56 of table D and p, R1, R3, R5a and R5b correspond in each case to a row of table C.

Table 57d: Compounds of formulae (Ia-1), (Ia-2) and (Ia-3), wherein Q is as defined in entry D-57 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-57 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-57 of table D and p, R1, R3, R5a and R5b correspond in each case to a row of table C.

Table 58d: Compounds of formulae (Ia-1), (Ia-2) and (Ia-3), wherein Q is as defined in entry D-58 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-58 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-58 of table D and p, R1, R3, R5a and R5b correspond in each case to a row of table C.

Table 59d: Compounds of formulae (Ia-1), (Ia-2) and (Ia-3), wherein Q is as defined in entry D-59 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-59 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-59 of table D and p, R1, R3, R5a and R5b correspond in each case to a row of table C.

Table 60d: Compounds of formulae (Ia-1), (Ia-2) and (Ia-3), wherein Q is as defined in entry D-60 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-60 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-60 of table D and p, R1, R3, R5a and R5b correspond in each case to a row of table C.

Table 61d: Compounds of formulae (Ia-1), (Ia-2) and (Ia-3), wherein Q is as defined in entry D-61 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-61 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-61 of table D and p, R1, R3, R5a and R5b correspond in each case to a row of table C.

Table 62d: Compounds of formulae (Ia-1), (Ia-2) and (Ia-3), wherein Q is as defined in entry D-62 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-62 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-62 of table D and p, R1, R3, R5a and R5b correspond in each case to a row of table C.

Table 63d: Compounds of formulae (Ia-1), (Ia-2) and (Ia-3), wherein Q is as defined in entry D-63 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-63 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as Table 64d: Compounds of formulae (Ia-1), (Ia-2) and (Ia-3), wherein Q is as defined in entry D-64 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-64 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-64 of table D and p, R1, R3, R5a and R5b correspond in each case to a row of table C.

Table 65d: Compounds of formulae (Ia-1), (Ia-2) and (Ia-3), wherein Q is as defined in entry D-65 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-65 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-65 of table D and p, R1, R3, R5a and R5b correspond in each case to a row of table C.

Table 66d: Compounds of formulae (Ia-1), (Ia-2) and (Ia-3), wherein Q is as defined in entry D-66 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-66 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-66 of table D and p, R1, R3, R5a and R5b correspond in each case to a row of table C.

Table 67d: Compounds of formulae (Ia-1), (Ia-2) and (Ia-3), wherein Q is as defined in entry D-67 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-67 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-67 of table D and p, R1, R3, R5a and R5b correspond in each case to a row of table C.

Table 68d: Compounds of formulae (Ia-1), (Ia-2) and (Ia-3), wherein Q is as defined in entry D-68 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-68 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-68 of table D and p, R1, R3, R5a and R5b correspond in each case to a row of table C.

Table 69d: Compounds of formulae (Ia-1), (Ia-2) and (Ia-3), wherein Q is as defined in entry D-69 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-69 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-69 of table D and p, R1, R3, R5a and R5b correspond in each case to a row of table C.

Table 70d: Compounds of formulae (Ia-1), (Ia-2) and (Ia-3), wherein Q is as defined in entry D-70 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-70 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-70 of table D and p, R1, R3, R5a and R5b correspond in each case to a row of table C.

Table 71d: Compounds of formulae (Ia-1), (Ia-2) and (Ia-3), wherein Q is as defined in entry D-71 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-71 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-71 of table D and p, R1, R3, R5a and R5b correspond in each case to a row of table C.

Table 72d: Compounds of formulae (Ia-1), (Ia-2) and (Ia-3), wherein Q is as defined in entry D-72 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-72 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-72 of table D and p, R1, R3, R5a and R5b correspond in each case to a row of table C.

Table 73d: Compounds of formulae (Ia-1), (Ia-2) and (Ia-3), wherein Q is as defined in entry D-73 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-73 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-73 of table D and p, R1, R3, R5a and R5b correspond in each case to a row of table C.

Table 74d: Compounds of formulae (Ia-1), (Ia-2) and (Ia-3), wherein Q is as defined in entry D-74 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-74 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-74 of table D and p, R1, R3, R5a and R5b correspond in each case to a row of table C.

Table 75d: Compounds of formulae (Ia-1), (Ia-2) and (Ia-3), wherein Q is as defined in entry D-75 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-75 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-75 of table D and p, R1, R3, R5a and R5b correspond in each case to a row of table C.

Table 76d: Compounds of formulae (Ia-1), (Ia-2) and (Ia-3), wherein Q is as defined in entry D-76 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-76 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-76 of table D and p, R1, R3, R5a and R5b correspond in each case to a row of table C.

Table 77d: Compounds of formulae (Ia-1), (Ia-2) and (Ia-3), wherein Q is as defined in entry D-77 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-77 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-77 of table D and p, R1, R3, R5a and R5b correspond in each case to a row of table C.

Table 78d: Compounds of formulae (Ia-1), (Ia-2) and (Ia-3), wherein Q is as defined in entry D-78 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-78 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-78 of table D and p, R1, R3, R5a and R5b correspond in each case to a row of table C.

Table 79d: Compounds of formulae (Ia-1), (Ia-2) and (Ia-3), wherein Q is as defined in entry D-79 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-79 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-79 of table D and p, R1, R3, R5a and R5b correspond in each case to a row of table C.

Table 80d: Compounds of formulae (Ia-1), (Ia-2) and (Ia-3), wherein Q is as defined in entry D-80 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-80 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-80 of table D and p, R1, R3, R5a and R5b correspond in each case to a row of table C.

Table 81d: Compounds of formulae (Ia-1), (Ia-2) and (Ia-3), wherein Q is as defined in entry D-81 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-81 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-81 of table D and p, R1, R3, R5a and R5b correspond in each case to a row of table C.

Table 82d: Compounds of formulae (Ia-1), (Ia-2) and (Ia-3), wherein Q is as defined in entry D-82 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-82 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-82 of table D and p, R1, R3, R5a and R5b correspond in each case to a row of table C.

Table 83d: Compounds of formulae (Ia-1), (Ia-2) and (Ia-3), wherein Q is as defined in entry D-83 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-83 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-83 of table D and p, R1, R3, R5a and R5b correspond in each case to a row of table C.

Table 84d: Compounds of formulae (Ia-1), (Ia-2) and (Ia-3), wherein Q is as defined in entry D-84 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-84 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-84 of table D and p, R1, R3, R5a and R5b correspond in each case to a row of table C.

Table 85d: Compounds of formulae (Ia-1), (Ia-2) and (Ia-3), wherein Q is as defined in entry D-85 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-85 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-85 of table D and p, R1, R3, R5a and R5b correspond in each case to a row of table C.

Table 86d: Compounds of formulae (Ia-1), (Ia-2) and (Ia-3), wherein Q is as defined in entry D-86 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-86 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-86 of table D and p, R1, R3, R5a and R5b correspond in each case to a row of table C.

Table 87d: Compounds of formulae (Ia-1), (Ia-2) and (Ia-3), wherein Q is as defined in entry D-87 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-87 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-87 of table D and p, R1, R3, R5a and R5b correspond in each case to a row of table C.

Table 88d: Compounds of formulae (Ia-1), (Ia-2) and (Ia-3), wherein Q is as defined in entry D-88 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-88 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-88 of table D and p, R1, R3, R5a and R5b correspond in each case to a row of table C.

Table 89d: Compounds of formulae (Ia-1), (Ia-2) and (Ia-3), wherein Q is as defined in entry D-89 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-89 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-89 of table D and p, R1, R3, R5a and R5b correspond in each case to a row of table C.

Table 90d: Compounds of formulae (Ia-1), (Ia-2) and (Ia-3), wherein Q is as defined in entry D-90 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-90 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-90 of table D and p, R1, R3, R5a and R5b correspond in each case to a row of table C.

Table 91d: Compounds of formulae (Ia-1), (Ia-2) and (Ia-3), wherein Q is as defined in entry D-91 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-91 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-91 of table D and p, R1, R3, R5a and R5b correspond in each case to a row of table C.

Table 92d: Compounds of formulae (Ia-1), (Ia-2) and (Ia-3), wherein Q is as defined in entry D-92 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-92 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-92 of table D and p, R1, R3, R5a and R5b correspond in each case to a row of table C.

Table 93: Compounds of formulae (Ia-1), (Ia-2) and (Ia-3), wherein Q is as defined in entry D-93 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-93 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-93 of table D and p, R1, R3, R5a and R5b correspond in each case to a row of table C.

Table 94d: Compounds of formulae (Ia-1), (Ia-2) and (Ia-3), wherein Q is as defined in entry D-94 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-94 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-94 of table D and p, R1, R3, R5a and R5b correspond in each case to a row of table C.

Table 95d: Compounds of formulae (Ia-1), (Ia-2) and (Ia-3), wherein Q is as defined in entry D-95 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-95 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-95 of table D and p, R1, R3, R5a and R5b correspond in each case to a row of table C.

Table 96d: Compounds of formulae (Ia-1), (Ia-2) and (Ia-3), wherein Q is as defined in entry D-96 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-96 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-96 of table D and p, R1, R3, R5a and R5b correspond in each case to a row of table C.

Table 97d: Compounds of formulae (Ia-1), (Ia-2) and (Ia-3), wherein Q is as defined in entry D-97 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-97 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-97 of table D and p, R1, R3, R5a and R5b correspond in each case to a row of table C.

Table 98d: Compounds of formulae (Ia-1), (Ia-2) and (Ia-3), wherein Q is as defined in entry D-98 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-98 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-98 of table D and p, R1, R3, R5a and R5b correspond in each case to a row of table C.

Table 99d: Compounds of formulae (Ia-1), (Ia-2) and (Ia-3), wherein Q is as defined in entry D-99 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-99 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-99 of table D and p, R1, R3, R5a and R5b correspond in each case to a row of table C.

Table 100d: Compounds of formulae (Ia-1), (Ia-2) and (Ia-3), wherein 0 is as defined in entry D-100 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-100 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-100 of table D and p, R1, R3, R5a and R5b correspond in each case to a row of table C.

Table 101d: Compounds of formulae (Ia-1), (Ia-2) and (Ia-3), wherein Q is as defined in entry D-101 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-101 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-101 of table D and p, R1, R3, R5a and R5b correspond in each case to a row of table C.

Table 102d: Compounds of formulae (Ia-1), (Ia-2) and (Ia-3), wherein Q is as defined in entry D-102 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-102 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-102 of table D and p, R1, R3, R5a and R5b correspond in each case to a row of table C.

Table 103d: Compounds of formulae (Ia-1), (Ia-2) and (Ia-3), wherein Q is as defined in entry D-103 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-103 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-103 of table D and p, R1, R3, R5a and R5b correspond in each case to a row of table C.

Table 104d: Compounds of formulae (Ia-1), (Ia-2) and (Ia-3), wherein Q is as defined in entry D-104 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-104 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-104 of table D and p, R1, R3, R5a and R5b correspond in each case to a row of table C.

Table 105d: Compounds of formulae (Ia-1), (Ia-2) and (Ia-3), wherein Q is as defined in entry D-105 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-105 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-105 of table D and p, R1, R3, R5a and R5b correspond in each case to a row of table C.

Table 106d: Compounds of formulae (Ia-1), (Ia-2) and (Ia-3), wherein Q is as defined in entry D-106 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-106 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-106 of table D and p, R1, R3, R5a and R5b correspond in each case to a row of table C.

Table 107d: Compounds of formulae (Ia-1), (Ia-2) and (Ia-3), wherein Q is as defined in entry D-107 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-107 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-107 of table D and p, R1, R3, R5a and R5b correspond in each case to a row of table C.

Table 108d: Compounds of formulae (Ia-1), (Ia-2) and (Ia-3), wherein Q is as defined in entry D-108 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-108 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-108 of table D and p, R1, R3, R5a and R5b correspond in each case to a row of table C.

Table 109d: Compounds of formulae (Ia-1), (Ia-2) and (Ia-3), wherein Q is as defined in entry D-109 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-109 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-109 of table D and p, R1, R3, R5a and R5b correspond in each case to a row of table C.

Table 110d: Compounds of formulae (Ia-1), (Ia-2) and (Ia-3), wherein Q is as defined in entry D-110 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-110 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-110 of table D and p, R1, R3, R5a and R5b correspond in each case to a row of table C.

Table 111d: Compounds of formulae (Ia-1), (Ia-2) and (Ia-3), wherein Q is as defined in entry D-111 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-111 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-111 of table D and p, R1, R3, R5a and R5b correspond in each case to a row of table C.

Table 112d: Compounds of formulae (Ia-1), (Ia-2) and (Ia-3), wherein Q is as defined in entry D-112 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-112 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-112 of table D and p, R1, R3, R5a and R5b correspond in each case to a row of table C.

Table 113d: Compounds of formulae (Ia-1), (Ia-2) and (Ia-3), wherein Q is as defined in entry D-113 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-113 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-113 of table D and p, R1, R3, R5a and R5b correspond in each case to a row of table C.

Table 114d: Compounds of formulae (Ia-1), (Ia-2) and (Ia-3), wherein Q is as defined in entry D-114 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-114 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-114 of table D and p, R1, R3, R5a and R5b correspond in each case to a row of table C.

Table 115d: Compounds of formulae (Ia-1), (Ia-2) and (Ia-3), wherein Q is as defined in entry D-115 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-115 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-115 of table D and p, R1, R3, R5a and R5b correspond in each case to a row of table C.

Table 116d: Compounds of formulae (Ia-1), (Ia-2) and (Ia-3), wherein Q is as defined in entry D-116 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-116 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-116 of table D and p, R1, R3, R5a and R5b correspond in each case to a row of table C.

Table 117d: Compounds of formulae (Ia-1), (Ia-2) and (Ia-3), wherein Q is as defined in entry D-117 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-117 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-117 of table D and p, R1, R3, R5a and R5b correspond in each case to a row of table C.

Table 118d: Compounds of formulae (Ia-1), (Ia-2) and (Ia-3), wherein Q is as defined in entry D-118 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-118 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-118 of table D and p, R1, R3, R5a and R5b correspond in each case to a row of table C.

Table 119d: Compounds of formulae (Ia-1), (Ia-2) and (Ia-3), wherein Q is as defined in entry 0-119 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-119 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-119 of table D and p, R1, R3, R5a and R5b correspond in each case to a row of table C.

Table 120d: Compounds of formulae (Ia-1), (Ia-2) and (Ia-3), wherein Q is as defined in entry D-120 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-120 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-120 of table D and p, R1, R3, R5a and R5b correspond in each case to a row of table C.

Table 121d: Compounds of formulae (Ia-1), (Ia-2) and (Ia-3), wherein Q is as defined in entry D-121 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-121 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-121 of table D and p, R1, R3, R5a and R5b correspond in each case to a row of table C.

Table 122d: Compounds of formulae (Ia-1), (Ia-2) and (Ia-3), wherein Q is as defined in entry D-122 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-122 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-122 of table D and p, R1, R3, R5a and R5b correspond in each case to a row of table C.

Table 123d: Compounds of formulae (Ia-1), (Ia-2) and (Ia-3), wherein Q is as defined in entry D-123 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-123 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-123 of table D and p, R1, R3, R5a and R5b correspond in each case to a row of table C.

Table 124d: Compounds of formulae (Ia-1), (Ia-2) and (Ia-3), wherein Q is as defined in entry D-124 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-124 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry 0-124 of table D and p, R1, R3, R5a and R5b correspond in each case to a row of table C.

Table 125d: Compounds of formulae (Ia-1), (Ia-2) and (Ia-3), wherein Q is as defined in entry D-125 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-125 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-125 of table D and p, R1, R3, R5a and R5b correspond in each case to a row of table C.

Table 126d: Compounds of formulae (Ia-1), (Ia-2) and (Ia-3), wherein Q is as defined in entry D-126 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-126 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-126 of table D and p, R1, R3, R5a and R5b correspond in each case to a row of table C.

Preparation Methods

The compounds of formula (I) according to the present invention can be prepared e.g. according to preparation methods and preparation schemes described below.

In the following schemes and methods, if not otherwise specified, the definition of the substituents, variables and indices in the formulae used correspond to the definitions given for formula (I) above.

Compounds of formula (I) can be prepared as shown in Scheme A below.

Scheme A

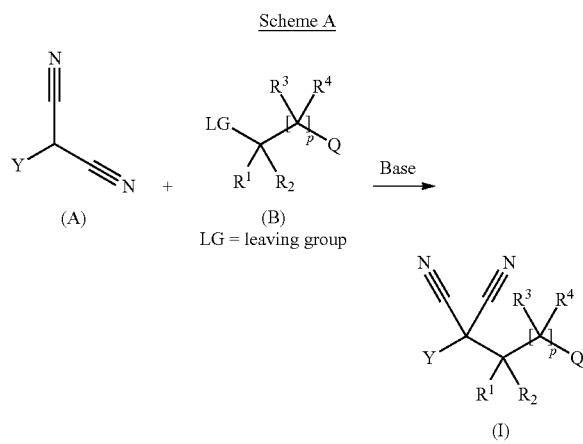

Compounds of formula (A) are reacted with compounds of formula (B) in the presence of a suitable base to give compounds of formula (I). A representative procedure has been described in e.g. M. M. Meyers, J. Sun, K. E. Carlson, G. A. Marriner, B. S. Katzenellenbogen, J. A. Katzenellenbogen, J. Med. Chem. 2001, 44, 4230-4251.

Compounds of formula (A) can be prepared by treatment of the corresponding iodine compound (A-1) with malonodinitrile (Scheme B) as described in various publications. For example, this can be achieved in the presence of a base and a suitable catalyst system as described in e.g. J. M. Atkins, S. A. Moteki, S. G. DiMagno, J. M. Takacs, Org. Lett. 2006, 13, 2759-2762. Alternatively, the reaction can also be carried out via copper catalysis in the presence of a base as described e.g. in M. Makosza, A. Chesnokov, Tetrahedron 2008, 64, 5925-5932.

Scheme B

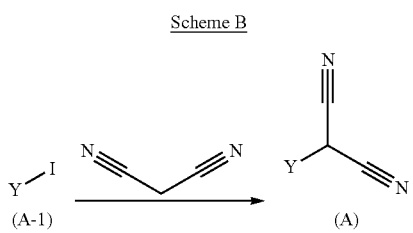

Compounds of formula (B) with p=0 like e.g. (B-5) in Scheme C that require a leaving group "LG" e.g. halogens or mesylates can be obtained starting from the respective halogenated compounds (B-1) as depicted below.

Scheme C

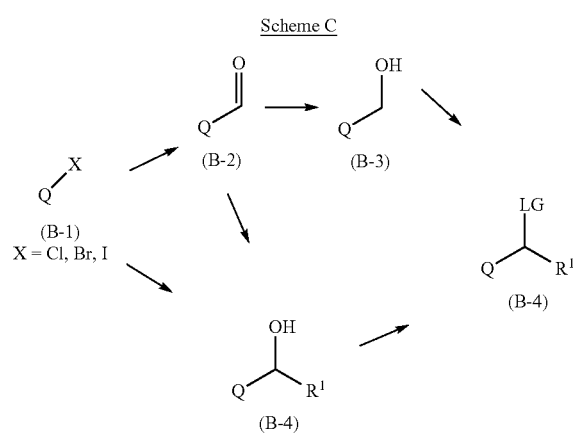

Reacting compounds of formula (B-1) with a lithium base followed by subsequent addition of DMF as described in e.g. WO 2012/058116 thus yields compounds of formula (B-2) which after reduction with e.g. a hydride reagent such as sodium borohydride yield (B-3) as described e.g. in WO 2012/022681.

Alternatively, compounds of formula (B-1) can also be treated with aldehydes e.g. acetaldehyde after reaction with a lithium base to directly yield compounds of formula (B-4) as described in e.g. Y. Zhang, J. P. Burgess, M. Brackeen, A. Gilliam, S. W. Mascarella, K. Page, H. H. Seltzman, B. F. Thomas, J. Med. Chem. 2008, 51, 3526-3539. Furthermore, various nucleophiles can be reacted with intermediates of formula (B-2) to yield mono- or disubstituted alcohols of formula (B-4) as described in e.g. J. A. Malona, K. Cariou, W. T. Spencer III, A. J. Frontier, J. Org. Chem. 2012, 77, 1891-1908.

Compounds of formula (B-3) or (B-4) can be converted into compounds of formula (B-5) by means of activating the hydroxyl group e.g. via mesylation or tosylation as described in WO 2012/085645. Alternatively, they can be treated with phosphortribromide to convert the hydroxyl group into the respective bromide as described in WO 2012/022487.

Compounds of formula (B) with p=1 like e.g. (B-6), (B-11), (B-12) or (B15) can be obtained starting from the respective carboxylic acid derivatives of formula (B-7), (B-9) or (B-13) as depicted in Schemes D to F.

α-Alkylation can be employed to introduce $R^3$ and $R^4$ substituents as described in e.g. WO 2012/058134. Substituents $R^1$ and $R^2$ can be introduced, for example, by treatment of compounds of formula (B-8), (B-9), (B-10) or (B-14) with e.g. hydride reagents or Grignard reagents as described in e.g. A. K. Ghosh, C. D. Martyr, C.-X. Xu, Org. Lett. 2012, 14, 2002-2005.

Scheme D

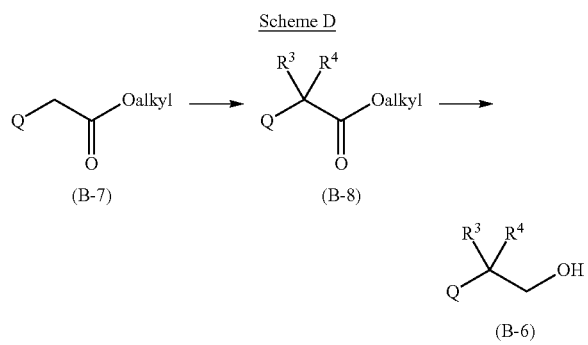

Scheme E

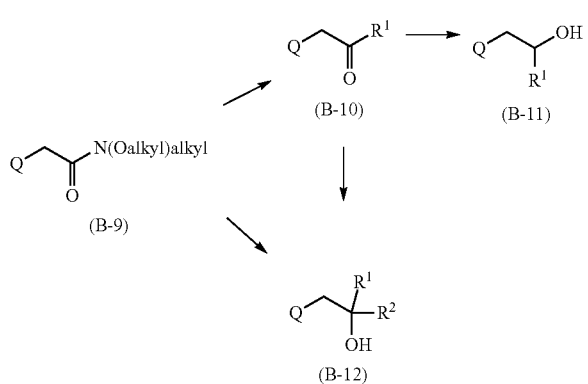

Scheme F

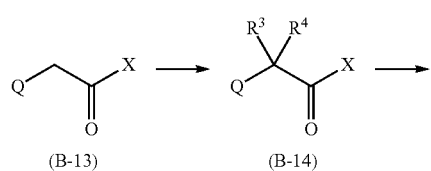

-continued

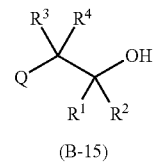

(B-15)

X = Oalkyl, N(Oalkyl)alkyl

The alcohols of formula (B-6), (B-11), (B-12) or (B15) can be further activated by similar methods as described above.

Iodo compounds of formula (A-1), chloro, bromo or iodo compounds of formula (B-1) as well as carboxylic acid derivatives needed for compounds of formula (B-7), (B-9) or (B-13) can be purchased or synthesized according to known literature methods.

As a rule, the compounds of formula (I) can be prepared by the methods described above. If individual compounds cannot be prepared via the above-described routes, they can be prepared by derivatization of other compounds (I) or by customary modifications of the synthesis routes described. For example, in individual cases, certain compounds (I) can advantageously be prepared from other compounds (I) by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or trituration with an appropriate solvent.

In one aspect of the invention there is provided a method for preparing a compound of formula (I) according to the invention or a salt or N-oxide thereof, comprising the step of reacting a compound of formula (XI) with a compound of formula (XII) optionally in the presence of a base.

In one embodiment the reaction of the compound of formula (XI) with the compound of formula (XII) is carried out in the absence of a base.

In a preferred embodiment the reaction of the compound of formula (XI) with the compound of formula (XII) is carried out in the presence of a base.

Preferred, more preferred, even more preferred and particularly preferred compounds of formula (XI) are the ones leading to the respective preferred, more preferred, even more preferred and particularly preferred compounds of formula (I).

Preferred, more preferred, even more preferred and particularly preferred compounds of formula (XII) are the ones leading to the respective preferred, more preferred, even more preferred and particularly preferred compounds of formula (I).

Preference is given to compounds of formula (XII) wherein

L is halogen or $OS(O)_2R^*$; and $R^*$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl is independently unsubstituted or substituted with up to 5 substituents selected from halogen, CN, $NO_2$, $C_1$-$C_6$-alkyl, $C_1$-$C_6$-haloalkyl or $C_1$-$C_6$-alkoxy.

Particular preference is given to compounds of formula (XII) wherein
L is Cl, Br, I or $OS(O)_2R^*$; and
$R^*$ is $C_1$-$C_6$-alkyl, $C_1$-$C_6$-haloalkyl or phenyl, wherein phenyl is unsubstituted or substituted with up to 5 substituents selected from halogen, $NO_2$, $C_1$-$C_6$-alkyl or $C_1$-$C_6$-alkoxy.

Very particular preference is given to compounds of formula (XII) wherein
L is Cl, Br or $OS(O)_2R^*$; and
$R^*$ is Me, $CF_3$, $C_4F_9$, phenyl or toluyl.

The molar ratio of the compound of formula (XI) to the compound of formula (XII) is generally in the range of 1:0.5-2, preferably in the range of 1:0.5-1.5, more preferably in the range of 1:0.8-1.2.

Examples of suitable bases are carbonates such as lithium carbonate, sodium carbonate, potassium carbonate, cesium carbonate, magnesium carbonate, calcium carbonate, barium carbonate; hydrogen carbonates such as lithium hydrogen carbonate, sodium hydrogen carbonate, potassium hydrogen carbonate; hydroxides such as lithium hydroxide, sodium hydroxide, potassium hydroxide, magnesium hydroxide, calcium hydroxide, barium hydroxide, aluminum hydroxide; oxides such as lithium oxide, sodium oxide, potassium oxide, magnesium oxide, calcium oxide, barium oxide, iron oxide, silver oxide; hydrides such as lithium hydride, sodium hydride, potassium hydride, calcium hydride; phosphates such as potassium phosphate, calcium phosphate; alkoxides such sodium, potassium or magnesium alkoxides; nitrogen-containing bases such as triethylamine, trimethylamine, N-ethyldiisopropylamine, triisopropylamine, ammonia, pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN).

Preferred bases include carbonates and hydrides.

Particularly preferred bases include potassium carbonate, cesium carbonate and sodium hydride.

The term base as used herein also includes mixtures of two or more, preferably two of the above compounds. Particular preference is given to the use of one base.

The molar ratio of the compound of formula (XI) to the base is generally in the range of 1:0.8-3, preferably in the range of 1:1-2, more preferably in the range of 1:1-1.5.

Preferably, the reaction of the compound of formula (XI) with the compound of formula (XII) in the presence of a base is carried out in a solvent.

Examples of suitable solvents are dipolar aprotic solvents such as N,N-dimethylformamide (DMF), N,N-dimethylacetamide (DMAc), 1-methyl-2-pyrrolidinone (NMP), 1,3-dimethyl-2-imidazolidinone (DMI), N,N'-dimethylpropylene urea (DMPU), dimethyl sulfoxide (DMSO), sulfolane, acetonitrile, benzonitrile, acetone, methyl ethyl ketone, methyl butyl ketone, methyl isobutyl ketone, cyclohexanone, nitromethane, nitroethane, nitrobenzene; esters such as ethyl acetate, butyl acetate, isobutyl acetate; ethers such as diethylether, dibutylether, tert-butyl methyl ether (TBME), 1,2-dimethoxyethane, tetrahydrofurane (THF), cyclopentyl methyl ether, 1,4-dioxane; alcohols such as methanol, ethanol, isopropanol, 1-butanol, 2-butanol, isobutanol, tert-butanol, hexafluoro isopropanol; halogenated hydrocarbons such as dichloromethane, dichloroethane, carbon tetrachloride; aliphatic hydrocarbons such as hexane, cyclohexane; aromatic hydrocarbons such as benzene, toluene, xylenes, mesitylene, chlorobenzene.

Preferred solvents include acetone, DMF, DMAc, 1,2-dimethoxyethane, DMI, dichloromethane, diethylether and THF.

Particularly preferred solvents include acetone, diethylether and THF.

The term solvent as used herein also includes mixtures of two or more of the above compounds.

The reaction of the compound of formula (XI) with the compound of formula (XII) in the presence of a base is generally carried out at a temperature in the range of from −40 to 80° C., preferably in the range of from −20 to 40° C., more preferably in the range of from 0 to 30° C.

Pests

Preferred animal pests are invertebrate pests.

The term "invertebrate pest" as used herein encompasses animal populations, such as arthropode pests, including insects and arachnids, as well as nematodes, which may attack plants thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The compounds of the formula I, their salts, and their N-oxides are in particular suitable for efficiently controlling arthropodal pests such as arachnids, myriapedes and insects as well as nematodes.

The compounds of the formula I are especially suitable for efficiently combating the following pests:

insects from the order of the lepidopterans (Lepidoptera), for example *Acronicta major, Adoxophyes orana, Aedia leucomelas, Agrotis* spp. such as *Agrotis fucosa, Agrotis segetum, Agrotis ipsilon; Alabama argillacea, Anticarsia gemmatalis, Anticarsia* spp., *Argyresthia conjugella, Autographa gamma, Barathra brassicae, Bucculatrix thurberiella, Bupalus piniarius, Cacoecia murinana, Cacoecia podana, Capua reticulana, Carpocapsa pomonella, Cheimatobia brumata, Chilo* spp. such as *Chilo suppressalis; Choristoneura fumiferana, Choristoneura occidentalis, Cirphis unipuncta, Clysia ambiguella, Cnaphalocerus* spp., *Cydia pomonella, Dendrolimus pini, Diaphania nitidalis, Diatraea grandiosella, Earias insulana, Elasmopalpus lignosellus, Ephestia cautella, Ephestia kuehniella, Eupoecilia ambiguella, Euproctis chrysorrhoea, Euxoa* spp., *Evetria bouliana, Feltia* spp. such as *Feltia subterranean; Galleria mellonella, Grapholitha funebrana, Grapholitha molesta, Helicoverpa* spp. such as *Helicoverpa armigera, Helicoverpa zea; Heliothis* spp. such as *Heliothis armigera, Heliothis virescens, Heliothis zea; Hellula undalis, Hibernia defoliaria, Hofmannophila pseudospretella, Homona magnanima, Hyphantria cunea, Hyponomeuta padella, Hyponomeuta malinellus, Keiferia lycopersicella, Lambdina fiscellaria, Laphygma* spp. such as *Laphygma exigua; Leucoptera coffeella, Leucoptera scitella, Lithocolletis blancardella, Lithophane antennata, Lobesia botrana, Loxagrotis albicosta, Loxostege sticticalis, Lymantria* spp. such as *Lymantria dispar, Lymantria monacha; Lyonetia clerkella, Malacosoma neustria, Mamestra* spp. such as *Mamestra brassicae; Mocis repanda, Mythimna separata, Orgyia pseudotsugata, Oria* spp., *Ostrinia* spp. such as *Ostrinia nubilalis; Oulema oryzae, Panolis flammea, Pectinophora* spp. such as *Pectinophora gossypiella; Peridroma saucia, Phalera bucephala, Phthorimaea* spp. such as *Phthorimaea operculella; Phyllocnistis citrella, Pieris* spp. such as *Pieris brassicae, Pieris rapae; Plathypena scabra, Plutella maculipennis, Plutella xylostella, Prodenia* spp., *Pseudaletia* spp., *Pseudoplusia includens, Pyrausta nubilalis, Rhyacio-* nia frustrana, Scrobipalpula absoluta, Sitotroga cerealella, Sparganothis pilleriana, Spodoptera spp. such as Spodoptera frugiperda, Spodoptera littoralis, Spodoptera litura; Thaumatopoea pityocampa, Thermesia gemmatalis, Tinea peffionella, Tineola bisselliella, Tortrix viridana, Trichoplusia spp. such as Trichoplusia ni; Tuta absoluta, and Zeiraphera canadensis, beetles (Coleoptera), for example Acanthoscehdes obtectus, Adoretus spp., Agelastica alni, Agrilus sinuatus, Agriotes spp. such as Agriotes fuscicollis, Agriotes lineatus, Agriotes obscurus; Amphimallus solstitialis, Anisandrus dispar, Anobium punctatum, Anomala rufocuprea, Anoplophora spp. such as Anoplophora glabripennis; Anthonomus spp. such as Anthonomus grandis, Anthonomus pomorum; Anthrenus spp., Aphthona euphoridae, Apogonia spp., Athous haemorrhoidalis, Atomaria spp. such as Atomaria linearis; Attagenus spp., Aulacophora femoralis, Blastophagus piniperda, Blitophaga undata, Bruchidius obtectus, Bruchus spp. such as Bruchus lentis, Bruchus pisorum, Bruchus rufimanus; Byctiscus betulae, Callosobruchus chinensis, Cassida nebulosa, Cerotoma trifurcata, Cetonia aurata, Ceuthorhynchus spp. such as Ceuthorhynchus assimilis, Ceuthorhynchus napi; Chaetocnema tibialis, Cleonus mendicus, Conoderus spp. such as Conoderus vespertinus; Cosmopolites spp., Costelytra zealandica, Crioceris asparagi, Cryptorhynchus lapathi, Ctenicera ssp. such as Ctenicera destructor; Curculio spp., Dectes texanus, Dermestes spp., Diabrotica spp. such as Diabrotica 12-punctata Diabrotica speciosa, Diabrotica longicomis, Diabrotica semipunctata, Diabrotica virgifera; Epilachna spp. such as Epilachna varivestis, Epilachna vigintioctomaculata; Epitrix spp. such as Epitrix hirtipennis; Eutinobothrus brasiliensis, Faustinus cubae, Gibbium psylloides, Heteronychus arator, Hylamorpha elegans, Hylobius abietis, Hylotrupes bajulus, Hypera brunneipennis, Hypera postica, Hypothenemus spp., Ips typographus, Lachnosterna consanguinea, Lema bilineata, Lema melanopus, Leptinotarsa spp. such as Leptinotarsa decemlineata; Limonius californicus, Lissorhoptrus oryzophilus, Lissorhoptrus oryzophilus, Lixus spp., Lyctus spp. such as Lyctus bruneus; Melanotus cornmunis, Meligethes spp. such as Meligethes aeneus; Melolontha hippocastani, Melolontha melolontha, Migdolus spp., Monochamus spp. such as Monochamus alternatus; Naupactus xanthographus, Niptus hololeucus, Oryctes rhinoceros, Oryzaephilus surinamensis, Otiorrhynchus sulcatus, Otiorrhynchus ovatus, Otiorrhynchus sulcatus, Oulema oryzae, Oxycetonia jucunda, Phaedon cochleariae, Phyllobius pyri, Phyllopertha horticola, Phyllophaga spp., Phyllotreta spp. such as Phyllotreta chrysocephala, Phyllotreta nemorum, Phyllotreta striolata; Phyllophaga spp., Phyllopertha horticola, Popiffia japonica, Premnotrypes spp., Psylliodes chrysocephala, Ptinus spp., Rhizobius ventralis, Rhizopertha dominica, Sitona lineatus, Sitophilus spp. such as Sitophilus granaria, Sitophilus zeamais; Sphenophorus spp. such as Sphenophorus levis; Sternechus spp. such as Sternechus subsignatus; Symphyletes spp., Tenebrio molitor, Tribolium spp. such as Tribolium castaneum; Trogoderma spp., Tychius spp., Xylotrechus spp., and Zabrus spp. such as Zabrus tenebrioides, flies, mosquitoes (Diptera), e.g. Aedes spp. such as Aedes aegypti, Aedes albopictus, Aedes vexans; Anastrepha ludens, Anopheles spp. such as Anopheles albimanus, Anopheles crucians, Anopheles freeborni, Anopheles gambiae, Anopheles leucosphyrus, Anopheles maculipennis, Anopheles minimus, Anopheles quadrimaculatus, Anopheles sinensis; Bibio hortulanus, Calliphora erythrocephala, Calliphora vicina, Cerafitis capitata, Ceratitis capitata, Chrysomyia spp. such as Chrysomya bezziana, Chrysomya hominivorax, Chrysomya macellaria; Chrysops atlanticus, Chrysops discalis, Chrysops silacea, Cochliomyia spp. such as Cochliomyia hominivorax; Contarinia spp. such as Contarinia sorghicola; Cordylobia anthropophaga, Culex spp. such as Culex nigripalpus, Culex pipiens, Culex quinquefasciatus, Culex tarsalis, Culex tritaeniorhynchus; Culicoides furens, Culiseta inornata, Culiseta melanura, Cuterebra spp., Dacus cucurbitae, Dacus oleae, Dasineura brassicae, Delia spp. such as Delia antique, Delia coarctata, Delia platura, Delia radicum; Dermatobia hominis, Drosophila spp., Fannia spp. such as Fannia canicularis; Gastraphilus spp. such as Gasterophilus intestinalis; Geomyza Tripunctata, Glossina fuscipes, Glossina morsitans, Glossina palpalis, Glossina tachinoides, Haematobia irritans, Haplodiplosis equestris, Hippelates spp., Hylemyia spp. such as Hylemyia platura; Hypoderma spp. such as Hypoderma lineata; Hyppobosca spp., Leptoconops torrens, Liriomyza spp. such as Liriomyza sativae, Liriomyza trifolii; Lucilia spp. such as Lucilia caprina, Lucilia cuprina, Lucilia sericata; Lycoria pectoralis, Mansonia titillanus, Mayetiola spp. such as Mayetiola destructor; Musca spp. such as Musca autumnalis, Musca domestica; Muscina stabulans, Oestrus spp. such as Oestrus ovis; Opomyza florum, Oscinella spp. such as Oscinella frit; Pegomya hysocyami, Phlebotomus argentipes, Phorbia spp. such as Phorbia antiqua, Phorbia brassicae, Phorbia coarctata; Prosimulium mixtum, Psila rosae, Psorophora columbiae, Psorophora discolor, Rhagoletis cerasi, Rhagoletis pomonella, Sarcophaga spp. such as Sarcophaga haemorrhoidalis; Simulium vittatum, Stomoxys spp. such as Stomoxys calcitrans; Tabanus spp. such as Tabanus atratus, Tabanus bovinus, Tabanus lineola, Tabanus similis; Tannia spp., Tipula oleracea, Tipula paludosa, and Wohlfahrtia spp., thrips (Thysanoptera), e.g. Baliothrips biformis, Dichromothrips corbetti, Dichromothrips ssp., Enneothrips flavens, Frankliniella spp. such as Frankliniella fusca, Frankliniella occidentalis, Frankliniella tritici; Heliothrips spp., Hercinothrips femoralis, Kakothrips spp., Rhipiphorothrips cruentatus, Scirtothrips spp. such as Scirtothrips citri; Taeniothrips cardamoni, Thrips spp. such as Thrips oryzae, Thrips palmi, Thrips tabaci;

termites (Isoptera), e.g. Calotermes flavicollis, Coptotermes formosanus, Heterotermes aureus, Heterotermes longiceps, Heterotermes tenuis, Leucotermes flavipes, Odontotermes spp., Reticulitermes spp. such as Reticulitermes speratus, Reticulitermes flavipes, Reticulitermes grassei, Reticulitermes lucifugus, Reticulitermes santonensis, Reticulitermes virginicus; Termes natalensis, cockroaches (Blattaria-Blattodea), e.g. Acheta domesticus, Blatta orientalis, Blattella asahinae, Blattella germanica, Gryllotalpa spp., Leucophaea maderae, Locusta spp., Melanoplus spp., Periplaneta americana, Periplaneta australasiae, Periplaneta brunnea, Periplaneta fuligginosa, Periplaneta japonica, bugs, aphids, leafhoppers, whiteflies, scale insects, cicadas (Hemiptera), e.g. Acrosternum spp. such as Acrosternum hilare; Acyrthosipon spp. such as Acyrthosiphon onobrychis, Acyrthosiphon pisum; Adelges laricis, Aeneolamia spp., Agonoscena spp., Aleurodes spp., Aleurolobus barodensis, Aleurothrixus spp., Amrasca spp., Anasa tristis, Antestiopsis spp., Anuraphis cardui, Aonidiella spp., Aphanostigma piri, Aphidula nasturtii, Aphis spp. such as Aphis fabae, Aphis forbesi, Aphis gossypii, Aphis grossulariae, Aphis pomi, Aphis sambuci, Aphis schneideri, Aphis spiraecola; Arboridia apicalis, Arilus critatus, Aspidiella spp., Aspidiotus spp., Atanus spp., Aulacorthum solani, Bemisia spp. such as *Bemisia argentifolii, Bemisia tabaci; Blissus* spp. such as *Blissus leucopterus; Brachycaudus cardui, Brachycaudus helichrysi, Brachycaudus persicae, Brachycaudus prunicola, Brachycolus* spp., *Brevicoryne brassicae, Calligypona marginata, Calocoris* spp., *Campylomma livida, Capitophorus horni, Carneocephala fulgida, Cavelerius* spp., *Ceraplastes* spp., *Ceratovacuna lanigera, Cercopidae, Cerosipha gossypii, Chaetosiphon fragaefolii, Chionaspis tegalensis, Chlorita Chromaphis juglandicola, Chrysomphalus ficus, Cicadulina mbila, Cimex* spp. such as *Cimex hemipterus, Cimex lectularius; Coccomytilus halli, Coccus* spp., *Creontiades dilutus, Cryptomyzus ribis, Cryptomyzus ribis, Cyrtopeltis notatus, Dalbulus* spp., *Dasynus piperis, Dialeurades* spp., *Diaphorina* spp., *Diaspis* spp., *Dichelops furcatus, Diconocoris hewetti, Doralis* spp., *Dreyfusia nordmannianae, Dreyfusia piceae, Drosicha* spp., *Dysaphis* spp. such as *Dysaphis plantaginea, Dysaphis pyri, Dysaphis radicola; Dysaulacorthum pseudosolani, Dysdercus* spp. such as *Dysdercus cingulatus, Dysdercus intermedius; Dysmicoccus* spp., *Empoasca* spp. such as *Empoasca fabae, Empoasca solana; Eriosoma* spp., *Erythroneura* spp., *Eurygaster* spp. such as *Eurygaster integriceps; Euscelis bilobatus, Euschistus* spp. such as *Euschistuos heros, Euschistus impictiventris, Euschistus servus; Geococcus coffeae, Halyomorpha* spp. such as *Halyomorpha halys; Heliopeltis* spp., *Homalodisca coagulata, Horcias nobilellus, Hyalopterus pruni, Hyperomyzus lactucae, Icerya* spp., *Idiocerus* spp., *Idioscopus* spp., *Laodelphax striatellus, Lecanium* spp., *Lepidosaphes* spp., *Leptocorisa* spp., *Leptoglossus phyllopus, Lipaphis erysimi, Lygus* spp. such as *Lygus hesperus, Lygus lineolaris, Lygus pratensis; Macropes excavatus, Macrosiphum* spp. such as *Macrosiphum rosae, Macrosiphum avenae, Macrosiphum euphorbiae; Mahanarva fimbriolata, Megacopta cribraria, Megoura viciae, Melanaphis pyrarius, Melanaphis sacchari, Metcafiella* spp., *Metopolophium dirhodum, Miridae* spp., *Monellia costalis, Monelliopsis pecanis, Myzus* spp. such as *Myzus ascalonicus, Myzus cerasi, Myzus persicae, Myzus varians; Nasonovia ribis-nigri, Nephotettix* spp. such as *Nephotettix malayanus, Nephotettix nigropictus, Nephotettix parvus, Nephotettix virescens; Nezara* spp. such as *Nezara viridula; Nilaparvata lugens, Oebalus* spp., *Oncometopia* spp., *Orthezia praelonga, Parabemisia myricae, Paratrioza* spp., *Parlatoria* spp., *Pemphigus* spp. such as *Pemphigus bursarius; Pentomidae, Peregrinus maidis, Perkinsiella saccharicida, Phenacoccus* spp., *Phloeomyzus passerinii, Phorodon humuii, Phylloxera* spp., *Piesma quadrata, Piezodorus* spp. such as *Piezodorus guildinii, Pinnaspis aspidistrae, Planococcus* spp., *Protopulvinaria pyriformis, Psallus seriatus, Pseudacysta persea, Pseudaulacaspis pentagona, Pseudococcus* spp. such as *Pseudococcus comstocki; Psylla* spp. such as *Psylla mali, Psylla piri; Pteromalus* spp., *Pyrilla* spp., *Quadraspidiotus* spp., *Quesada gigas, Rastrococcus* spp., *Reduvius senilis, Rhodnius* spp., *Rhopalomyzus ascalonicus, Rhopalosiphum* spp. such as *Rhopalosiphum pseudobrassicas, Rhopalosiphum insertum, Rhopalosiphum maidis, Rhopalosiphum padi; Sagatodes* spp., *Sahlbergella singularis, Saissetia* spp., *Sappaphis mala, Sappaphis mall, Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Stephanitis nashi, Stictocephala festina, Tenalaphara malayensis, Thyanta* spp. such as *Thyanta perditor; Tibraca* spp., *Tinocallis caryaefoliae, Tomaspis* spp., *Toxoptera* spp. such as *Toxoptera aurantii; Trialeurodes* spp.

such as *Trialeurodes vaporariorum; Triatoma* spp., *Trioza* spp., *Typhlocyba* spp., *Unaspis* spp. such as *Unaspis yanonensis*; and *Viteus vitifolii*, ants, bees, wasps, sawflies (Hymenoptera), e.g. *Athalia rosae, Atta capiguara, Atta cephalotes, Atta cephalotes, Atta laevigata, Atta robusta, Atta sexdens, Atta texana, Bombus* spp., *Camponotus floridanus, Crematogaster* spp., *Dasymutilla occidentalis, Diprion* spp., *Dolichovespula maculata, Hoplocampa* spp. such as *Hoplocampa minuta, Hoplocampa testudinea; Lasius* spp. such as *Lasius niger, Linepithema humile, Monomorium pharaonis, Paravespula germanica, Paravespula pennsylvanica, Paravespula vulgaris, Pheidole megacephala, Pogonomyrmex barbatus, Pogonomyrmex califomicus, Polistes rubiginosa, Solenopsis geminata, Solenopsis invicta, Solenopsis richteri, Solenopsis xyloni, Vespa* spp. such as *Vespa crabro*, and *Vespula squamosa*, crickets, grasshoppers, locusts (Orthoptera), e.g. *Acheta domestica, Calliptamus italicus, Chortoicetes terminifera, Dociostaurus maroccanus, Gryllotalpa africana, Gryllotalpa gryllotalpa, Hieroglyphus daganensis, Kraussaria angulifera, Locusta migratoria, Locustana pardalina, Melanoplus bivittatus, Melanoplus femurrubrum, Melanoplus mexicanus, Melanoplus sanguinipes, Melanoplus spretus, Nomadacris septemfasciata, Oedaleus senegalensis, Schistocerca americana, Schistocerca gregaria, Tachycines asynamorus*, and *Zonozerus variegatus*, arachnids (Arachnida), such as acari, e.g. of the families Argasidae, Ixodidae and Sarcoptidae, such as *Amblyomma* spp. (e.g. *Amblyomma americanum, Amblyomma variegatum, Amblyomma maculatum*), *Argas* spp. (e.g. *Argas persicus*), *Boophilus* spp. (e.g. *Boophilus annulatus, Boophilus decoloratus, Boophilus microplus*), *Dermacentor silvarum, Dermacentor andersoni, Dermacentor variabilis, Hyalomma* spp. (e.g. *Hyalomma truncatum*), *Ixodes* spp. (e.g. *Ixodes ricinus, Ixodes rubicundus, Ixodes scapularis, Ixodes holocyclus, Ixodes pacificus*), *Ornithodorus* spp. (e.g. *Ornithodorus moubata, Ornithodorus hermsi, Ornithodorus turicata*), *Ornithonyssus bacoti, Otobius megnini, Dermanyssus gallinae, Psoroptes* spp. (e.g. *Psoroptes ovis*), *Rhipicephalus* spp. (e.g. *Rhipicephalus sanguineus, Rhipicephalus appendiculatus, Rhipicephalus evertsi*), *Rhizoglyphus* spp., *Sarcoptes* spp. (e.g. *Sarcoptes scabiei*), and *Eriophyidae* spp. such as *Acaria sheldoni, Aculops* spp. (e.g. *Aculops pelekassi*) *Aculus* spp. (e.g. *Aculus schlechtendali*), *Epitrimerus pyri, Phyllocoptruta oleivora* and *Eriophyes* spp. (e.g. *Eriophyes sheldoni*); *Tarsonemidae* spp. such as *Hemitarsonemus* spp., *Phytonemus pallidus* and *Polyphagotarsonemus latus, Stenotarsonemus* spp.; *Tenuipalpidae* spp. such as *Brevipalpus* spp. (e.g. *Brevipalpus phoenicis*); *Tetranychidae* spp. such as *Eotetranychus* spp., *Eutetranychus* spp., *Oligonychus* spp., *Tetranychus cinnabarinus, Tetranychus kanzawai, Tetranychus pacificus, Tetranychus telarius* and *Tetranychus urticae; Bryobia praetiosa, Panonychus* spp. (e.g. *Panonychus ulmi, Panonychus citri*), *Metatetranychus* spp. and *Oligonychus* spp. (e.g. *Oligonychus pratensis*), *Vasates lycopersici*; Araneida, e.g. *Latrodectus mactans*, and *Loxosceles reclusa*. And *Acarus siro, Chorioptes* spp., *Scorpio maurus* fleas (Siphonaptera), e.g. *Ceratophyllus* spp., *Ctenocephalides felis, Ctenocephalides canis, Xenopsylla cheopis, Pulex irritans, Tunga penetrans*, and *Nosopsyllus fasciatus*, silverfish, firebrat (Thysanura), e.g. *Lepisma saccharina* and *Thermobia domestica*, centipedes (Chilopoda), e.g. *Geophilus* spp., *Scutigera* spp. such as *Scutigera coleoptrata*;

millipedes (Diplopoda), e.g. *Blaniulus guttulatus, Narceus* spp.,

Earwigs (Dermaptera), e.g. *forficula auricularia,* lice (Phthiraptera), e.g. *Damalinia* spp., *Pediculus* spp. such as *Pediculus humanus capitis, Pediculus humanus corporis; Pthirus pubis, Haematopinus* spp. such as *Haematopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., springtails (Collembola), e.g. *Onychiurus* ssp. such as *Onychiurus armatus,*

They are also suitable for controlling nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species such as *Aphelenchoides besseyi*; Sting nematodes, *Belonolaimus longicaudatus* and other *Belonolaimus* species; Pine nematodes, *Bursaphelenchus lignicolus* Mamiya et Kiyohara, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus muiticinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus brachyurus, Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species such as *Tylenchulus semipenetrans*; Dagger nematodes, *Xiphinema* species; and other plant parasitic nematode species.

Examples of further pest species which may be controlled by compounds of formula (I) include: from the class of the Bivalva, for example, *Dreissena* spp.; from the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuellebomi, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*; from the order of the Isopoda, for example, *Armadillidium vulgare, Oniscus asellus, Porcellio scaber*; from the order of the Symphyla, for example, *Scutigerella immaculata.*

Further examples of pest species which may be controlled by compounds of formula (I) include: *Anisoplia austriaca, Apamea* spp., *Austroasca viridigrisea, Baliothrips biformis, Caenorhabditis elegans, Cephus* spp., *Ceutorhynchus napi, Chaetocnema aridula, Chilo auricilius, Chilo indicus, Chilo polychrysus, Chortiocetes terminifera, Cnaphalocroci medinalis, Cnaphalocrosis* spp., *Colias eurytheme, Collops* spp., *Cornitermes cumulans, Creontiades* spp., *Cyclocephala* spp., *Dalbulus maidis, Deraceras reticulatum, Diatrea saccharalis, Dichelops furcatus, Dicladispa armigera, Diloboderus* spp. such as *Diloboderus abderus; Edessa* spp., *Epinotia* spp., *Formicidae, Geocoris* spp., *Globitermes sulfureus, Gryllotalpidae, Halotydeus destructor, Hipnodes bicolor, Hydrellia philippina, Julus* spp., *Laodelphax* spp., *Leptocorsia acuta, Leptocorsia oratorius, Liogenys fuscus, Lucillia* spp., *Lyogenys fuscus, Mahanarva* spp., *Maladera matrida, Marasmia* spp., *Mastotermes* spp., *Mealybugs, Megascelis ssp, Metamasius hemipterus, Microtheca* spp., *Mocis latipes, Murgantia* spp., *Mythemina separata, Neocapritermes opacus, Neocapritermes parvus, Neomegalotomus* spp., *Neotermes* spp., *Nymphula depunctalis, Oebalus pugnax, Orseolia* spp. such as *Orseolia oryzae; Oxycaraenus hyalinipennis, Plusia* spp., *Pomacea canaliculata, Procornitermes ssp, Procornitermes triacifer, Psylloides* spp., *Rachiplusia* spp., *Rhodopholus* spp., *Scaptocoris castanea, Scaptocoris* spp., *Scirpophaga* spp. such as *Scirpophaga incertulas, Scirpophaga innotata; Scotinophara* spp. such as *Scotinophara coarctata; Sesamia* spp. such as *Sesamia inferens, Sogaella frucifera, Solenapsis geminata, Spissistilus* spp., *Stalk borer, Stenchaetothrips biformis, Steneotarsonemus spinki, Sylepta derogata, Telehin licus, Trichostrongylus* spp.

Compounds of the formula I are particularly useful for controlling insects, preferably sucking or piercing insects such as insects from the genera Thysanoptera, Diptera and Hemiptera, in particular the following species:

Thysanoptera: *Frankliniella fusca, Frankliniella occidentalis, Frankliniella tritici, Scirtothrips citri, Thrips oryzae, Thrips palmi* and *Thrips tabaci,*

Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii,*

*Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphum rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla pini, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii.*

Hemiptera, in particular *Nezara* spp. such as *Nezara viridula.*

Compounds of the formula I are particularly useful for controlling insects of the orders Hemiptera and Thysanoptera.

Compounds of the formula I are particularly useful for controlling Hemiptera, in particular *Nezara* spp. such as *Nezara viridula.*

Formulations

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling harmful pests on cultivated plants or in the protection of materials and which does not result in a substantial damage to the treated plants. Such an amount can vary in a broad range and is dependent on various factors, such as the animal pests species to be controlled, the treated cultivated plant or material, the climatic conditions and the specific compound I used.

The compounds I, their salts, and their N-oxides can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Mono-graph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g.
cereal meal, tree bark meal, wood meal, nutshell meal, and mixtures thereof.

Suitable surfactants are surface-active compounds, such as anionic, cationic, nonionic and am-photeric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsul-fonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanofer-rate) and organic colorants (e.g. alizarin-, azo- and phthalocyanine colorants).

Suitable tackifiers or binders are polyvinylpyrrolidons, polyvinylacetates, polyvinyl alcohols, pol-yacrylates, biological or synthetic waxes, and cellulose ethers.

Examples for composition types and their preparation are:
i) Water-Soluble Concentrates (SL, LS)
   10-60 wt % of a compound I according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.
ii) Dispersible Concentrates (DC)
   5-25 wt % of a compound I according to the invention and 1-10 wt % dispersant (e.g. poly-vinylpyrrolidone) are dissolved in organic solvent (e.g. cyclohexanone) ad 100 wt %. Dilution with water gives a dispersion.
iii) Emulsifiable Concentrates (EC)
   15-70 wt % of a compound I according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.
iv) Emulsions (EW, EO, ES)
   5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.
v) Suspensions (SC, OD, FS)
   In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.
vi) Water-Dispersible Granules and Water-Soluble Granules (WG, SG)
   50-80 wt % of a compound I according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.
vii) Water-Dispersible Powders and Water-Soluble Powders (WP, SP, WS)
   50-80 wt % of a compound I according to the invention are ground in a rotor-stator mill with addition of 1-5 wt % dispersants (e.g. sodium lignosulfonate), 1-3 wt % wetting agents (e.g. alcohol ethoxyiate) and solid carrier (e.g. silica gel) ad 100 wt %. Dilution with water gives a stable dispersion or solution of the active substance.
viii) Gel (GW, GF)
   In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.
iv) Microemulsion (ME)
   5-20 wt % of a compound I according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.
iv) Microcapsules (CS)
   An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth) acrylate microcapsules.

Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dustable Powders (DP, DS)
1-10 wt % of a compound I according to the invention are ground finely and mixed intimately with solid carrier (e.g. finely divided kaolin) ad 100 wt %.

x) Granules (GR, FG)
0.5-30 wt % of a compound I according to the invention is ground finely and associated with solid carrier (e.g. silicate) ad 100 wt %. Granulation is achieved by extrusion, spray-drying or the fluidized bed.

xi) Ultra-Low Volume Liquids (UL)
1-50 wt % of a compound I according to the invention are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds I, may be mixed by the user in a spray tank and further auxiliaries and additives may be added, if appropriate.

In a further embodiment, either individual components of the composition according to the invention or partially premixed components, e.g. components comprising compounds I, can be applied jointly (e.g. after tank mix) or consecutively.

Mixtures

According to one embodiment of the present invention, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds I and/or active substances from the groups M.1 to M.UN.X or F.I to F.XII, may be mixed by the user in a spray tank and further auxiliaries and additives may be added, if appropriate.

In a further embodiment, either individual components of the composition according to the invention or partially premixed components, e.g. components comprising compounds I and/or active substances from the groups M.1 to M.UN.X or F.I to F.XII, can be applied jointly (e.g. after tank mix) or consecutively.

The following list M of pesticides, grouped and numbered according the Mode of Action Classification of the Insecticide Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifosmethyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemetonmethyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or the compounds M.4A.1: 1-[(6-chloro-3-pyridinyl)methyl]-2,3,5,6,7,8-hexahydro-9-nitro-(5S,8R)-5,8-Epoxy-1H-imidazo[1,2-a]azepine; or M.4A.2: 1-[(6-chloro-3-pyridyl)methyl]-2-nitro-1-[(E)-pentylideneamino]guanidine; or M4.A.3: 1-[(6-chloro-3-pyridyl)methyl]-7-methyl-8-nitro-5-propoxy-3,5,6,7-tetrahydro-2H-imidazo[1,2-a]pyridine;

or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example

M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or M.22B metaflumizone, or M.22C 1-[(E)-[2-(4-cyanophenyl)-1-[3-(trifluoromethyl)phenyl]ethylidene]amino]-3-[4-(difluoromethoxy)phenyl]urea;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide.

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):

M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

M.28.5i) N-[2-(5-amino-1,3,4-thiadiazol-2-yl)-4-chloro-6-methyl-phenyl]-5-bromo-2-(3-chloro-2-pyridyl)pyrazole-3-carboxamide;

M.28.5j) 5-chloro-2-(3-chloro-2-pyridyl)-N-[2,4-dichloro-6-[(1-cyano-1-methyl-ethyl)carbamoyl]phenyl]pyrazole-3-carboxamide;

M.28.5k) 5-bromo-N-[2,4-dichloro-6-(methylcarbamoyl)phenyl]-2-(3,5-dichloro-2-pyridyl)pyrazole-3-carboxamide;

M.28.5l) N-[2-(tert-butylcarbamoyl)-4-chloro-6-methyl-phenyl]-2-(3-chloro-2-pyridyl)-5-(fluoromethoxy)pyrazole-3-carboxamide; or a compound selected from M.28.6 N2-(1-cyano-1-methyl-ethyl)-N1-(2,4-dimethylphenyl)-3-iodo-phthalamide; or M.28.7 3-chloro-N2-(1-cyano-1-methyl-ethyl)-N1-(2,4-dimethylphenyl)phthalamide;

M.UN.X insecticidal active compounds of unknown or uncertain mode of action, as for example afidopyropen, azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, pyflubumide or the compounds M.UN.X.1: 4-[5-(3,5-Dichloro-phenyl)-5-trifluoromethyl-4,5-dihydro-isoxazol-3-yl]-2-methyl-N-[(2,2,2-trifluoroethylcarbamoyl)-methyl]-benzamide, or the compound M.UN.X.2: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide, or the compound M.UN.X.3: 11-(4-chloro-2,6-dimethylphenyl)-12-hydroxy-1,4-dioxa-9-azadispiro[4.2.4.2]-tetradec-11-en-10-one, or the compound M.UN.X.4: 3-(4'-fluoro-2,4-dimethylbiphenyl-3-yl)-4-hydroxy-8-oxa-1-azaspiro[4.5]dec-3-en-2-one, or the compound M.UN.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, 1-1582); or M.UN.X.6; a compound selected from the group of M.UN.X.6a) (E/Z)—N-[1-[(6-chloro-3-pyridyl)methyl]-2-pyridylidene]-2,2,2-trifluoro-acetamide;

M.UN.X.6b) (E/Z)—N-[1-[(6-chloro-5-fluoro-3-pyridyl)methyl]-2-pyridylidene]-2,2,2-trifluoro-acetamide;

M.UN.X.6c) (E/Z)-2,2,2-trifluoro-N-[1-[(6-fluoro-3-pyridyl)methyl]-2-pyridylidene]acetamide;

M.UN.X.6d) (E/Z)—N-[1-[(6-bromo-3-pyridyl)methyl]-2-pyridylidene]-2,2,2-trifluoro-acetamide;

M.UN.X.6e) (E/Z)—N-[1-[(6-chloro-3-pyridyl)ethyl]-2-pyridylidene]-2,2,2-trifluoro-acetamide;

M.UN.X.6f) (E/Z)—N-[1-[(6-chloro-3-pyridyl)methyl]-2-pyridylidene]-2,2-difluoro-acetamide;

M.UN.X.6g) (E/Z)-2-chloro-N-[1-[(6-chloro-3-pyridyl)methyl]-2-pyridylidene]-2,2-difluoro-acetamide;

M.UN.X.6h) (E/Z)—N-[1-[(2-chloropyrimidin-5-yl)methyl]-2-pyridylidene]-2,2,2-trifluoro-acetamide and M.UN.X.6i) (E/Z)—N-[1-[(6-chloro-3-pyridyl)methyl]-2-pyridylidene]-2,2,3,3,3-pentafluoropropanamide.); or of the compounds M.UN.X.7: 3-[3-chloro-5-(trifluoromethyl)phenyl]-4-oxo-1-(pyrimidin-5-ylmethyl)pyrido[1,2-a]pyrimidin-1-ium-2-olate; or M.UN.X.8: 8-chloro-N-[2-chloro-5-methoxyphenyl)sulfonyl]-6-trifluoromethyl)-imidazo[1,2-a]pyridine-2-carboxamide; or M.UN.X.9: 4-[5-(3,5-dichlorophenyl)-5-(trifluoromethyl)-4H-isoxazol-3-yl]-2-methyl-N-(1-oxothietan-3-yl)benzamide; or M.UN.X.10: 5-[3-[2,6-dichloro-4-(3,3-dichloroallyloxy)phenoxy]propoxy]-1H-pyrazole.

The commercially available compounds of the group M listed above may be found in The Pesticide Manual, 15th Edition, C. D. S. Tomlin, British Crop Protection Council (2011) among other publications.

The quinoline derivative flometoquin is shown in WO2006/013896. The aminofuranone compounds flupyradifurone is known from WO 2007/115644. The sulfoximine compound sulfoxaflor is known from WO2007/149134. The pyrethroid momfluorothrin is known from U.S. Pat. No. 6,908,945. The pyrazole acaricide pyflubumide is known from WO2007/020986. The isoxazoline compounds have been described likewise M.UN.X.1 in WO2005/085216, M.UN.X.2 in WO2009/002809 and in WO2011/149749 and the isoxazoline M.UN.X.9 in WO2013/050317. The pyripyropene derivative afidopyropen has been described in WO 2006/129714. The spiroketal-substituted cyclic ketoenol derivative M.UN.X.3 is known from WO2006/089633 and the biphenyl-substituted spirocyclic ketoenol derivative M.UN.X.4 from WO2008/067911. Finally triazoylphenylsulfide like M.UN.X.5 have been described in WO2006/043635 and biological control agents on basis of *bacillus firmus* in WO2009/124707. The neonicotionids 4A.1 is known from WO20120/069266 and WO2011/06946, the M.4.A.2 from WO2013/003977, the M4.A.3. from WO2010/069266. The Metaflumizone analogue M.22C is described in CN 10171577. The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5a) to M.28.5h) can be prepared as described in WO 2007/006670, WO2013/024009 and WO2013/024010, the anthranilamide M.28.5i) is described in WO2011/085575, the M.28.5j) in WO2008/134969, the M.28.5k) in US2011/046186 and the M.28.5l) in WO2012/034403. The diamide compounds M.28.6 and M.28.7 can be found in CN102613183. The compounds M.UN.X.6a) to M.UN.X.6i) listed in M.UN.X.6 have been described in WO2012/029672. The mesoionic antagonist compound M.UN.X.7 was described in WO2012/092115, the nematicide M.UN.X.8 in WO2013/055584 and the Pyridalyl-type analogue M.UN.X.10 in WO2010/060379.

The following list of active fungicidal substances, in conjunction with which the compounds according to the invention can be used, is intended to illustrate the possible combinations but does not limit them:

F.I) Respiration inhibitors
F.I-1) Inhibitors of complex III at Qo site (e.g. strobilurins) strobilurins: azoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, methyl (2-chloro-5 [1-(3-methylbenzyloxyimino)ethyl]benzyl)carbamate and 2 (2-(3-(2,6-dichlorophenyl)-1-methyl-allylideneaminooxymethyl)-phenyl)-2-methoxyimino-N methylacetamide;
oxazolidinediones and imidazolinones: famoxadone, fenamidone;
F.I-2) Inhibitors of complex II (e.g. carboxamides):
carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;
F.I-3) Inhibitors of complex III at Qi site: cyazofamid, amisulbrom;
F.I-4) Other respiration inhibitors (complex I, uncouplers) diflumetorim; tecnazen; ferimzone; ametoctradin; silthiofam;
nitrophenyl derivates: binapacryl, dinobuton, dinocap, fluazinam, nitrthal-isopropyl, organometal compounds: fentin salts, such as fentin-acetate, fentin chloride or fentin hydroxide;
F.II) Sterol biosynthesis inhibitors (SBI fungicides)
F.II-1) C14 demethylase inhibitors (DMI fungicides, e.g. triazoles, imidazoles) triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole;
imidazoles: imazalil, pefurazoate, oxpoconazole, prochloraz, triflumizole;
pyrimidines, pyridines and piperazines: fenarimol, nuarimol, pyrifenox, triforine;
F.II-2) Delta14-reductase inhitors (Amines, e.g. morpholines, piperidines) morpholines: aldimorph, dodemorph, dodemorph-acetate, fenpropimorph, tridemorph; piperidines: fenpropidin, piperalin; spiroketalamines: spiroxamine;
F.II-3) Inhibitors of 3-keto reductase: hydroxyanilides: fenhexamid;
F.III) Nucleic acid synthesis inhibitors
F.III-1) RNA, DNA synthesis
phenylamides or acyl amino acid fungicides: benalaxyl, benalaxyl-M, kiralaxyl, metalaxyl, metalaxyl-M (mefenoxam), ofurace, oxadixyl;
isoxazoles and iosothiazolones: hymexazole, octhilinone;
F.III-2) DNA topisomerase inhibitors: oxolinic acid;
F.III-3) Nucleotide metabolism (e.g. adenosin-deaminase) hydroxy (2-amino)-pyrimidines: bupirimate;
F.IV) Inhibitors of cell division and or cytoskeleton
F.IV-1) Tubulin inhibitors: benzimidazoles and thiophanates: benomyl, carbendazim, fuberidazole, thiabendazole, thiophanate-methyl;
triazolopyrimidines: 5-chloro-7 (4-methylpiperidin-1-yl)-6-(2,4,6-trifluorophenyl)[1,2,4]triazolo[1,5 a]pyrimidine
F.IV-2) Other cell division inhibitors
benzamides and phenyl acetamides: diethofencarb, ethaboxam, pencycuron, fluopicolide, zoxamide;
F.IV-3) Actin inhibitors: benzophenones: metrafenone;
F.V) Inhibitors of amino acid and protein synthesis
F.V-1) Mmethionine synthesis inhibitors (anilino-pyrimidines)
anilino-pyrimidines: cyprodinil, mepanipyrim, nitrapyrin, pyrimethanil;
F.V-2) Protein synthesis inhibitors (anilino-pyrimidines)
antibiotics: blasticidin-S, kasugamycin, kasugamycin hydrochloride-hydrate, mildiomycin, streptomycin, oxytetracyclin, polyoxine, validamycin A;
F.VI) Signal transduction inhibitors
F.VI-1) MAP/Histidine kinase inhibitors (e.g. anilino-pyrimidines)
dicarboximides: fluoroimid, iprodione, procymidone, vinclozolin;
phenylpyrroles: fenpiclonil, fludioxonil;
F.VI-2) G protein inhibitors: quinolines: quinoxyfen;
F.VII) Lipid and membrane synthesis inhibitors
F.VII-1) Phospholipid biosynthesis inhibitors
organophosphorus compounds: edifenphos, iprobenfos, pyrazophos;
dithiolanes: isoprothiolane;
F.VII-2) Lipid peroxidation
aromatic hydrocarbons: dicloran, quintozene, tecnazene, tolclofos-methyl, biphenyl, chloroneb, etridiazole;
F.VII-3) Carboxyl acid amides (CAA fungicides)
cinnamic or mandelic acid amides: dimethomorph, flumorph, mandiproamid, pyrimorph; valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl) ester;
F.VII-4) Compounds affecting cell membrane permeability and fatty acides carbamates: propamocarb, propamocarb-hydrochlorid F.VIII) Inhibitors with Multi Site Action
F.VIII-1) Inorganic active substances: Bordeaux mixture, copper acetate, copper hydroxide, copper oxychloride, basic copper sulfate, sulfur;
F.VIII-2) Thio- and dithiocarbamates: ferbam, mancozeb, maneb, metam, methasulphocarb, metiram, propineb, thiram, zineb, ziram;
F.VIII-3) Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
F.VIII-4) Guanidines: guanidine, dodine, dodine free base, guazatine, guazatine-acetate, iminoctadine, iminoctadine-triacetate, iminoctadine-tris(albesilate);
F.VIII-5) Ahtraquinones: dithianon;
F.IX) Cell wall synthesis inhibitors
F.IX-1) Inhibitors of glucan synthesis: validamycin, polyoxin B;
F.IX-2) Melanin synthesis inhibitors: pyroquilon, tricyclazole, carpropamide, dicyclomet, fenoxanil;
F.X) Plant defence inducers
F.X-1) Salicylic acid pathway: acibenzolar-S-methyl;
F.X-2) Others: probenazole, isotianil, tiadinil, prohexadione-calcium;
phosphonates: fosetyl, fosetyl-aluminum, phosphorous acid and its salts;
F.XI) Unknown mode of action:
bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-ylamide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetra-hydronaphthalen-1-yl]-4-thiazolecarboxamide, 3-[5-(4-chloro-phenyl)-2,3-dimethyl-isoxazolidin-3 yl]-pyridine, 3-[5-(4-methyl-phenyl)-2,3-dimethyl-isoxazolidin-3-yl]-pyridine, 5-amino-2-isopropyl-3-oxo-4-ortho-tolyl-2,3-dihydro-pyrazole-1 carbothioic acid S-allyl ester, N-(6-methoxy-pyridin-3-yl) cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;
F.XI) Growth regulators:
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;
F.XII) Biological control agents
antifungal biocontrol agents: *Bacillus substilis* strain with NRRL No. B-21661 (e.g. RHAPSODY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), *Ulocladium oudemansii* (e.g. the product BOTRY-ZEN from BotriZen Ltd., New Zealand), Chitosan (e.g. ARMOUR-ZEN from BotriZen Ltd., New Zealand).
Applications The animal pest, i.e. the insects, arachnids and nematodes, the plant, soil or water in which the plant is growing can be contacted with the present compounds of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of *durum* and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

The compounds of the present invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound I.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat Protoc. 2007; 2(5):1225-35, Curr Opin Chem Biol. 2006 October; 10(5):487-91. Epub 2006 Aug. 28, Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (*Diptera*), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitoes, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g in spray cans), oil sprays or pump sprays are highly suitable for the non-professional user for controlling pests such as flies, fleas, ticks, mosquitoes or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedling's roots and shoots from insects, in particular from soil and foliar insects, said method comprising contacting the seeds before sowing and/or after pregermination with a compound of the general formula I or a salt or N-oxide thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of *durum* and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

In addition, the active compound may also be used for the treatment of seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typically, a FS formulation may comprise 1-800 g/l of active ingredient, 1-200 g/l Surfactant, 0 to 200 g/l anti-freezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyieneamines, polyethyleneamides and polyethyieneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, or an N-oxide of I as defined herein. The amount of the compound I, or the agriculturally useful salt thereof, or the N-oxide thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula I or veterinarily acceptable salts or N-oxides thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or veterinarily acceptable salts or N-oxides thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or veterinarily acceptable salts or N-oxides thereof or a composition comprising it.

The invention also provides a process for the preparation of a composition for treating, controlling, preventing or protecting animals against infestation or infection by parasites which comprises a parasiticidally effective amount of a compound of formula I or veterinarily acceptable salts or N-oxides thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or veterinarily acceptable salts or N-oxides thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or veterinarily acceptable salts or N-oxides thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or veterinarily acceptable salts or N-oxides thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides felis, Ctenocephaiides canis, Xenopsylla cheopis, Pulex irritans, Tunga penetrans,* and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (*Diptera*), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp. a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders *Diptera,* Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intramural, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

The invention is illustrated by the following examples without being limited thereby.

EXAMPLES

A. Preparation Examples

With appropriate modification of the starting materials, the procedure given in the synthesis example below was used to obtain further compounds II. The compounds obtained in this manner are listed in the table that follows, together with physical data.

The products shown below were characterized by melting point determination, by NMR spectroscopy or by the masses ([m/z]) or retention time (RT; [min.]) determined by GC MS spectrometry. [GC MS=gas chromatography-coupled mass spectrometry]

Instrument Settings and Chromatographic Conditions:
Machine: Agilent 6890N/5975 B/MSD
Carrier gas: Helium
Column: Varian 150 m VF-1/ID=0.25 mm, FD=0.25 μm
Injectionsystem: Agilent-Split/Splitless Injector/Modus Split 1:50
Injection: Agilent-Injector 7683 B Series/amount=1 μl Detection: Agilent-MSD
Temperature/Pressure:
Injector: 270° C.
MSD Interface: 280° C.
Source: 230° C.
MS Quad: 150° C.
Starttemp.: 50° C.
Ret. Time 1: 2 min
Rate 1: 10° C./min
Endtemp.: 280° C.
Ret. Time 2: 45 min
Overall operating time: 70 min
Pressure (prgm): const. flow, AV: 31 cm/sec
Septumpurge: 2 ml/min
Sample Preparation:
Compounds were measured as 10% dilution.

Procedure for the Preparation of 2-[(5-bromo-2-pyridyl)methyl]-2-(4-fluorophenyl)propanedinitrile (II-10)

2-(4-fluorophenyl)propanedinitrile (241 mg, 1.50 mmol, 1.0 equiv.) was dissolved in acetone (20 mL). $K_2CO_3$ (312 mg, 2.25 mmol, 1.5 equiv.) was added and the reaction mixture was stirred at room temperature for 60 min. A solution of (5-bromo-2-pyridyl)methyl methanesulfonate (400 mg, 1.50 mmol, 1.0 equiv.) in acetone (20 mL) was added dropwise and the resulting mixture was stirred at room temperature overnight. The solvent was removed under reduced pressure and the residue was purified via column chromatography ($SiO_2$, cyclohexane/ethyl acetate gradient 8/1→1/1) to yield 350 mg (1.06 mmol, 71%) of II-10.

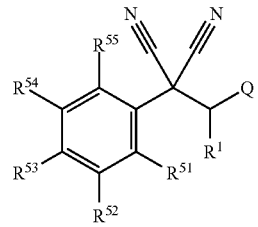

(II)

| Comp. | $R^{51}$ | $R^{52}$ | $R^{53}$ | $R^{54}$ | $R^{55}$ | $R^1$ | Q | RT [min] | m/z [MH]+ |
|---|---|---|---|---|---|---|---|---|---|
| II-1 | H | H | ethynyl | H | H | H | 6-(trifluoromethyl)pyridin-3-yl | 23.767 | 325.1 |
| II-2 | H | H | Cl | H | H | H | 6-(trifluoromethyl)pyridin-3-yl | 23.415 | 335.0 |
| II-3 | H | H | H | H | H | H | 6-(trifluoromethyl)pyridin-3-yl | 21.764 | 301.1 |
| II-4 | H | H | H | H | H | H | 5-(trifluoromethyl)pyridin-2-yl | 21.199 | 301.1 |
| II-5 | H | H | H | H | H | $CH_3$ | 6-(trifluoromethyl)pyridin-3-yl | 21.528 | 311.9 |
| II-6 | H | H | F | H | H | $CH_3$ | 6-(trifluoromethyl)pyridin-3-yl | 21.345 | 331.0 |
| II-7 | H | H | F | H | H | $CH_3$ | 5-bromopyridin-2-yl | 24.640 | 341.0 |
| II-8 | H | H | H | H | H | $CH_3$ | 5-fluoropyridin-2-yl | 23.651 | 265.1 |
| II-9 | H | H | F | H | H | $CH_3$ | 5-fluoropyridin-2-yl | 21.061 | 283.1 |
| II-10 | H | H | F | H | H | H | 5-bromopyridin-2-yl | 24.357 | 329.0 |
| II-11 | H | H | H | H | H | H | 5-fluoropyridin-2-yl | 21.875 | 251.1 |
| II-12 | H | H | F | H | H | H | 5-fluoropyridin-2-yl | 21.563 | 269.1 |
| II-13 | H | H | H | H | H | H | 6-(trifluoromethyl)pyridazin-3-yl | 23.600 | 302.1 |
| II-14 | H | H | F | H | H | H | 6-(trifluoromethyl)pyridazin-3-yl | 23.438 | 320.1 |
| II-15 | H | F | H | H | H | H | 6-(trifluoromethyl)pyridazin-3-yl | 23.529 | 320.1 |
| II-16 | H | H | H | H | H | H | 5-(trifluoromethyl)pyrimidin-2-yl | 21.688 | 302.1 |
| II-17 | H | H | F | H | H | H | 5-(trifluoromethyl)pyrimidin-2-yl | 21.627 | 320.1 |
| II-18 | H | F | H | H | H | H | 5-(trifluoromethyl)pyrimidin-2-yl | 21.436 | 320.1 |
| II-19 | H | F | H | H | H | H | 6-(trifluoromethyl)pyridin-3-yl | 21.924 | 319.1 |
| II-20 | H | H | H | H | H | H | 2-(trifluoromethyl)pyrimidin-5-yl | 22.743 | 302.1 |
| II-21 | H | F | H | H | H | H | 2-(trifluoromethyl)pyrimidin-5-yl | 22.425 | 320.1 |
| II-22 | H | $CH_3$ | H | H | H | H | 6-(trifluoromethyl)pyridin-3-yl | 22.503 | 315.1 |
| II-23 | H | H | F | H | H | H | 2-(trifluoromethyl)pyrimidin-5-yl | 22.897 | 320.1 |
| II-24 | F | H | H | H | H | H | 6-(trifluoromethyl)pyridin-3-yl | 22.186 | 319.1 |
| II-25 | H | H | ethynyl | H | H | H | 6-(trifluoromethyl)pyridin-3-yl | 25.599 | 326.1 |
| II-26 | H | H | H | H | H | H | 5-(trifluoromethyl)pyrazin-2-yl | 22.228 | 302.1 |
| II-27 | H | H | F | H | H | H | 5-(trifluoromethyl)pyrazin-2-yl | 22.247 | 320.1 |
| II-28 | H | F | H | H | H | H | 5-(trifluoromethyl)pyrazin-2-yl | 22.290 | 320.1 |
| II-29 | H | H | H | H | H | H | pyridin-2-yl | 22.540 | 233.1 |
| II-30 | H | H | F | H | H | H | pyridin-2-yl | 22.061 | 251.1 |
| II-31 | H | H | H | H | H | H | pyridin-3-yl | 22.790 | 233.1 |
| II-32 | H | H | F | H | H | H | pyridin-3-yl | 22.758 | 251.1 |
| II-33 | H | H | ethynyl | H | H | H | 5-(trifluoromethyl)pyridin-2-yl | 25.073 | 326.1 |
| II-34 | H | F | H | F | H | H | 6-(trifluoromethyl)pyridin-3-yl | 21.533 | 337.1 |
| II-35 | H | $OCH_3$ | H | H | H | H | 6-(trifluoromethyl)pyridin-3-yl | 23.871 | 331.1 |
| II-36 | F | H | H | H | H | H | 5-(trifluoromethyl)pyridin-2-yl | 21.623 | 319.1 |
| II-37 | H | $CH_3$ | H | H | H | H | 5-(trifluoromethyl)pyridin-2-yl | 25.333 | 315.2 |
| II-38 | H | F | H | F | H | H | 5-(trifluoromethyl)pyridin-2-yl | 20.877 | 337.1 |
| II-39 | H | $OCH_3$ | H | H | H | H | 5-(trifluoromethyl)pyridin-2-yl | 23.510 | 331.1 |
| II-40 | H | CN | H | H | H | H | 6-(trifluoromethyl)pyridin-3-yl | 25.692 | 326.1 |
| II-41 | H | H | F | H | H | $CH_3$ | 5-(trifluoromethyl)pyridin-2-yl | 20.748 | 336.1 |
| II-42 | H | F | H | F | H | $CH_3$ | 5-(trifluoromethyl)pyridin-2-yl | 19.951 | 355.1 |
| II-43 | H | F | F | F | H | H | 6-(trifluoromethyl)pyridin-3-yl | 19.100 | 355.1 |

-continued

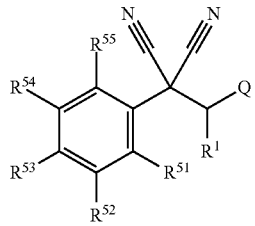

(II)

| Comp. | $R^{51}$ | $R^{52}$ | $R^{53}$ | $R^{54}$ | $R^{55}$ | $R^1$ | Q | RT [min] | m/z [MH]+ |
|---|---|---|---|---|---|---|---|---|---|
| II-44 | F | F | H | H | H | H | 6-(trifluoromethyl)pyridin-3-yl | 19.557 | 337.3 |
| II-45 | H | $CH_3$ | H | $CH_3$ | H | H | 6-(trifluoromethyl)pyridin-3-yl | 21.500 | 329.1 |
| II-46 | H | F | H | $CF_3$ | H | H | 6-(trifluoromethyl)pyridin-3-yl | 18.492 | 387.1 |
| II-47 | H | $CH_3$ | H | $CH_3$ | H | H | 5-(trifluoromethyl)pyridin-2-yl | 21.086 | 329.1 |
| II-48 | H | F | F | F | H | H | 5-(trifluoromethyl)pyridin-2-yl | 18.331 | 355.1 |
| II-49 | F | F | H | H | H | H | 5-(trifluoromethyl)pyridin-2-yl | 19.322 | 337.1 |
| II-50 | H | H | H | H | H | H | 2,6-difluoropyridin-3-yl | 20.031 | 269.1 |
| II-51 | H | H | F | H | H | H | 2,6-difluoropyridin-3-yl | 19.658 | 287.1 |
| II-52 | H | F | H | F | H | H | 2,6-difluoropyridin-3-yl | 18.661 | 305.1 |
| II-54 | H | $CF_3$ | H | $CF_3$ | H | H | 6-(trifluoromethyl)pyridin-3-yl | 17.609 | 437.1 |
| II-55 | H | H | $OCH_2O$ | | H | H | 5-(trifluoromethyl)pyridin-2-yl | 22.983 | 345.1 |
| II-56 | H | H | $OCH_2O$ | | H | H | 6-(trifluoromethyl)pyridin-3-yl | 23.516 | 345.1 |
| II-57 | H | H | $OCH_2O$ | | H | H | 2,6-difluoropyridin-3-yl | 23.296 | 313.1 |
| II-58 | H | H | $OCH_2CH_2O$ | | H | H | 6-(trifluoromethyl)pyridin-3-yl | 24.858 | 359.1 |
| II-59 | H | H | $OCH_2CH_2O$ | | H | H | 5-(trifluoromethyl)pyridin-2-yl | 24.517 | 359.1 |
| II-60 | H | $CF_3$ | H | $CF_3$ | H | H | 5-(trifluoromethyl)pyridin-2-yl | 16.836 | 437.1 |
| II-61 | H | F | F | F | H | $CH_3$ | 5-(trifluoromethyl)pyridin-2-yl | 18.443 | 370.1 |
| II-62 | H | H | N=CH—CH=CH | | H | H | 6-(trifluoromethyl)pyridin-3-yl | 25.277 | 352.1 |
| II-63 | H | H | N=CH—CH=CH | | H | H | 2,6-difluoropyridin-3-yl | 25.213 | 320.1 |
| II-64 | H | H | N=CH—CH=CH | | H | H | 5-(trifluoromethyl)pyridin-2-yl | 24.793 | 352.1 |
| II-65 | H | F | F | F | H | H | 6-methylpyridin-2-yl | 20.341 | 301.3 |
| II-66 | H | F | F | F | H | H | 3,5-dichloropyridin-4-yl | 26.339 | 356.1 |
| II-67 | F | F | I | F | F | H | 6-(trifluoromethyl)pyridin-3-yl | 23.333 | 498.9 |

NMR-data for II-43: $^1$H-NMR (500 MHz, $CDCl_3$): δ=3.55 (s, 2H), 7.22 (t, 1H), 7.76 (d, 1H), 7.85 (d, 1H), 8.50 (s, 1H).

B. Biological Examples

The activity of the compounds of formula II of the present invention could be demonstrated and evaluated in biological tests described in the following.

If not otherwise specified the test solutions are prepared as follows:

The active compound is dissolved at the desired concentration in a mixture of 1:1 (vol:vol) distilled water:acetone. The test solution is prepared at the day of use and in general at concentrations of ppm (wt/vol).

B.1 Cowpea Aphid (*Aphis craccivora*)

The active compounds were formulated in 50:50 (v/v) acetone:water. The test solution was prepared at the day of use. Potted cowpea plants colonized with approximately 100-150 aphids of various stages were sprayed after the pest population has been recorded. Population reduction was assessed after 24, 72, and 120 hours.

In this test, the compounds II-2, II-3, II-4, II-5, II-6, II-8, II-14, II-15, II-16, II-17, II-19, II-20, II-21, II-23, II-26, II-28, II-38, II-41, II-42, II-43, II-47 and II-61, respectively, at 500 ppm showed a mortality of at least 75% in comparison with untreated controls.

B.2 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs. The compounds were formulated using a solution containing 75% v/v water and 25% v/v DMSO. Different concentrations of formulated compounds were sprayed onto the insect diet at 5 µl, using a custom built micro atomizer, at two replications. After application, microtiter plates were incubated at about 28±1° C. and about 80±5% relative humidity for 5 days. Egg and larval mortality was then visually assessed.

In this test, the compounds II-5, II-6, II-7, II-19, II-20, II-23, II-26, II-27, II-34, II-41, II-42, II-43, II-48 and II-61, respectively, at 2500 ppm showed a mortality of at least 75% in comparison with untreated controls.

B.3 Green Peach Aphid (*Myzus persicae*)

For evaluating control of green peach aphid (*Myzus persicae*) through systemic means the test unit consisted of 96-well-microtiter plates containing liquid artificial diet under an artificial membrane. The compounds were formulated using a solution containing 75% v/v water and 25% v/v DMSO. Different concentrations of formulated compounds were pipetted into the aphid diet, using a custom built pipetter, at two replications. After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, the compounds II-4, II-5, II-6, II-8, II-9, II-11, II-13, II-14, II-15, II-16, II-18, II-20, II-23, II-34, II-38, II-39, II-41, II-42, II-43, II-48, II-52, II-57 and II-61, respectively, at a concentration of the test solution of 2500 mg/L showed a mortality of at least 75%.

B.4 Orchid Thrips (*Dichromothrips Corbetti*)

*Dichromothrips corbetti* adults used for bioassay are obtained from a colony maintained continuously under laboratory conditions. For testing purposes, the test compound is diluted to a concentration of 300 ppm (wt compound: vol diluent) in a 1:1 mixture of acetone:water (vol:vol), plus 0.01% vol/vol Kinetic® surfactant. *Thrips* potency of each compound is evaluated by using a floral-immersion technique. Plastic petri dishes are used as test arenas. All petals of individual, intact orchid flowers are dipped into treatment solution and allowed to dry. Treated flowers are placed into individual petri dishes along with 10-15 adult *thrips*. The petri dishes are then covered with lids. All test arenas are held under continuous light and a temperature of about 28° C. for duration of the assay. After 4 days, the numbers of live *thrips* are counted on each flower, and along inner walls of each petri dish. The level of *thrips* mortality is extrapolated from pre-treatment *thrips* numbers.

In this test, the compounds II-2, II-3, II-4, II-5, II-6, II-10, II-15, II-16, II-17, II-18, II-19, II-20, II-21, II-23, II-24, II-26, II-27, II-28, II-33, II-34, II-38, II-41, II-42, II-43, II-46, II-48, II-49, II-50, II-51, II-52, II-61 and II-65, respectively, at 500 ppm showed a mortality of at least 75% in comparison with untreated controls.

B.5 Silverleaf Whitefly (*Bemisia argentifolii*)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v). Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days old) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds II-1, II-2, II-4, II-8, II-9, II-12, II-13, II-15, II-16, II-17, II-18, II-19, II-20, II-21, II-23, II-24, II-26, II-27, II-28, II-31, II-34, II-36, II-38, II-41 and II-42, respectively, at 500 ppm showed a mortality of at least 75% in comparison with untreated controls.

B.6 Southern Armyworm (*Spodoptera eridania*)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v). Lima bean plants (variety Sieva) were grown 2 plants to a pot and selected for treatment at the 1st true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. Ten to 11 armyworm larvae were placed into the bag and the bags zipped closed. Test plants were maintained in a growth room at 25° C. and 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds II-7, II-8, II-14, II-16, II-17 and II-34, respectively, at 500 ppm showed a mortality of at least 75% in comparison with untreated controls.

Additionally, the compounds II-5, II-6, II-8, II-19 and II-38, respectively, at 300 ppm showed a mortality of at least 75% in comparison with untreated controls.

B.7 Vetch Aphid (*Megoura viciae*)

For evaluating control of vetch aphid (*Megoura viciae*) through contact or systemic means the test unit consisted of 24-well-microtiter plates containing broad bean leaf disks. The compounds were formulated using a solution containing 75% v/v water and 25% v/v DMSO. Different concentrations of formulated compounds were sprayed onto the leaf disks at 2.5 µl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds II-3, II-4, II-5, II-6, II-16, II-17, II-18, II-19, II-20, II-21, II-23, II-26, II-27, II-28, II-34, II-38, II-41, II-42, II-43, II-48, II-61 and II-66, respectively, at 2500 ppm showed a mortality of at least 75% in comparison with untreated controls.

B.8 Tobacco Budworm (*Heliothis virescens*) I

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v). Cotton plants were grown 2 plants to a pot and selected for treatment at the cotyledon stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 budworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds II-3, II-5, II-6, II-11, II-26, II-31, II-50 and II-52, respectively, at 2500 ppm showed a mortality of at least 75% in comparison with untreated controls.

B.9 Boll Weevil (*Anthonomus grandis*)

For evaluating control of boll weevil (*Anthonomus grandis*) the test unit consisted of 24-well-microtiter plates containing an insect diet and 20-30 *A. grandis* eggs. The compounds were formulated using a solution containing 75% v/v water and 25% v/v DMSO. Different concentrations of formulated compounds were sprayed onto the insect diet at 20 μl, using a custom built micro atomizer, at two replications. After application, microtiter plates were incubated at about 23±1° C. and about 50±5% relative humidity for 5 days. Egg and larval mortality was then visually assessed.

In this test, the compounds II-1, II-2, II-3, II-4, II-5, II-6, II-7, II-8, II-9, II-10, II-13, II-14, II-15, II-16, II-17, II-18, II-19, II-20, II-21, II-23, II-24, II-25, II-26, II-27, II-28, II-31, II-34, II-36, II-38, II-41, II-42, II-43, II-48, II-52, II-61, II-62 and II-65, respectively, at 2500 ppm showed a mortality of at least 75% in comparison with untreated controls.

B.10 Red Spider Mite (*Tetranychus kanzawai*)

The active compound is dissolved at the desired concentration in a mixture of 1:1 (vol:vol) distilled water:acetone. Add surfactant (Alkamuls® EL 620) at the rate of 0.1% (vol/vol). The test solution is prepared at the day of use. Potted cowpea beans of 7-10 days of age were cleaned with tap water and sprayed with 5 ml of the test solution using air driven hand atomizer. The treated plants were allowed to air dry and afterwards inculated with 20 or more mites by clipping a cassava leaf section with known mite population. Treated plants were placed inside a holding room at about 25-27° C. and about 50-60% relative humidity. Percent mortality was assessed 72 hours after treatment.

In this test, the compounds II-7, II-9, II-16, II-20, II-26, II-28, II-33, II-41, II-42, II-43 and II-51, respectively, at 500 ppm showed a mortality of at least 75% in comparison with untreated controls.

B.11 Rice brown plant hopper (*Nilaparvata lugens*)

Rice seedlings were cleaned and washed 24 hours before spraying. The active compounds were formulated in 50:50 acetone:water (vol:vol) and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds II-1, II-3, II-4, II-5, II-6, II-8, II-9, II-10, II-16, II-20, II-21, II-22, II-23, II-24, II-27, II-34, II-36, II-38, II-41, II-42, II-43, II-48, II-49, II-61 and II-65, respectively, at 300 ppm showed a mortality of at least 75% in comparison with untreated controls.

B.12 Yellow Fever Mosquito (*Aedes aegypti*)

For evaluating control of yellow fever mosquito (*Aedes aegypti*) the test unit consisted of 96-well-microtiter plates containing 200 μl of tap water per well and 5-15 freshly hatched *A. aegypti* larvae. The compounds or mixtures were formulated using a solution containing 75% water and 25% DMSO. Different concentrations of formulated compounds or mixtures were sprayed onto the insect diet at 2.5 μl, using a custom built micro atomizer, at two replications. After application, microtiter plates were incubated at 28±1° C., 80±5% relative humidity for 2 days. Larval mortality was then visually assessed.

In this test, the compounds II-2, II-3, II-4, II-8, II-9, II-13, II-15, II-16, II-17, II-18, II-19, II-20, II-21, II-23, II-24, II-26, II-27, II-28, II-29, II-34, II-36, II-37, II-38, II-41, II-42, II-43, II-46, II-47, II-48, II-50, II-51, II-53, II-54, II-60, II-61, II-65 and II-66, respectively, at 2500 ppm showed a mortality of at least 75% in comparison with untreated controls.

B.13 Green Peach Aphid (*Myzus persicae*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v). Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at about 25° C. and about 20-40% relative humidity. Aphid mortality on the treated plants, relative to mortality on untreated control plants, was determined after 5 days.

In this test, the compound II-5, II-6, II-7, II-8 and II-34, respectively at 300 ppm showed a mortality of at least 75% in comparison with untreated controls.

B.14 Cotton Aphid (*Aphis gossypii*, Mixed Life Stages)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v). Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds II-5, II-6 and II-8, respectively at 300 ppm showed at least 75% mortality in comparison with untreated controls.

B.15 Green Soldier Stink Bug (*Nezara viridula*)

The active compound is dissolved at the desired concentration in a mixture of 1:1 (vol:vol) distilled water:aceteone. Surfactant (Kinetic HV) is added at a rate of 0.01% (vol/vol). The test solution is prepared at the day of use. Soybean pods were placed in microwavable plastic cups lined with moist filter paper and inoculated with ten 3rd instar *N. viridula*. Using a hand atomizer, an approximately 2 ml solution is sprayed into each cup. Treated cups were kept at about 28-29° C. and relative humidity of about 50-60%. Percent mortality was recorded after 5 days.

In this test, the compounds II-3, II-4, II-19, II-20, II-21, II-41, II-48, II-49, II-61 and II-65, respectively, at 500 ppm showed a mortality of at least 75% in comparison with untreated controls.

The invention claimed is:

1. A method for combating animal pests comprising contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of formula (I)

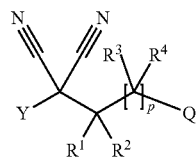

(I)

or a salt or N-oxide thereof, wherein

Y is phenyl unsubstituted or substituted with 1, 2, 3, 4 or 5 substituents $R^5$; or
naphthyl unsubstituted or substituted with 1, 2, 3, 4, 5, 6 or 7 substituents $R^5$;
Q is a 6-membered aromatic heterocyclic ring containing 1, 2, 3 or 4 nitrogen atoms in the ring, wherein the aforementioned ring is unsubstituted or substituted with 1, 2, 3 or 4 substituents $R^6$;
$R^1$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;
$R^2$ is hydrogen or halogen;
or
$R^1$ and $R^2$ form together with the carbon atom to which they are attached a methylene group or a cyclopropyl group;
$R^3$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;
$R^4$ is hydrogen or halogen;
or
$R^3$ and $R^4$ form together with the carbon atom to which they are attached a methylene group or a cyclopropyl group;
each $R^5$, $R^6$ is independently selected from the group consisting of halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;
$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;
phenyl unsubstituted or substituted with up to 5 $R^c$;
a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^d$;

$Si(R^e)_3$, $OR^f$, $SR^f$, $OS(O)_x h$, $S(O)_x R^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;
or
two $R^5$ on two adjacent carbon atoms present on one phenyl ring are together a bridge selected from the group consisting of $CH_2CH_2CH_2CH_2$, N=CH—CH=CH, CH=N—CH=CH, N=CH—N=CH, N=CH—CH=N, $OCH_2CH_2CH_2$, OCH=CHCH$_2$, $CH_2OCH_2CH_2$, $OCH_2CH_2O$, $OCH_2OCH_2$, $CH_2CH_2CH_2$, CH=CHCH$_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=CHCH$_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from =O, OH, $CH_3$, $OCH_3$, halogen, halomethyl and halomethoxy;
each $R^7$ is independently selected from the group consisting of halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;
each $R^a$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl,
$Si(R^e)_3$, $OR^A$, $SR^A$, $OSO_2R^B$, $S(O)_x R^B$, —$S(O)_x N(R^D)_2$, $N(R^D)_2$, $C(=O)N(R^D)_2$, $C(=S)N(R^D)_2$, $C(=O)OR^A$,
phenyl unsubstituted or substituted with up to 5 $R^E$;
a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^E$,
or
two $R^a$ present on one carbon atom are together =O, =C(R$^F$)$_2$, =NR$^D$, =NOR$^A$, =NNR$^D$,
or
two $R^a$ form a 3-, 4-, 5-, 6-, 7- or 8-membered saturated or partially unsaturated carbocyclic or heterocyclic ring together with the carbon atoms the two $R^a$ are bonded to;
each $R^b$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl,
$Si(R^G)_3$, $OR^H$, $SR^H$, $OSO_2R^J$, $S(O)_x R^J$, —$S(O)_x N(R^K)_2$, $N(R^K)_2$, $C(=O)N(R^K)_2$, $C(=S)N(R^K)_2$, $C(=O)OR^H$, or two $R^b$ present on one carbon atom are together =O, =C($R^L$)$_2$, =N$R^K$, =NO$R^H$, =NN$R^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently selected from the group consisting of halogen, cyano, azido, nitro, —SCN, SF$_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

Si($R^G$)$_3$, O$R^H$, S$R^H$, OS(O)$_x$$R^J$, S(O)$_x$$R^J$, —S(O)$_x$N($R^K$)$_2$, N($R^K$)$_2$, C(=O)$R^N$, C(=O)O$R^H$, C(=N$R^K$)$R^N$, C(=O)N($R^K$)$_2$, C(=S)N($R^K$)$_2$;

each $R^d$ is independently selected from the group consisting of halogen, cyano, azido, nitro, —SCN, SF$_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

Si($R^G$)$_3$, O$R^H$, S$R^H$, OS(O)$_x$$R^J$, S(O)$_x$$R^J$, —S(O)$_x$N($R^K$)$_2$, N($R^K$)$_2$, C(=O)$R^N$, C(=O)O$R^H$, C(=N$R^K$)$R^N$, C(=O)N($R^K$)$_2$, C(=S)N($R^K$)$_2$, or two $R^d$ present on one atom of a saturated or partially unsaturated heterocyclic ring are together =O, =C($R^L$)$_2$; =N$R^K$, =NO$R^H$ or =NN$R^K$;

each $R^e$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$;

each $R^f$ is independently selected from the group consisting of hydrogen, cyano, $C_1$-$C_6$-alkyl, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

Si($R^e$)$_3$, S(O)$_x$$R^B$, —S(O)$_x$N($R^D$)$_2$, N($R^D$)$_2$, —N=C($R^F$)$_2$, C(=O)$R^Q$, C(=O)N($R^D$)$_2$, C(=S)N($R^D$)$_2$, C(=O)O$R^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$;

each $R^h$ is independently selected from the group consisting of hydrogen, cyano, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

N($R^D$)$_2$, —N=C($R^F$)$_2$, C(=O)$R^Q$, C(=O)N($R^D$)$_2$, C(=S)N($R^D$)$_2$, C(=O)O$R^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$;

each $R^i$ is independently selected from the group consisting of hydrogen, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

S(O)$_x$$R^B$, —S(O)$_x$N($R^D$)$_2$, C(=O)$R^S$, C(=O)O$R^A$, C(=O)N($R^D$)$_2$, C(=S)$R^S$, C(=S)S$R^A$, C(=S)N($R^D$)$_2$, C(=N$R^D$)$R^S$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, SO$_2$, wherein the aforementioned ring is unsubstituted or substituted with up to 5 $R^E$, or two $R^i$ on one nitrogen atom are together a $C_2$-$C_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from the group consisting of N, O, S, NO, SO, SO$_2$, and wherein the alkylene chain is unsubstituted or substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl, $C_2$-$C_6$-haloalkynyl;

each $R^m$ is independently selected from the group consisting of hydrogen, —SCN, SF$_5$, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

Si($R^e$)$_3$, O$R^A$, S$R^A$, OSO$_2$$R^B$, N($R^D$)$_2$, C(=O)N($R^D$)$_2$, C(=S)N($R^D$)$_2$, C(=O)O$R^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$, wherein the aforementioned ring is unsubstituted or substituted with up to 5 $R^E$;

each $R^A$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^B$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^D$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$-alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or two $R^D$ on one nitrogen atom are together a $C_2$-$C_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from the group consisting of N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently selected from the group consisting of cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

each $R^F$ is independently selected from the group consisting of $C_1$-$C_4$ alkyl, $C_1$-$C_6$ cycloalkyl, $C_1$-$C_4$ alkoxyalkyl, phenyl and benzyl;

each $R^G$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^J$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently $C_1$-$C_4$ alkyl or $C_1$-$C_4$ alkoxyalkyl;

each $R^M$ is independently selected from the group consisting of halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

each $R^N$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently selected from the group consisting of hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1;

x is 1 or 2, with the proviso that the following compound is excluded:

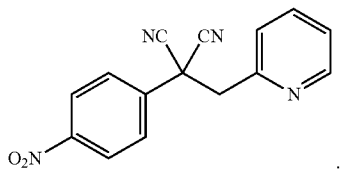

2. The method of claim 1, wherein
each $R^5$, $R^6$ is independently selected from the group consisting of halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;
$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;
phenyl unsubstituted or substituted with up to 5 $R^c$;
a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^d$;
$Si(R^e)_3$, $OR^f$, $SR^f$, $OS(O)_xR^h$, $S(O)_xR^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;
or
two $R^5$ on two adjacent carbon atoms present on one phenyl ring are together a bridge selected from the group consisting of $CH_2CH_2CH_2CH_2$, N=CH—CH=CH, CH=N—CH=CH, N=CH—N=CH, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from the group consisting of =O, OH, $CH_3$, $OCH_3$, halogen, halomethyl and halomethoxy.

3. The method of claim 1, wherein
Y is phenyl unsubstituted or substituted with 1, 2, 3, 4 or 5 substituents $R^5$; or
naphthyl unsubstituted or substituted with 1 or 2 substituents $R^5$;
Q is a 6-membered aromatic heterocyclic ring containing 1, 2 or 3 nitrogen atoms in the ring, wherein the aforementioned ring is unsubstituted or substituted with 1, 2, 3 or 4 substituents $R^6$;
$R^1$ is selected from the group consisting of H, halogen, cyano, $C_1$-$C_6$-alkyl, $C_2$-$C_6$-alkenyl, $C_2$-$C_6$-alkynyl, $C_3$-$C_6$-cycloalkyl and ($C_1$-$C_6$-alkoxy)carbonyl,
wherein the five radicals last mentioned are unsubstituted or substituted with 1, 2 or 3 substituents selected from the group consisting of halogen, cyano, hydroxy, OSi($C_1$-$C_6$-alkyl)$_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl,
wherein the six radicals last mentioned are unsubstituted or partially or fully halogenated;
$R^2$ is H or halogen;
or
$R^1$ and $R^2$ form together with the carbon atom to which they are attached a methylene group;
$R^3$ is selected from the group consisting of H, halogen, cyano, $C_1$-$C_6$-alkyl, $C_2$-$C_6$-alkenyl, $C_2$-$C_6$-alkynyl, $C_3$-$C_6$-cycloalkyl and ($C_1$-$C_6$-alkoxy)carbonyl,
wherein the five radicals last mentioned are unsubstituted or substituted with 1, 2 or 3 substituents selected from the group consisting of halogen, cyano, hydroxy, OSi($C_1$-$C_6$-alkyl)$_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl,
wherein the six radicals last mentioned are unsubstituted or partially or fully halogenated;
$R^4$ is H or halogen;
or $R^3$ and $R^4$ form together with the carbon atom to which they are attached a methylene group;
$R^5$ is selected from the group consisting of halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl and ($C_1$-$C_6$-alkyl)carbonyloxy,
wherein the 14 radicals last mentioned are unsubstituted or substituted with one or more substituents selected from the group consisting of halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy,
wherein the five radicals last mentioned are unsubstituted or partially or fully halogenated;
or
two $R^5$ on two adjacent carbon atoms present on one phenyl ring are together a bridge selected from the group consisting of N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted;
$R^6$ is selected from the group consisting of halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl and ($C_1$-$C_6$-alkyl)carbonyloxy,
wherein the 14 radicals last mentioned are unsubstituted or substituted with one or more substituents selected from the group consisting of halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy,
wherein the five radicals last mentioned are unsubstituted or partially or fully halogenated;
p is 0 or 1.

4. The method of claim 1, wherein

Y is phenyl unsubstituted or substituted with 1, 2, 3 or 4 substituents $R^5$; or naphthyl unsubstituted or substituted with 1 or 2 substituents $R^5$;

Q is a 6-membered aromatic heterocyclic ring containing 1, 2 or 3 nitrogen atoms in the ring, wherein the aforementioned ring is unsubstituted or substituted with 1, 2, 3 or 4 substituents $R^6$;

$R^1$ is selected from the group consisting of H, halogen, cyano, $C_1$-$C_6$-alkyl, $C_2$-$C_6$-alkenyl, $C_2$-$C_6$-alkynyl, $C_3$-$C_6$-cycloalkyl and ($C_1$-$C_6$-alkoxy)carbonyl, wherein the five radicals last mentioned are unsubstituted or substituted with 1, 2 or 3 substituents selected from the group consisting of halogen, cyano, hydroxy, OSi($C_1$-$C_6$-alkyl)$_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated;

$R^2$ is H or halogen;

or $R^1$ and $R^2$ form together with the carbon atom to which they are attached a methylene group;

$R^3$ is selected from the group consisting of H, halogen, cyano, $C_1$-$C_6$-alkyl, $C_2$-$C_6$-alkenyl, $C_2$-$C_6$-alkynyl, $C_3$-$C_6$-cycloalkyl and ($C_1$-$C_6$-alkoxy)carbonyl, wherein the five radicals last mentioned are unsubstituted or substituted with 1, 2 or 3 substituents selected from the group consisting of halogen, cyano, hydroxy, OSi($C_1$-$C_6$-alkyl)$_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated;

$R^4$ is H or halogen;

or $R^3$ and $R^4$ form together with the carbon atom to which they are attached a methylene group;

$R^5$ is selected from the group consisting of halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl and ($C_1$-$C_6$-alkyl)carbonyloxy, wherein the 14 radicals last mentioned are unsubstituted or substituted with one or more substituents selected from the group consisting of halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

$R^6$ is selected from the group consisting of halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl and ($C_1$-$C_6$-alkyl)carbonyloxy, wherein the 14 radicals last mentioned are unsubstituted or substituted with one or more substituents selected from the group consisting of halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

p is 0 or 1.

5. The method of claim 1, wherein $R^1$ is selected from the group consisting of H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ and $CH_2OSi(Et)_3$.

6. The method of claim 1, wherein $R^3$ is selected from the group consisting of H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ and $CH_2OSi(Et)_3$.

7. The method of claim 1, wherein $R^5$ is selected from the group consisting of halogen, Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, C(O)Me, OAc, C(O)NHMe, $C(O)NMe_2$, $CH_2OMe$ and $CH_2OEt$;

or two $R^5$ on two adjacent carbon atoms present on one phenyl ring are together a bridge selected from the group consisting of N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted.

8. The method of claim 1, wherein $R^5$ is selected from the group consisting of halogen, Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, C(O)Me, OAc, C(O)NHMe, $C(O)NMe_2$, $CH_2OMe$ and $CH_2OEt$.

9. The method of claim 1, wherein $R^6$ is selected from the group consisting of halogen, Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, C(O)Me, OAc, C(O)NHMe, $C(O)NMe_2$, $CH_2OMe$ and $CH_2OEt$.

10. The method of claim 1, wherein

Y is phenyl unsubstituted or substituted with 1, 2, 3, 4 or 5 substituents $R^5$; or naphthyl unsubstituted or substituted with 1 substituent $R^5$;

Q is a 6-membered aromatic heterocyclic ring containing 1, 2 or 3 nitrogen atoms in the ring, wherein the aforementioned ring is unsubstituted or substituted with 1, 2 or 3 substituents $R^6$;

$R^1$ is selected from the group consisting of H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ and $CH_2OSi(Et)_3$;

$R^2$ is H or halogen;

$R^3$ is selected from the group consisting of H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ and $CH_2OSi(Et)_3$;

R⁴ is H or halogen;
R⁵ is selected from the group consisting of halogen, cyano, tri-($C_1$-$C_4$)silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy) carbonyl,
wherein the eight radicals last mentioned are unsubstituted or partially or fully halogenated;
or
two R⁵ on two adjacent carbon atoms present on one phenyl ring are together a bridge selected from the group consisting of N=CH—CH=CH, N=CH—CH=N, OCH₂CH₂O, O(CH₂)O and form together with the carbon atoms the two R⁵ are bonded to a 5- or 6-membered partially unsaturated or aromatic heterocyclic ring, wherein the ring is unsubstituted;
R⁶ is selected from the group consisting of halogen, cyano, tri-($C_1$-$C_4$)silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio and ($C_1$-$C_6$-alkoxy) carbonyl,
wherein the eight radicals last mentioned are unsubstituted or partially or fully halogenated;
p is 0 or 1.

11. The method of claim 1, wherein
Y is phenyl unsubstituted or substituted with 1, 2 or 3 substituents R⁵; or naphthyl unsubstituted or substituted with 1 substituent R⁵;
Q is a 6-membered aromatic heterocyclic ring containing 1, 2 or 3 nitrogen atoms in the ring, wherein the aforementioned ring is unsubstituted or substituted with 1, 2 or 3 substituents R⁶;
R¹ is selected from the group consisting of H, Me, Et, CN, CH₂CN, CH₂CF₃, halogen, CH₂OH, CH₂OMe, CH₂OEt, CH₂CO₂Me, CH₂CO₂Et, CH₂OSi(Me)₃ and CH₂OSi(Et)₃;
R² is H or halogen;
R³ is selected from the group consisting of H, Me, Et, CN, CH₂CN, CH₂CF₃, halogen, CH₂OH, CH₂OMe, CH₂OEt, CH₂CO₂Me, CH₂CO₂Et, CH₂OSi(Me)₃ and CH₂OSi(Et)₃;
R⁴ is H or halogen;
R⁵ is selected from the group consisting of halogen, cyano, tri-($C_1$-$C_4$)silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio and ($C_1$-$C_6$-alkoxy) carbonyl,
wherein the eight radicals last mentioned are unsubstituted or partially or fully halogenated;
R⁶ is selected from the group consisting of halogen, cyano, tri-($C_1$-$C_4$)silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio and ($C_1$-$C_6$-alkoxy) carbonyl,
wherein the eight radicals last mentioned are unsubstituted or partially or fully halogenated;
p is 0 or 1.

12. The method of claim 1, wherein
R⁵ is selected from the group consisting of halogen, Me, OMe, CN, CF₃, OCF₃ and ethynyl.

13. The method of claim 1, wherein
R⁶ is selected from the group consisting of halogen, Me, OMe, CN, CF₃, OCF₃ and ethynyl.

14. The method of claim 1, wherein
Y is phenyl unsubstituted or substituted with 1, 2 or 3 substituents R⁵;
Q is pyridyl, pyrimidinyl, pyrazinyl or pyridazinyl, wherein the aforementioned rings are unsubstituted or substituted with 1 or 2 substituents R⁶;
R¹ is selected from the group consisting of H, F, Me, Et, CN, CH₂CN and CH₂OMe;
R² is H;
R³ is selected from the group consisting of H, F, Me, Et, CN, CH₂CN and CH₂OMe;
R⁴ is H;
R⁵ is selected from the group consisting of F, Cl, CN, ethynyl, Me, OMe and CF₃;
R⁶ is F, ethynyl, Br or CF₃;
p is 0 or 1.

15. The method of claim 1, wherein R¹ is H.
16. The method of claim 1, wherein R³ is H.
17. The method of claim 1, wherein p is 0.
18. The method of claim 1, wherein Q is pyridyl or pyrimidinyl, wherein the aforementioned rings are unsubstituted or substituted with one or more R⁶.
19. The method of claim 1, wherein R¹ and R² are H; and p is 0.
20. A method for protecting crops from attack or infestation by animal pests comprising contacting the crop with a pesticidally effective amount of at least one compound of formula (I)

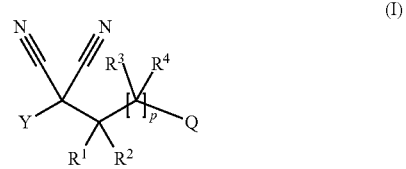

or a salt or N-oxide thereof, wherein
Y is phenyl unsubstituted or substituted with 1, 2, 3, 4 or 5 substituents R⁵; or
naphthyl unsubstituted or substituted with 1, 2, 3, 4, 5, 6 or 7 substituents R⁵;
Q is a 6-membered aromatic heterocyclic ring containing 1, 2, 3 or 4 nitrogen atoms in the ring, wherein the aforementioned ring is unsubstituted or substituted with 1, 2, 3 or 4 substituents R⁶;
R¹ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents R⁷;
R² is hydrogen or halogen;
or
R¹ and R² form together with the carbon atom to which they are attached a methylene group or a cyclopropyl group;
R³ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents R⁷;

$R^4$ is hydrogen or halogen;

or $R^3$ and $R^4$ form together with the carbon atom to which they are attached a methylene group or a cyclopropyl group;

each $R^5$, $R^6$ is independently selected from the group consisting of halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;

$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;

phenyl unsubstituted or substituted with up to 5 $R^c$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^d$;

$Si(R^e)_3$, $OR^f$, $SR^f$, $OS(O)_xR^h$, $S(O)_xR^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;

or two $R^5$ on two adjacent carbon atoms present on one phenyl ring are together a bridge selected from the group consisting of $CH_2CH_2CH_2CH_2$, N=CH—CH=CH, CH=N—CH=CH, N=CH—N=CH, N=CH—CH=N, $OCH_2CH_2CH_2$, OCH=$CHCH_2$, $CH_2OCH_2CH_2$, OCH—$CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from =O, OH, $CH_3$, $OCH_3$, halogen, halomethyl and halomethoxy;

each $R^7$ is independently selected from the group consisting of halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;

each $R^a$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^e)_3$, $OR^A$, $SR^A$, $OSO_2R^B$, $S(O)_xR^B$, —$S(O)_xN(R^D)_2$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^E$, or two $R^a$ present on one carbon atom are together =O, =$C(R^F)_2$, =$NR^D$, =$NOR^A$, =$NNR^D$, or two $R^a$ form a 3-, 4-, 5-, 6-, 7- or 8-membered saturated or partially unsaturated carbocyclic or heterocyclic ring together with the carbon atoms the two $R^a$ are bonded to;

each $R^b$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^G)_3$, $OR^H$, $SR^H$, $OSO_2R^J$, $S(O)_xR^J$, —$S(O)_xN(R^K)_2$, $N(R^K)_2$, $C(=O)N(R^K)_2$, $C(=S)N(R^K)_2$, $C(=O)OR^H$, or two $R^b$ present on one carbon atom are together =O, =$C(R^L)_2$, =$NR^K$, =$NOR^H$, =$NNR^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently selected from the group consisting of halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$;

each $R^d$ is independently selected from the group consisting of halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$, or two $R^d$ present on one atom of a saturated or partially unsaturated heterocyclic ring are together =O, =$C(R^L)_2$; =$NR^K$, =$NOR^H$ or =$NNR^K$;

each $R^e$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^f$ is independently selected from the group consisting of hydrogen, cyano, $C_1$-$C_6$-alkyl, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $S(O)_xR^B$, $-S(O)_xN(R^D)_2$, $N(R^D)_2$, $-N=C(R^F)_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^h$ is independently selected from the group consisting of hydrogen, cyano, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$N(R^D_2)$, $-N=C(R^F)_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^i$ is independently selected from the group consisting of hydrogen, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$S(O)_xR^B$, $-S(O)_xN(R^D)_2$, $C(=O)R^S$, $C(=O)OR^A$, $C(=O)N(R^D)_2$, $C(=S)R^S$, $C(=S)SR^A$, $C(=S)N(R^D)_2$, $C(=NR^D)R^S$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^E$, or two $R^i$ on one nitrogen atom are together a $C_2$-$C_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from the group consisting of N, O, S, NO, SO, $SO_2$, and wherein the alkylene chain is unsubstituted or substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl, $C_2$-$C_6$-haloalkynyl;

each $R^m$ is independently selected from the group consisting of hydrogen, —SCN, $SF_5$, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $OR^A$, $SR^A$, $OSO_2R^B$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$;

each $R^A$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^B$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^D$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$-alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or two $R^D$ on one nitrogen atom are together a $C_2$-$C_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from the group consisting of N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently selected from the group consisting of cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

each $R^F$ is independently selected from the group consisting of $C_1$-$C_4$ alkyl, $C_1$-$C_6$ cycloalkyl, $C_1$-$C_4$ alkoxyalkyl, phenyl and benzyl;

each $R^G$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^J$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently $C_1$-$C_4$ alkyl or $C_1$-$C_4$ alkoxyalkyl;

each $R^M$ is independently selected from the group consisting of halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

each $R^N$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently selected from the group consisting of hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1;

x is 1 or 2, with the proviso that the following compound is excluded:

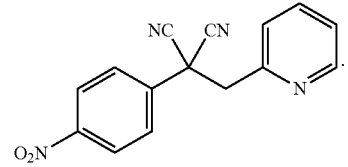 [SMILES: N#CC(C#N)(Cc1ccccn1)c1ccc([N+](=O)[O-])cc1]

21. A method for protecting seeds from soil insects and the seedlings' roots and shoots from soil and foliar insects, which comprises contacting the seeds before sowing and/or after pregermination with at least one compound of formula (I)

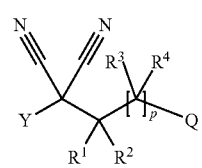

(I)

or a salt or N-oxide thereof, wherein

Y is phenyl unsubstituted or substituted with 1, 2, 3, 4 or 5 substituents $R^5$; or naphthyl unsubstituted or substituted with 1, 2, 3, 4, 5, 6 or 7 substituents $R^5$;

Q is a 6-membered aromatic heterocyclic ring containing 1, 2, 3 or 4 nitrogen atoms in the ring, wherein the aforementioned ring is unsubstituted or substituted with 1, 2, 3 or 4 substituents $R^6$;

$R^1$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-

$C_6$-alkoxy)carbonyl, wherein the carbon atoms of the aforementioned aliphatic or cycloaliphatic radicals are unsubstituted or substituted with 1, 2 or 3 substituents $R^7$:

$R^2$ is hydrogen or halogen;

or $R^1$ and $R^2$ form together with the carbon atom to which they are attached a methylene group or a cyclopropyl group;

$R^3$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$:

$R^4$ is hydrogen or halogen;

or $R^3$ and $R^4$ form together with the carbon atom to which they are attached a methylene group or a cyclopropyl group;

each $R^5$, $R^6$ is independently selected from the group consisting of halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;

$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;

phenyl unsubstituted or substituted with up to 5 $R^c$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^d$;

$Si(R^e)_3$, $OR^f$, $SR^f$, $OS(O)_xR^h$, $S(O)_xR^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;

or two $R^5$ on two adjacent carbon atoms present on one phenyl ring are together a bridge selected from the group consisting of $CH_2CH_2CH_2CH_2$, N=CH—CH=CH, CH=N—CH=CH, N=CH—N=CH, N=CH—CH=N, $OCH_2CH_2CH_2$, $OCH=CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from =O, OH, $CH_3$, $OCH_3$, halogen, halomethyl and halomethoxy;

each $R^7$ is independently selected from the group consisting of halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;

each $R^a$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^e)_3$, $OR^A$, $SR^A$, $OSO_2R^B$, $S(O)_xR^B$, —$S(O)_xN(R^D)_2$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^E$, or two $R^a$ present on one carbon atom are together =O, =C($R^F$)$_2$, =$NR^D$, =$NOR^A$, =$NNR^D$, or two $R^a$ form a 3-, 4-, 5-, 6-, 7- or 8-membered saturated or partially unsaturated carbocyclic or heterocyclic ring together with the carbon atoms the two $R^a$ are bonded to;

each $R^b$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^G)_3$, $OR^H$, $SR^H$, $OSO_2R^J$, $S(O)_xR^J$, —$S(O)_xN(R^K)_2$, $N(R^K)_2$, $C(=O)N(R^K)_2$, $C(=S)N(R^K)_2$, $C(=O)OR^H$, or two $R^b$ present on one carbon atom are together =O, =C($R^L$)$_2$, =$NR^K$, =$NOR^H$, =$NNR^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently selected from the group consisting of halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$;

each $R^d$ is independently selected from the group consisting of halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$, or two $R^d$ present on one atom of a saturated or partially unsaturated heterocyclic ring are together =O, =C($R^L$)$_2$; =$NR^K$, =$NOR^H$ or =$NNR^K$;

each $R^e$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^f$ is independently selected from the group consisting of hydrogen, cyano, $C_1$-$C_6$-alkyl, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;
$Si(R^e)_3$, $S(O)_xR^B$, —$S(O)_xN(R^D)_2$, $N(R^D)_2$, —N=$C(R^F)_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^h$ is independently selected from the group consisting of hydrogen, cyano, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;
$N(R^D)_2$, —N=$C(R^F)_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^i$ is independently selected from the group consisting of hydrogen, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;
$S(O)_xR^B$, —$S(O)_xN(R^D)_2$, $C(=O)R^S$, $C(=O)OR^A$, $C(=O)N(R^D)_2$, $C(=S)R^S$, $C(=S)SR^A$, $C(=S)N(R^D)_2$, $C(=NR^D)R^S$, phenyl unsubstituted or substituted with up to 5 $R^E$;
a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^E$, or two $R^i$ on one nitrogen atom are together a $C_2$-$C_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from the group consisting of N, O, S, NO, SO, $SO_2$, and wherein the alkylene chain is unsubstituted or substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl, $C_2$-$C_6$-haloalkynyl;

each $R^m$ is independently selected from the group consisting of hydrogen, —SCN, $SF_5$, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;
$Si(R^e)_3$, $OR^A$, $SR^A$, $OSO_2R^B$, $N(R^D)_2$, $C(=O)N(R^D)_2$, $C(=S)N(R^D)_2$, $C(=O)OR^A$, phenyl unsubstituted or substituted with up to 5 $R^E$;
a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$;

each $R^A$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^B$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^D$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$-alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or two $R^D$ on one nitrogen atom are together a $C_2$-$C_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from the group consisting of N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently selected from the group consisting of cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

each $R^F$ is independently selected from the group consisting of $C_1$-$C_4$ alkyl, $C_1$-$C_6$ cycloalkyl, $C_1$-$C_4$ alkoxyalkyl, phenyl and benzyl;

each $R^G$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^J$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently $C_1$-$C_4$ alkyl or $C_1$-$C_4$ alkoxyalkyl;

each $R^M$ is independently selected from the group consisting of halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

each $R^N$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently selected from the group consisting of hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1;

x is 1 or 2, with the proviso that the following compound is excluded:

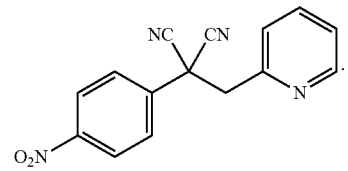 [SMILES: N#CC(C#N)(Cc1ccccn1)c1ccc([N+](=O)[O-])cc1]

22. A seed treated in accordance with the method of claim 21.

23. A method for treating or protecting animals against infestation or infection by parasites comprising orally, topically or parenterally administering or applying to the animals a parasiticidally effective amount of at least one compound of formula (I)

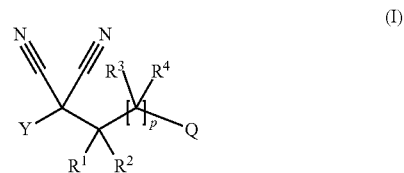

or a salt or N-oxide thereof, wherein

Y is phenyl unsubstituted or substituted with 1, 2, 3, 4 or 5 substituents $R^5$; or naphthyl unsubstituted or substituted with 1, 2, 3, 4, 5, 6 or 7 substituents $R^5$;

Q is a 6-membered aromatic heterocyclic ring containing 1, 2, 3 or 4 nitrogen atoms in the ring, wherein the aforementioned ring is unsubstituted or substituted with 1, 2, 3 or 4 substituents $R^6$;

$R^1$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;

$R^2$ is hydrogen or halogen;

or $R^1$ and $R^2$ form together with the carbon atom to which they are attached a methylene group or a cyclopropyl group;

$R^3$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;

$R^4$ is hydrogen or halogen;

or $R^3$ and $R^4$ form together with the carbon atom to which they are attached a methylene group or a cyclopropyl group;

each $R^5$, $R^6$ is independently selected from the group consisting of halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;

$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;

phenyl unsubstituted or substituted with up to 5 $R^c$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^d$;

$Si(R^e)_3$, $OR^f$, $SR^f$, $OS(O)_xR^h$, $S(O)_xR^h$, $N(R^i)$, $N(R^i)C(=O)R^m$, $OC(=O)R^m$, $C(=O)R^m$, $C(=O)OR^f$, $C(=NR^i)R^m$, $C(=S)R^m$;

or two $R^5$ on two adjacent carbon atoms present on one phenyl ring are together a bridge selected from the group consisting of $CH_2CH_2CH_2CH_2$, N=CH—CH=CH, CH=N—CH=CH, N=CH—N=CH, N=CH—CH=N, $OCH_2CH_2CH_2$, OCH=CHCH_2, $CH_2OCH_2CH_2$, $OCH_2CH_2O$, $OCH_2OCH_2$, $CH_2CH_2CH_2$, CH=CHCH_2, $CH_2CH_2O$, CH=CHO, $CH_2OCH_2$, $CH_2C(=O)O$, $C(=O)OCH_2$, $O(CH_2)O$, $SCH_2CH_2CH_2$, SCH=CHCH_2, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from =O, OH, $CH_3$, $OCH_3$, halogen, halomethyl and halomethoxy;

each $R^7$ is independently selected from the group consisting of halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;

each $R^a$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^e)_3$, $OR^A$, $SR^A$, $OSO_2R^B$, $S(O)_xR^B$, —$S(O)_xN(R^D)_2$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^E$, or two $R^a$ present on one carbon atom are together =O, =$C(R^F)_2$, =$NR^D$, =$NOR^A$, =$NNR^D$, or two $R^a$ form a 3-, 4-, 5-, 6-, 7- or 8-membered saturated or partially unsaturated carbocyclic or heterocyclic ring together with the carbon atoms the two $R^a$ are bonded to;

each $R^b$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^G)_3$, $OR^H$, $SR^H$, $OSO_2R^J$, $S(O)_xR^J$, —$S(O)_xN(R^K)_2$, $N(R^K)_2$, $C(=O)N(R^K)_2$, $C(=S)N(R^K)_2$, $C(=O)OR^H$, or two $R^b$ present on one carbon atom are together =O, =$C(R^L)_2$; =$NR^K$, =$NOR^H$, =$NNR^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently selected from the group consisting of halogen, cyano, azido, nitro, —SCN, SF $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$;

each $R^d$ is independently selected from the group consisting of halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, $-S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$, or two $R^d$ present on one atom of a saturated or partially unsaturated heterocyclic ring are together $=O$, $=C(R^L)_2$; $=NR^K$, $=NOR^H$ or $=NNR^K$;

each $R^e$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^f$ is independently selected from the group consisting of hydrogen, cyano, $C_1$-$C_6$-alkyl, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $S(O)_xR^B$, $-S(O)_xN(R^D)_2$, $N(R^D)_2$, $-N=C(R^F)_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^h$ is independently selected from the group consisting of hydrogen, cyano, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$N(R^D)_2$, $-N=C(R^F)_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^i$ is independently selected from the group consisting of hydrogen, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$S(O)_xR^B$, $-S(O)_xN(R^D)_2$, $C(=O)R^S$, $C(=O)OR^A$, $C(=O)N(R^D)_2$, $C(=S)R^S$, $C(=S)SR^A$, $C(=S)N(R^D)_2$, $C(=NR^D)R^S$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^E$, or two $R^i$ on one nitrogen atom are together a $C_2$-$C_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from the group consisting of N, O, S, NO, SO, $SO_2$, and wherein the alkylene chain is unsubstituted or substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl, $C_2$-$C_6$-haloalkynyl;

each $R^m$ is independently selected from the group consisting of hydrogen, $-SCN$, $SF_5$, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $OR^A$, $SR^A$, $OSO_2R^B$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$;

each $R^A$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^B$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^D$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$-alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or two $R^D$ on one nitrogen atom are together a $C_2$-$C_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from the group consisting of N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently selected from the group consisting of cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

each $R^F$ is independently selected from the group consisting of $C_1$-$C_4$ alkyl, $C_1$-$C_6$ cycloalkyl, $C_1$-$C_4$ alkoxyalkyl, phenyl and benzyl;

each $R^G$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^J$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently $C_1$-$C_4$ alkyl or $C_1$-$C_4$ alkoxyalkyl;

each $R^M$ is independently selected from the group consisting of halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

each $R^N$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently selected from the group consisting of hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1;

x is 1 or 2, with the proviso that the following compound is excluded:

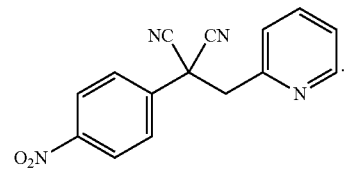 [SMILES: N#CC(C#N)(Cc1ccccn1)c1ccc([N+](=O)[O-])cc1]

* * * * *